US010426824B1

(12) United States Patent
Hacohen et al.

(10) Patent No.: US 10,426,824 B1
(45) Date of Patent: Oct. 1, 2019

(54) COMPOSITIONS AND METHODS OF IDENTIFYING TUMOR SPECIFIC NEOANTIGENS

(71) Applicants: The General Hospital Corporation, Boston, MA (US); Dana Farber Cancer Institute, Inc., Boston, MA (US)

(72) Inventors: Nir Hacohen, Brookline, MA (US); Catherine J. Wu, Brookline, MA (US)

(73) Assignees: The General Hospital Corporation, Boston, MA (US); Dana Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 16/188,737

(22) Filed: Nov. 13, 2018

Related U.S. Application Data

(60) Continuation of application No. 15/187,174, filed on Jun. 20, 2016, now abandoned, which is a division of application No. 14/794,449, filed on Jul. 8, 2015, which is a division of application No. 13/108,610, filed on May 16, 2011, now Pat. No. 9,115,402.

(60) Provisional application No. 61/334,866, filed on May 14, 2010.

(51) Int. Cl.

| | |
|---|---|
| ***A61P 35/00*** | (2006.01) |
| ***A61K 39/00*** | (2006.01) |
| ***C12Q 1/6886*** | (2018.01) |
| ***A61K 39/395*** | (2006.01) |
| ***G16B 15/00*** | (2019.01) |

(52) U.S. Cl.
CPC .... *A61K 39/0011* (2013.01); *A61K 39/39558* (2013.01); *A61P 35/00* (2018.01); *C12Q 1/6886* (2013.01); *G16B 15/00* (2019.02)

(58) Field of Classification Search
CPC ........ A61P 35/00
USPC ........ 703/11
See application file for complete search history.

(56) References Cited

U.S. PATENT DOCUMENTS

| | | | |
|---|---|---|---|
| 2007/0055049 | A1 | 3/2007 | Grey et al. |
| 2009/0136494 | A1 | 5/2009 | Ponath et al. |
| 2009/0220980 | A1 | 9/2009 | Hoon et al. |
| 2011/0257890 | A1 | 10/2011 | Weinschenk et al. |
| 2012/0082691 | A1 | 4/2012 | Rammensee et al. |
| 2012/0288539 | A1 | 11/2012 | Eber |
| 2014/0056986 | A1 | 2/2014 | Desai et al. |
| 2017/0160269 | A1 | 6/2017 | Linnemann et al. |
| 2018/0127803 | A1 | 5/2018 | Lei et al. |
| 2019/0060428 | A1 | 2/2019 | Fritsch |
| 2019/0060432 | A1 | 2/2019 | Hacohen et al. |
| 2019/0099475 | A1 | 4/2019 | Benz et al. |

FOREIGN PATENT DOCUMENTS

| | | | |
|---|---|---|---|
| WO | WO-00/66153 | A1 | 11/2000 |
| WO | WO-2006/121168 | A1 | 11/2006 |
| WO | WO-2007/059033 | A1 | 5/2007 |
| WO | WO2007/101227 | * | 9/2007 |
| WO | WO-2008/096831 | A1 | 8/2008 |
| WO | WO-2012/095639 | A2 | 7/2012 |
| WO | WO-2013/026027 | A1 | 2/2013 |
| WO | WO-2013/123031 | A2 | 8/2013 |
| WO | WO-2013/173223 | A1 | 11/2013 |
| WO | WO-2014/150924 | A2 | 9/2014 |
| WO | WO-2016/020710 | A1 | 2/2016 |

OTHER PUBLICATIONS

Parmiani et al. (2007) J Immunol, 178:1975-1979. (Year: 2007).*
Sette et al. (1994) Molecular Immunology 31:813-822. (Year: 1994).*
Backert et al., "Immunoinformatics and epitope prediction in the age of genomic medicine," Genome Medicine, 7:119 (2015).
Berger et al.,"Melanoma genome sequencing reveals frequent PREX2 mutations," Nature, 485(7399):502 (2012).
Bettelli et al., "TH-17 cells in the circle of immunity and autoimmunity," Nat Immunol, 8:345-350 (2007).
Carreno et al., "A dendritic cell vaccine increases the breadth and diversity of melanoma neoantigen-specific T cells," Science, 348(6239):803-808 (2015).
Chatila, "The Regulatory T Cell Transcriptosome: E Pluribus Unum," Immunity, 27(5):693-695 (2007).
Chen et al., Molecular Pharmaceutics, 3:109-111 (2010).
Ciofani et al., "A Validated Regulatory Network for Th17 Cell Specification," Cell, 151(2):289-303 (2012).
Declaration by Professor John Haanen, M.D., Ph.D.
Dössinger et al., "MHC multimer-guided and cell culture-independent isolation of functional T cell receptors from single cells facilitates TCR identification for immunotherapy," PloS one, 8(4):e61384 (2013).
Final Rejection for U.S. Appl. No. 13/108,610, "Compositions and Methods of Identifying Tumor Specific Neoantigens," dated May 12, 2014.
Final Rejection for U.S. Appl. No. 14/794,449, "Compositions and Methods of Identifying Tumor Specific Neoantigens," dated Sep. 13, 2017.
Final Rejection for U.S. Appl. No. 14/877,125, "Compositions and Methods for Personalized Neoplasia Vaccines," dated Oct. 25, 2017.
Final Rejection for U.S. Appl. No. 15/038,504 , "Compositions and Methods for Diagnosing, Evaluating and Treating Cancer by Means of the DNA Methyl," dated Apr. 30, 2018.
Final Rejection for U.S. Appl. No. 15/038,504 , "Compositions and Methods for Diagnosing, Evaluating and Treating Cancer by Means of the DNA Methyl," dated Dec. 21, 2018.

(Continued)

*Primary Examiner* — Jerry Lin
(74) *Attorney, Agent, or Firm* — Foley Hoag LLP

(57) ABSTRACT

The present invention related to immunotherapeutic peptides and their use in immunotherapy, in particular the immunotherapy of cancer. Specifically, the invention provides a method of identifying tumor specific neoantigens that alone or in combination with other tumor-associated peptides serve as active pharmaceutical ingredients of vaccine compositions which stimulate anti-tumor responses.

20 Claims, 17 Drawing Sheets

Specification includes a Sequence Listing.

(56) References Cited

OTHER PUBLICATIONS

Final Rejection for U.S. Appl. No. 15/102,129, "Formulations for Neoplasia Vaccines," dated Sep. 14, 2018.
Final Rejection for U.S. Appl. No. 15/105,961, "Combination Therapy With Neoantigen Vaccine," dated Jul. 5, 2018.
Final Rejection for U.S. Appl. No. 15/187,174, "Compositions and Methods of Identifying Tumor Specific Neoantigens," dated May 25, 2017.
Final Rejection for U.S. Appl. No. 15/187,174, "Compositions and Methods of Identifying Tumor Specific Neoantigens," dated Oct. 12, 2018.
Gazdar, "Activating and resistance mutations of EGFR in non-small-cell lung cancer: role in clinical response to EGFR tyrosine kinase inhibitors," Oncogene, 28:S24-S31 (2009).
Han et al., "Linking T-Cell Receptor Sequence to Fucntional Phenotype at the Single-Cell Level," Nat Biotechnol, 32:684-692 (2014).
Hombrink et al., "Identification of Biological Relevant Minor Histocompatibility Antigens within the B-lymphocyte—Derived HLA-Ligandome Using a Reverse Immunology Approach," Clin Cancer Res, 21(9):2177-2186 (2015).
Illumina, "Immunotherapy, the Next Generation of Cancer Treatment, NGS-guided assessment of interactions between tumors and the immune system leads to new discoveries in immuno-oncology," (2016).
International Preliminary Report on Patentability for International Application No. PCT/US2017/028122 dated Oct. 23, 2018.
International Search and Written Opinion for International Application No. PCT/US2017/028122 dated Apr. 18, 2016.
International Search Report and Written Opinion for International Application No. PCT/US2018/014831 dated Apr. 4, 2018.
Jarmalavicius et al., "High Immunogenicity of the Human Leukocyte Antigen Peptidomes of Melanoma Tumor Cells," J Biol Chem, 287(40):33401-33411 (2012).
Johnson et al., "Discovery of Naturally Processed and HLA-Presented Class I Peptides from Vaccinia Virus Infection using Mass Spectrometry for Vaccine Development," Vaccine, 28(1):38-47 (2009).
Jun et al., "Progress in T cell adoptive Immunotherapy for Malignant Solid Tumors," Chin Med Biotechnol, 3(1):1-7 (2008).
Kalaora et al., "Use of HLA peptidomics and whole exome sequencing to identify human immunogenic neo-antigens," Oncotarget, 7(5):5110-5117 (2016).
Keskin et al., "Neoantigen vaccine generates intratumoral T cell responses in phase lb glioblastoma trial," Nature, 565(7738):234-239 (2019).
Kim et al., "mTOR inhibitors radiosensitize PTEN-deficient non-small-cell lung cancer cells harboring an EGFR activating mutation by inducing autophagy," J Cell Biochem, 114(6):1248-1256 (2013).
Klug et al., "Characterization of MHC Ligands for Peptide Based Tumor Vaccination," Current Pharmaceutical Design, 15(28): 3221-3236 (2009).
Lata et al., "MHCBN 4.0: A database of MHC/TAP binding peptides and T-cell epitopes," BMC Research Notes, 2(1): 61 (2009).
Linardou et al., "Assessment of somatic k-RAS mutations as a mechanism associated with resistance to EGFR-targeted agents: a systematic review and meta-analysis of studies in advanced non-small-cell lung cancer and metastatic colorectal cancer," Lancet Oncol, 9(10):962-972 (2008).
Linardou et al., "Somatic EGFR mutations and efficacy of tyrosine kinase inhibitors in NSCLC," Nat Rev Clin Oncol, 6(6):352-366 (2009).
Lucas et al., "About human tumor antigens to be used in immunotherapy," Semin Immunol, 20(5):301-307 (2008).
Luo et al. "Machine learning methods for Predicting hla—Peptide Binding activity," Bioinformatics and Biology Insights, 9(s3):21-29 (2015).
Mosmann et al., "TH1 and TH2 Cells: Different Patterns of Lymphokine Secretion Lead to Different Functional Properties," Ann Rev Immunol, 7:145-173 (1989).
Nielsen et al., "NetMHCpan-3.0; improved prediction of binding to MHC class I molecules integrating information from multiple receptor and peptide length datasets," Genome Medicine, 8:33 (2016).
Non-Final Office Action for U.S. Appl. No. 13/108,610, "Compositions and Methods of Identifying Tumor Specific Neoantigens," dated Aug. 15, 2013.
Non-Final Office Action for U.S. Appl. No. 13/108,610, "Compositions and Methods of Identifying Tumor Specific Neoantigens," dated Dec. 3, 2014.
Non-Final Office Action for U.S. Appl. No. 14/794,449, "Compositions and Methods of Identifying Tumor Specific Neoantigens," dated Dec. 29, 2016.
Non-Final Office Action for U.S. Appl. No. 14/794,449, "Compositions and Methods of Identifying Tumor Specific Neoantigens," dated Jul. 24, 2018.
Non-Final Office Action for U.S. Appl. No. 14/877,125, "Compositions and Methods for Personalized Neoplasia Vaccines," dated Mar. 27, 2017.
Non-Final Office Action for U.S. Appl. No. 14/877,125, "Compositions and Methods for Personalized Neoplasia Vaccines," dated Nov. 2, 2018.
Non-Final Office Action for U.S. Appl. No. 15/038,504 , "Compositions and Methods for Diagnosing, Evaluating and Treating Cancer by Means of the DNA Methyl," dated Sep. 6, 2017.
Non-Final Office Action for U.S. Appl. No. 15/102,129, "Formulations for Neoplasia Vaccines," dated Dec. 17, 2018.
Non-Final Office Action for U.S. Appl. No. 15/102,129, "Formulations for Neoplasia Vaccines," dated Jul. 28, 2017.
Non-Final Office Action for U.S. Appl. No. 15/102,129, "Formulations for Neoplasia Vaccines," dated Mar. 7, 2018.
Non-Final Office Action for U.S. Appl. No. 15/105,961, "Combination Therapy With Neoantigen Vaccine," dated Jan. 8, 2019.
Non-Final Office Action for U.S. Appl. No. 15/105,961, "Combination Therapy With Neoantigen Vaccine," dated Nov. 20, 2017.
Non-Final Office Action for U.S. Appl. No. 15/187,174, "Compositions and Methods of Identifying Tumor Specific Neoantigens," dated Dec. 5, 2016.
Non-Final Office Action for U.S. Appl. No. 15/187,174, "Compositions and Methods of Identifying Tumor Specific Neoantigens," dated Jan. 22, 2018.
Non-Final Office Action for U.S. Appl. No. 15/513,127, "Use of Clonal Evolution Analysis for Ibrutinib Resistance in Chronic Lymphocytic Leukemia Patients," dated Nov. 26, 2018.
Non-Final Office Action for U.S. Appl. No. 15/537,785, "Methods for Profiling the T Cell Repertoire," dated Dec. 21, 2018.
Non-Final Office Action for U.S. Appl. No. 16/181,098, "Compositions and Methods of Identifying Tumor Specific Neoantigens," dated Jan. 31, 2019.
Notice of Allowance for U.S. Appl. No. 13/108,610, "Compositions and Methods of Identifying Tumor Specific Neoantigens," dated Jun. 11, 2015.
Notice of Allowance for U.S. Appl. No. 13/108,610, "Compositions and Methods of Identifying Tumor Specific Neoantigens," dated May 12, 2015.
Notice of Allowance for U.S. Appl. No. 15/102,129, "Formulations for Neoplasia Vaccines," dated Oct. 12, 2018.
O'Shea et al., "Signal transduction and Th17 cell differentiation," Microbes Infect, 11(5):599-611 (2009).
Peters et al., "The many faces of TH-17 Cells," Curr Opin Immunol, 23(6):702-706 (2011).
Restriction Requirement for U.S. Appl. No. 13/108,610, "Compositions and Methods of Identifying Tumor Specific Neoantigens," dated Mar. 7, 2013.
Restriction Requirement for U.S. Appl. No. 14/794,449, "Compositions and Methods of Identifying Tumor Specific Neoantigens," dated Oct. 26, 2016.
Restriction Requirement for U.S. Appl. No. 14/877,125, "Compositions and Methods for Personalized Neoplasia Vaccines," dated Nov. 18, 2016.
Restriction Requirement for U.S. Appl. No. 15/038,504 , "Compositions and Methods for Diagnosing, Evaluating and Treating Cancer by Means of the DNA Methyl," dated Jun. 22, 2017.

(56) References Cited

OTHER PUBLICATIONS

Restriction Requirement for U.S. Appl. No. 15/102,129, "Formulations for Neoplasia Vaccines," dated May 8, 2017.
Restriction Requirement for U.S. Appl. No. 15/105,961 , "Combination Therapy With Neoantigen Vaccine," dated Jul. 13, 2017.
Restriction Requirement for U.S. Appl. No. 15/187,174, "Compositions and Methods of Identifying Tumor Specific Neoantigens," dated Sep. 9, 2016.
Restriction Requirement for U.S. Appl. No. 15/513,127, "Use of Clonal Evolution Analysis for Ibrutinib Resistance in Chronic Lymphocytic Leukemia Patients," dated Aug. 13, 2018.
Restriction Requirement for U.S. Appl. No. 15/537,785, "Methods for Profiling the T Cell Repertoire," dated Mar. 22, 2018.
Restriction Requirement for U.S. Appl. No. 15/575,328, "Shared Neoantigens," dated Feb. 7, 2019.
Rubin et al., "Mutation patterns in cancer genomes," PNAS, 106(51):21766-21770 (2009).
Sahin et al., "Personalized RNA mutanome vaccines mobilize poly-specific therapeutic immunity against cancer," Nature, 547(7662):222-226 (2017).
Stranzl et al., "NetCTLpan: pan-specific MHC class I pathway epitope predictions," Immunogenetics, 62(6):357-368 (2010).
Sun et al., Material bionics and Thinking Innovation, 176-177 (2012).
Tang et al., "NeoantigenR: An annotation based pipeline for tumor neoantigen identification from sequencing data," bioRxiv preprint first posted online Aug. 8, 2017.
Trolle et al., "Automated benchmarking of peptide-MHC class I binding predictions," Bioinformatics, 31(13):2174-2181 (2015).
Turchaninova et al., "Pairing of T-cell receptor chains via emulsion PCR," Eur J Immunol, 43:2507-2515 (2013).
Van Buuren et al., "High sensitivity of cancer exome-based CD8 T cell neo-antigen identification," OncoImmunology, 3(5):e28836 (2014).
Vogel et al., "Mass Spectrometry Reveals Changes in MHC I Antigen Presentation After Lentivector Expression of a Gene Regulation System," Molecular Therapy—Nucleic Acids, 2:e75 (2013).
Wang et al., Functional Polymeric Material, 1-44 (2010).
Wraith, "The Future of Immunotherapy: A 20-Year Perspective," Front Immunol, 8:1668 (2017).
Yosef et al., "Dynamic regulatory network controlling TH17 cell differentiation," Nature, 496(7446):461-468 (2013).
Zhang et al., Oncology, 1-44 (2005).
Zhou et al., "Transcriptional regulatory networks in Th17 cell differentiation," Curr Opin Immunol, 21(2):146-152 (2009).
Andreatta et al., "Gapped sequence alignment using artificial neural networks: application to the MHC class I system," Bioinformatics 32(4):511-517 (2016).
Bassani-Sternberg et al., "Mass Spectrometry of Human Leukocyte Antigen Class I Peptidomes Reveals Strong Effects of Protein Abundance and Turnover on Antigen Presentation," Mol Cell Proteomics, 14:658-673 (2015).
Behrends et al., "Network organization of the human autophagy system," Nature, 466(7302):68-76 (2010).
Berg et al., "Detection of artifacts and peptide modifications in liquid chromatography/mass spectrometry data using two-dimensional signal intensity map data visualization," Rapid Commun Mass Spectrom, 20(10):1558-1562 (2006).
Boen et al., "Identification of T Cell Ligands in a Library of Peptides Covalently Attached to HLA-DR4," J Immunol, 165:2040-2047 (2000).
Boisgerault et al., "Definition of the HLA-A29 peptide ligand motif allows prediction of potential T-cell epitopes from the retinal soluble antigen, a candidate autoantigen in birdshot retinopathy," PNAS, 93:3466-3470 (1996).
Bourdetsky et al., The nature and extent of contributions by defective ribosome products to the HLA peptidome, PNAS, III, E1591-E1599 (2014).
Bremel et al., "An integrated approach to epitope analysis I: Dimensional reduction, visualization and prediction of MHC binding using amino acid principal components and regression approaches," Immunome Res, 6:7 (2010).
Caron et al., "Analysis of MHC immunopeptidomes using mass spectrometry," Mol Cell Proteomics (2015), doi: 10.1074/mcp.OI 15.052431.
Chowell et al., "TCR contact residue hydrophobicity is a hallmark of immunogenic CD8(+) T cell epitopes," PNAS, 112:E1754-E1762 (2015).
Christianson et al., "Defining human ERAD networks through an integrative mapping strategy," Nat Cell Biol, 14:93-105 (2012).
Eichmann et al., "Identification and characterisation of peptide binding motifs of six autoimmune disease-associated human leukocyte antigen-class I molecules including HLA-B*39:06," Tissue Antigens 84(4):378-388 (2014).
Elias et al., Target-decoy search strategy for increased confidence in large-scale protein identifications by mass spectrometry, Nat Meth, 4:207-214 (2007).
Eyers et al., "CONSeQuence: prediction of reference peptides for absolute quantitative proteomics using consensus machine learning approaches," Mol Cell Proteomics (2011); 10(11):M110.003384. doi: 10.1074/mcp.MI 10.003384. Epub Aug. 3, 2011.
Fusaro et al., "Prediction of high -responding peptides for targeted protein assays by mass spectrometry" Nat Biotechnol, 27(2):190-198 (2009).
Guasp et al., "The Peptidome of Behcet's Disease-Associated HLA-B*51 :01 Includes Two Subpeptidomes Differentially Shaped by Endoplasmic Reticulum Aminopeptidase 1," Arthritis Rheumatol, 68:505-515 (2016).
Guruprasad et al., "Correlation between stability of a protein and its dipeptide composition: a novel approach for predicting in vivo stability of a protein from its primary sequence," Protein Eng, 4(2):155-161 (1990).
Harndahl et al., "Peptide-MHC class I stability is a better predictor than peptide affinity of CTL immunogenicity," Eur J Immunol, 42:1405-1416 (2012).
Harndahl et al., "Real-time, High-Throughput Measurements of Peptide-MHC-I Dissociation Using a Scintillation Proximity Assay," J Immunol Methods, 374:5-12 (2011).
Hickman et al., "Toward a Definition of Self: Proteomic Evaluation of the Class I Peptide Repertoire," J Immunol, 172:2944-2952 (2004).
Hoof et al., "NetMHCpan, a method for MHC class I binding prediction beyond humans," Immunogenetics, 61:1-13 (2009).
Hunt et al., "Characterization of peptides bound to the class I MHC molecule HLA- A2.1 by mass spectrometry," Science, 255:1261-1263 (1992).
Ishihama et al., "Exponentially Modified Protein Abundance Index (emPAI) for Estimation of Absolute Protein Amount in Proteomics by the Number of Sequenced Peptides per Protein," Mol Cell Proteomics, 4:1265-1272 (2005).
Jeffery et al., "The Influence of HLA Class I Alleles and Heterozygosity on the Outcome of Human T Cell Lymphotropic Virus Type I Infection," J Immunol, 165:7278-7284 (2000).
Jorgensen et al., "NetMHC stab—predicting stability of peptide-MHC-I complexes; impacts for cytotoxic T lymphocyte epitope discovery," Immunology 141:18-26 (2014).
Keskin et al., "Direct identification of an HPV-16 tumor antigen from cervical cancer biopsy specimens," Front Immunol, 2:75 (2011).
Keskin et al., "Physical detection of influenza A epitopes identifies a stealth subset on human lung epithelium evading natural CD8 immunity," PNAS, 112(7):2151-2156 (2015).
Kesmir et al., "Prediction of proteasome cleavage motifs by neural networks," Protein Eng, 15(4):287-296 (2002).
Kim et al., "Derivation of an amino acid similarity matrix for peptide:MHC binding and its application as a Bayesian prior," BMC Bioinformatics, 10:1-11 (2009).
Kim et al., "Positional Bias of MHC Class I Restricted T-Cell Epitopes in Viral Antigens is Likely due to a Bias in Conservation," PLoS Comput Biol, 9:el002884 (2013).

(56) References Cited

OTHER PUBLICATIONS

Kronke et al. "Lenalidomide causes selective degradation of IKZFI and IKZF3 in multiple myeloma cells," Science, 343(6168): 301-305 (2014).
Kronke et al. "Lenalidomide induces ubiquitination and degradation of CKla in del(5q) MDS," Nature, 523(7559):183-188 (2015).
Larsen et al., "Large-scale validation of methods for cytotoxic T-lymphocyte epitope prediction," BMC Bioinformatics, 8:424-424 (2007).
Linnemann et al., "High-throughput epitope discovery reveals frequent recognition of neo-antigens by CD4+ T cells in human melanoma," Nat Med, 21:81-85 (2015).
Llano et al., "Best-Characterized HIV-1 CTL Epitopes: The 2013 Update," HIV Mol Immunol , 3-25 (2013).
Lorente et al., "Diversity of Natural Self-Derived Ligands Presented by Different HLA Class I Molecules in Transporter Antigen Processing-Deficient Cells," PLoS ONE 8:e59118 (2013).
Ma, "Novor: Real-Time Peptide de Novo Sequencing Software," J Am Soc Mass Spectrom, 26:1885-1894 (2015).
McMurtrey et al., "Toxoplasma gondii peptide ligands open the gate of the HLA class I binding groove," eLife 5:el2556 (2016).
Milner et al., "The Effect of Proteasome Inhibition on the Generation of the Human Leukocyte Antigen (HLA) Peptidome," Mol Cell Proteomics, 12:1853-1864 (2013).
Milner et al., "The Turnover Kinetics of Major Histocompatibility Complex Peptides of Human Cancer Cells*," Mol Cell Proteomics, 5:357-365 (2006).
Mommen et al., "Expanding the detectable HLA peptide repertoire using electron-transfer/higher-energy collision dissociation (EThcD)," PNAS III, 4507-4512 (2014).
Mommen et al., "Sampling From the Proteome to the Human Leukocyte Antigen-DR (HLA-DR) Ligandome Proceeds Via High Specificity," Mol Cell Proteomics MCP, 15:1412-1423 (2016).
Muntel et al., "Abundance-based Classifier for the Prediction of Mass Spectrometric Peptide Detectability Upon Enrichment (PPA)," Mol Cell Proteomics, 14:430-440 (2015).
Ng et al., "Dereplication and de novo sequencing of nonribosomal peptides," Nat Meth, 6:596-599 (2009).
Nielsen et al., "The role of the proteasome in generating cytotoxic T-cell epitopes: insights obtained from improved predictions of proteasomal cleavage," Immunogenetics, 57:33-41 (2005).
Oates et al., "D(2)P(2): database of disordered protein predictions," Nucleic Acids Res, 41:D508-D516 (2013).
Osorio et al., "Stability Analysis of Antimicrobial Peptides in Solvation Conditions by Molecular Dynamics," Adv Comp Bio, 232:127-131 (2014).
Pritchard et al., "Exome Sequencing to Predict Neoantigens in Melanoma," Cancer Immunol Res, 3:992-998 (2015).
Rappsilber et al., "Protocol for micro-purification, enrichment, pre-fractionation and storage of peptides for proteomics using StageTips," Nat Protoc, 2(8):1896-1906 (2007).
Reche et al., "Elicitation from virus-naive individuals of cytotoxic T lymphocytes directed against conserved HIV-1 epitopes," Med Immunol, 5:1 (2006).
Robinson et al., "The IPD and FMGT/HLA database: allele variant databases," Nucleic Acids Res, 43:D423-D431 (2015).
Rock et al., "Re-examining class-I presentation and the DRiP hypothesis," Trends Immunol, 35(4):144-152 (2014).
Ruggles et al., "An analysis of the sensitivity of proteogenomic mapping of somatic mutations and novel splicing events in cancer," Cell Proteomics, 15(3):1060-1071 (2015).
Saveanu et al., "Concerted peptide trimming by human ERAPI and ERAP2 aminopeptidase complexes in the endoplasmic reticulum," Nat Immunol, 6:689-697 (2005).
Saxova et al., "Predicting proteasomal cleavage sites: a comparison of available methods," Int Immunol, 15:781-787 (2003).
Schumacher et al., "Neoantigens in cancer immunotherapy," Science, 348:69-74 (2015).
Searle et al., "Using Data Independent Acquisition (DIA) to Model High-responding Peptides for Targeted Proteomics Experiments," Mol Cell Proteomics, 14:2331-2340 (2015).
Shimizu et al., "Production of human cells expressing individual transferred HLA-A,-B,-C genes using an HLA-A,-B,-C null human cell line," J Immunol, 142(9):3320-3328 (1989).
Shimizu et al., "Transfer of cloned human class I major histocompatibility complex genes into HLA mutant human lymphoblastoid cells," Mol Cell Biol, 6(4):1074-1087 (1986).
Sidney et al., "Measurement of MHC/Peptide Interactions by Gel Filtration" Curr Prot Immunol, 31(1):18.3.1-18.3.19 (1999).
Sowa et al., "Defining the Human Deubiquitinating Enzyme Interaction Landscape," Cell, 138(2):389-403 (2009).
Trolle et al., "The Length Distribution of Class I-Restricted T Cell Epitopes is Determined by Both Peptide Supply and MHC Allele-Specific Binding Preference," J Immunol (2016), doi: 10.4049/jimmunol.1501721.
Tynan et al., "T cell receptor recognition of a "super-bulged" major histocompatibility complex class I-bound peptide," Nat Immunol, 6:1114-1122 (2005).
Udeshi et al., "Methods for quantification of in vivo changes in protein ubiquitination following proteasome and deubiquitinase inhibition," Mol Cell Proteomics, 11:148-159 (2012).
Vita et al., "The immune epitope database (IEDB) 3.0," Nucleic Acids Res, 43:D405-D412 (2015).
Walz et al., "The antigenic landscape of multiple myeloma: mass spectrometry (re)defines targets for T-cell-based immunotherapy," Blood 126:1203-1213 (2015).
Yewdell, "DRiPs solidify: progress in understanding endogenous MHC class I antigen processing," Trends Immunol, 32(11):548-558 (2011).
Zhang et al., "Dana-Farber repository for machine learning in immunology," J Immunol Methods, 374(1-2):18-25 (2011).
Chang et al., "Use of tumor genomic profiling to reveal mechanisms of resistance to the BTK inhibitor ibrutinib in chronic lymphocytic leukemia (CLL)," J Clin Oncol, 31(15S):Abstract 7014 (2013).
Final Rejection for U.S. Appl. No. 14/794,449, "Compositions and Methods of Identifying Tumor Specific Neoantigens," dated Apr. 5, 2019.
Final Rejection for U.S. Appl. No. 14/877,125, "Compositions and Methods for Personalized Neoplasia Vaccines," dated May 24, 2019.
Final Rejection for U.S. Appl. No. 15/513,127, "Use of Clonal Evolution Analysis for Ibrutinib Resistance in Chronic Lymphocytic Leukemia Patients," dated May 17, 2019.
Final Rejection for U.S. Appl. No. 16/181,098, "Compositions and Methods of Identifying Tumor Specific Neoantigens," dated Jun. 17, 2019.
Fruci et al., "Altered expression of endoplasmic reticulum aminopeptidases ERAPI and ERAP2 in transformed non-lymphoid human tissues," J Cell Physiol, 216(3):742-749 (2008).
Mackall et al., "Targeting tumor specific translocations in sarcomas in pediatric patients for immunotherapy," Clinical Orthopaedics and Related Research, 373:25-31 (2000).
Non-Final Office Action for U.S. Appl. No. 15/102,129, "Formulations for Neoplasia Vaccines," dated Apr. 26, 2019.
Non-Final Office Action for U.S. Appl. No. 15/575,328, "Shared Neoantigens," dated Jun. 27, 2019.
O'Mahony et al., "A Pilot Study of CTLA-4 Blockade after Cancer Vaccine Failure in Patients with Advanced Malignancy" Clin Canc Res 13(3):958-964 (2007).
Pietras, "Biologic Basis of Sequential and Combination Therapies for Hormone-Responsive Breast Cancer," Oncologist, 11:704-717 (2006).
Restriction Requirement for U.S. Appl. No. 15/537,839, "Molecular Biomarkers for Cancer Immunotherapy," dated Jun. 20, 2019.
Song et al., "Full screening and accurate subtyping of HLA-A*02 alleles through group-specific amplification and mono-allelic sequencing," Cell Mol Immunol, 10:490-496 (2013).
Vita et al., "The Immune Epitope Database 2.0," Nucleic Acids Res, 38:D854-D862 (2010).
U.S. Appl. No. 16/094,786, filed Oct. 18, 2018, Pending.

(56) References Cited

OTHER PUBLICATIONS

U.S. Appl. No. 13/108,610, filed May 16, 2011, 2011-0293637, U.S. Pat. No. 9,115,402.
U.S. Appl. No. 14/794,449, filed Jul. 8, 2015, 2016-00008447.
U.S. Appl. No. 15/187,174, filed Jun. 20, 2016, 2016-0331822, Abandoned.
U.S. Appl. No. 15/800,732, filed Nov. 1, 2017, 2018-0055922.
U.S. Appl. No. 16/181,098, filed Nov. 5, 2018, 2019-0060432.
U.S. Appl. No. 16/381,791, filed Apr. 11, 2019, Pending.
U.S. Appl. No. 14/877,125, filed Oct. 7, 2015, 2016-0101170.
U.S. Appl. No. 15/102,129, filed Jun. 6, 2016, 2016-0310584.
U.S. Appl. No. 15/038,504, filed May 23, 2016, 2016-0326593.
U.S. Appl. No. 15/105,961, filed Jun. 17, 2016, 2016-0339090.
U.S. Appl. No. 15/537,785, filed Jun. 19, 2017, 2018-0000913.
U.S. Appl. No. 15/537,839, filed Jun. 19, 2017, 2019-0127803.
U.S. Appl. No. 15/575,328, filed Nov. 17, 2017, 2018-0153975.
U.S. Appl. No. 15/513,127, filed Mar. 21, 2017, 2017-0298441.
U.S. Appl. No. 15/735,566, filed Dec. 11, 2017, 2019-0060428.
PCT/US18/14831, Jan. 23, 2018, WO2018/140391.
11781409.5, May 16, 2011, 2569633.

* cited by examiner

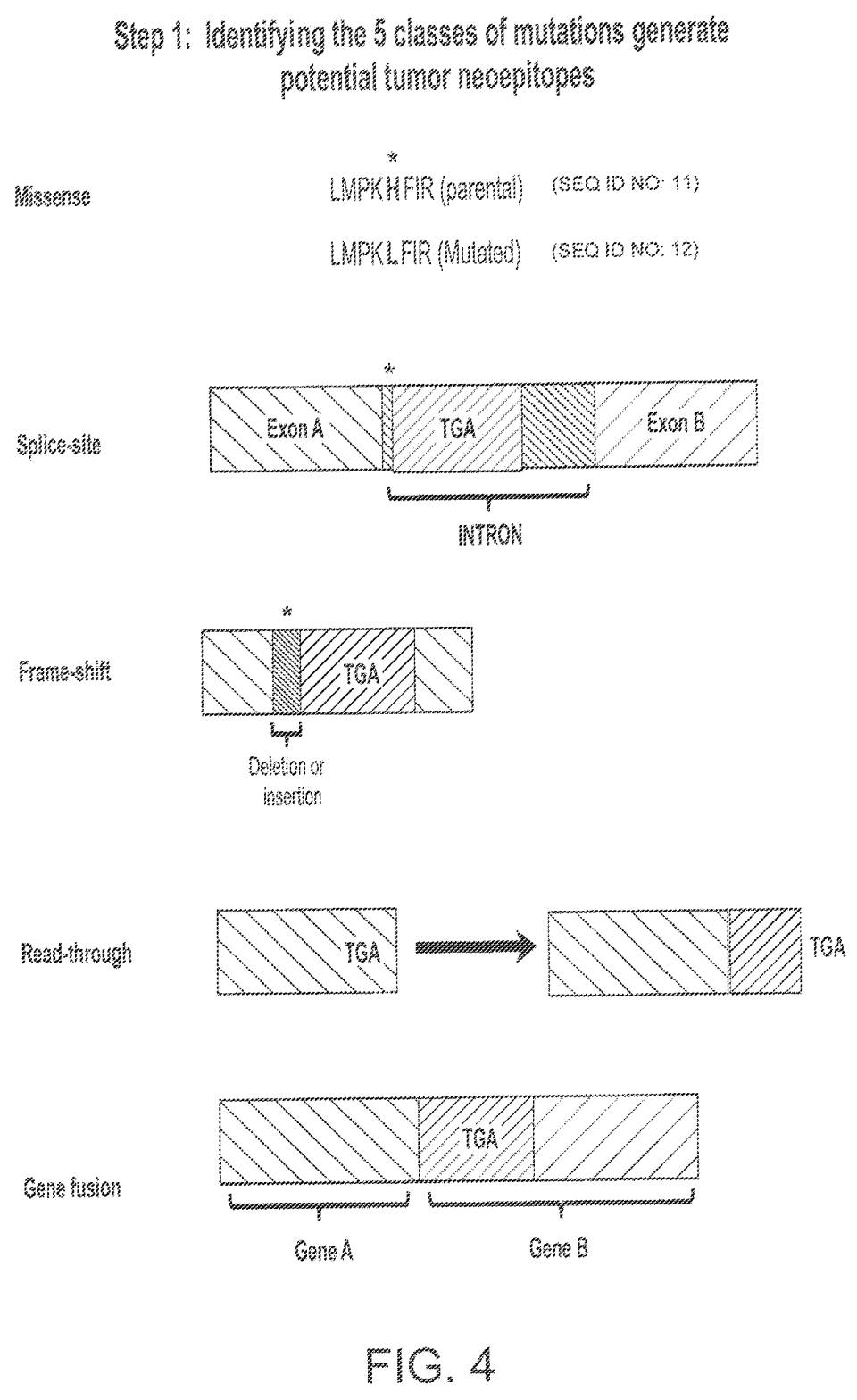

Step 1: Identifying the 5 classes of mutations generate potential tumor neoepitopes Missense

*
LMPK H FIR (parental) (SEQ ID NO: 11)

LMPK L FIR (Mutated) (SEQ ID NO: 12)

Splice-site

*
Exon A | TGA | Exon B

INTRON

Frame-shift

*
TGA

Deletion or insertion

Read-through

TGA → TGA

Gene fusion

TGA

Gene A | Gene B

FIG. 4

Step 2A: Automated peptide predictions against each of patient's HLA alleles

Strong binding affinity $IC_{50}$<50nm (dashed box)

Intermediate binding $IC_{50}$<500nm (solid box)

Non mutated ASILLMTVI

Mutated ASILLMTVT

| | Position | F2R/NM_001992 T@196 | HLA-A*0101 | HLA-A*0201 | HLA-B*0702 | HLA-B*0801 | HLA-C*0701 | HLA-C*0702 |
|---|---|---|---|---|---|---|---|---|
| (SEQ ID NO: 13) | 188-196 | ASILLMTVT | 23671.85 | 19359.42 | 29705.82 | 33914.47 | 30813.86 | 29921.85 |
| (SEQ ID NO: 14) | 189-197 | SILLMTVTS | 33864.61 | 8502.78 | 32065.73 | 14437.61 | 35076.88 | 31257.98 |
| (SEQ ID NO: 15) | 190-198 | ILLMTVTSI | 28921.10 | 41.91 | 11185.03 | 921.87 | 18346.73 | 13844.36 |
| (SEQ ID NO: 16) | 191-199 | LLMTVTSID | 32446.28 | 6105.16 | 31413.94 | 19157.37 | 42419.53 | 41446.55 |
| (SEQ ID NO: 17) | 192-200 | LMTVTSIDR | 30402.31 | 33262.16 | 41747.34 | 39837.33 | 37470.89 | 35512.98 |
| (SEQ ID NO: 18) | 193-201 | MTVTSIDRF | 5066.20 | 17874.71 | 16830.38 | 27827.56 | 7827.33 | 6665.52 |
| (SEQ ID NO: 19) | 194-202 | TVTSIDRFL | 25673.87 | 10165.34 | 17459.35 | 29667.50 | 19864.06 | 20854.32 |
| (SEQ ID NO: 20) | 195-203 | VTSIDRFLA | 4397.21 | 7438.75 | 27799.40 | 34937.23 | 34058.25 | 28879.51 |
| (SEQ ID NO: 21) | 196-204 | TSIDRFLAV | 5703.43 | 527.45 | 9124.17 | 245.43 | 11255.57 | 9553.74 |

FIG. 6

Step 2C: Experimental validation of HLA-peptide binding
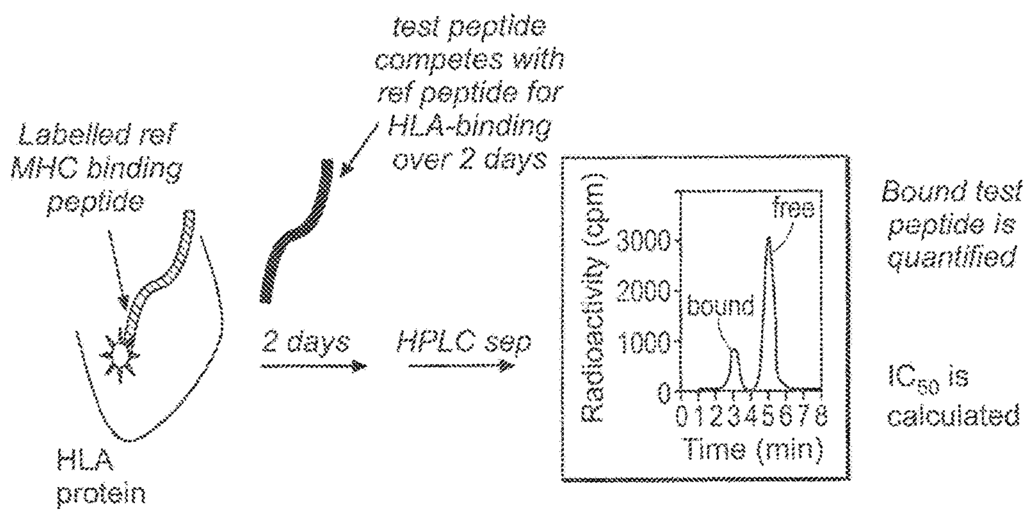
FIG. 8A
| Pt | Class of genetic alteration | # mutated genes | # mutated genes predicted to generate HLA binding peptides | # peptides pre-dicted | Peptides experimentally confirmed/ total tested |
|---|---|---|---|---|---|
| 1 | Missense | 12 | 10 | 30 | 8/17 (47%) |
| | Splice site | 0 | 0 | 0 | 0 |
| | Indel | 16 | 0 | 0 | 0 |
| | Gene fusion | | | | |
| 2 | Missense | 144 | 53 | 116 | 18/29 (46%) |
| | Splice site | 3 | 0 | 0 | 0 |
| | Indel | 6 | 1 | 11 | |
| | Gene fusion | 2 | 2 | 10 | 7/10 (70%) |
FIG. 8B
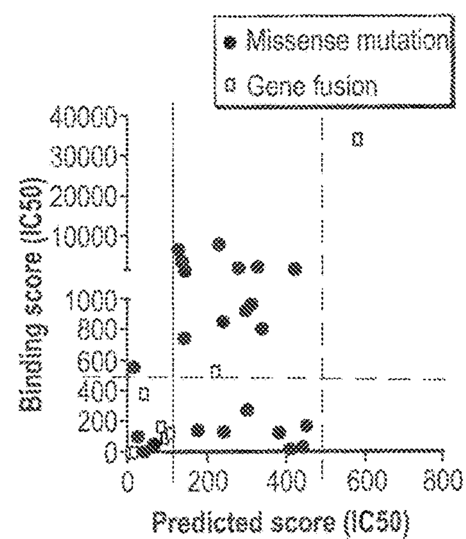
FIG. 8C Predicted differential binding of mutated vs germline peptides to HLA alleles Step 3: T cell reactivity against a candidate personal CLL neoepitope BCR-ABL mutations generate many peptides predicted to bind HLA-A and HLA-B alleles

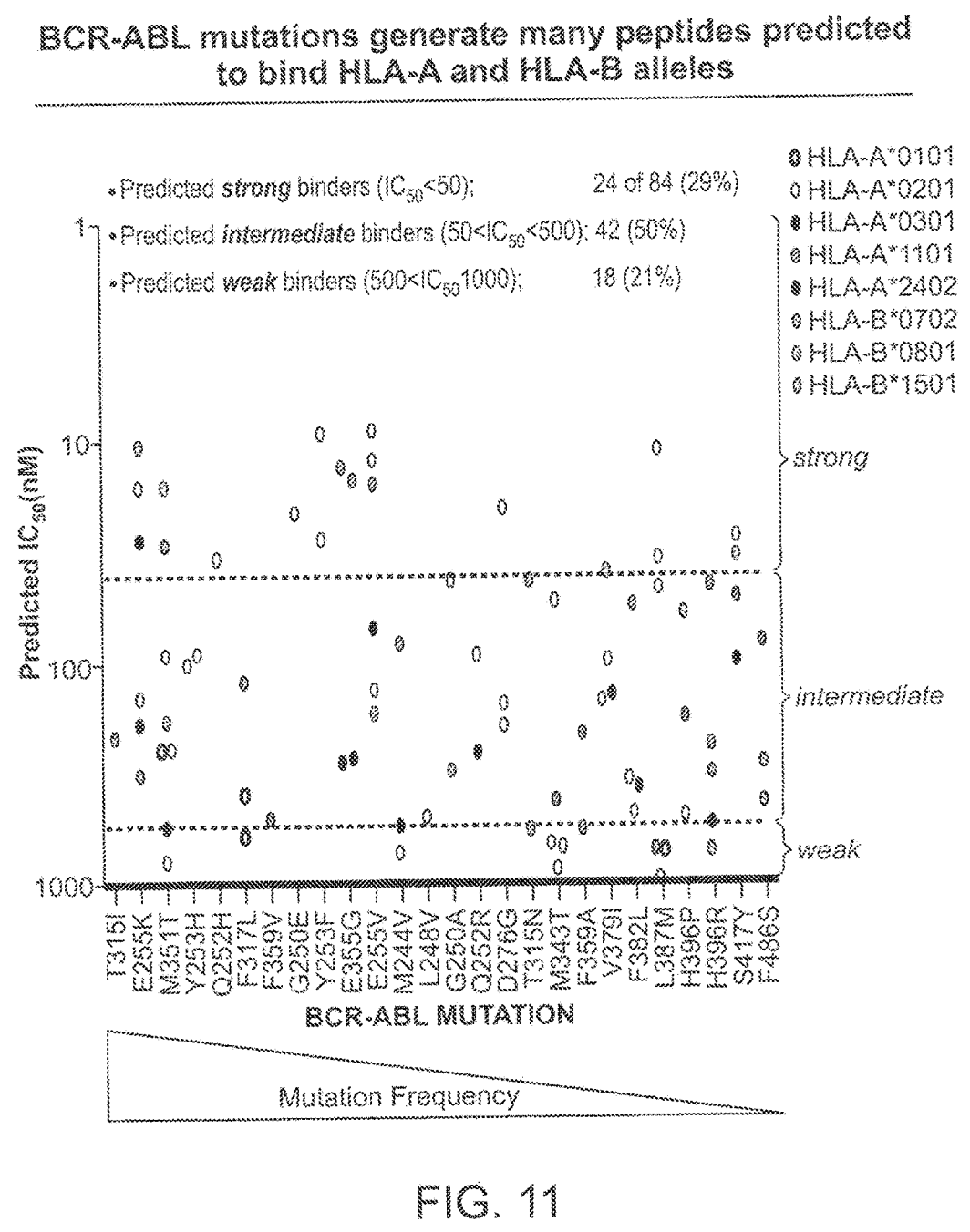

- Predicted *strong* binders ($IC_{50}<50$): 24 of 84 (29%)
- Predicted *intermediate* binders ($50<IC_{50}<500$): 42 (50%)
- Predicted *weak* binders ($500<IC_{50}1000$): 18 (21%)

HLA-A*0101
HLA-A*0201
HLA-A*0301
HLA-A*1101
HLA-A*2402
HLA-B*0702
HLA-B*0801
HLA-B*1501

Predicted $IC_{50}$ (nM)

1
10
100
1000 strong
intermediate
weak

T315I E255K M351T Y253H Q252H F317L F359V G250E Y253F E355G E255V M244V L248V G250A Q252R D276G T315N M343T F359A V379I F382L L387M H396P H396R S417Y F486S

BCR-ABL MUTATION

Mutation Frequency

FIG. 11

| Peptide | Sequence | HLA A03 supertype binding capacity (IC50 nM) | | | | | |
|---|---|---|---|---|---|---|---|
| | | A*0301 | A*1101 | A*3001 | A*3101 | A*3301 | A*6801 |
| E255K-parental | EVYEGVWKK | 1074 | 63 | - | - | 60 | 10 |
| E255K-B | KVYEGVWKK | 17 | 39 | 603 | 202 | 42860 | 45 |

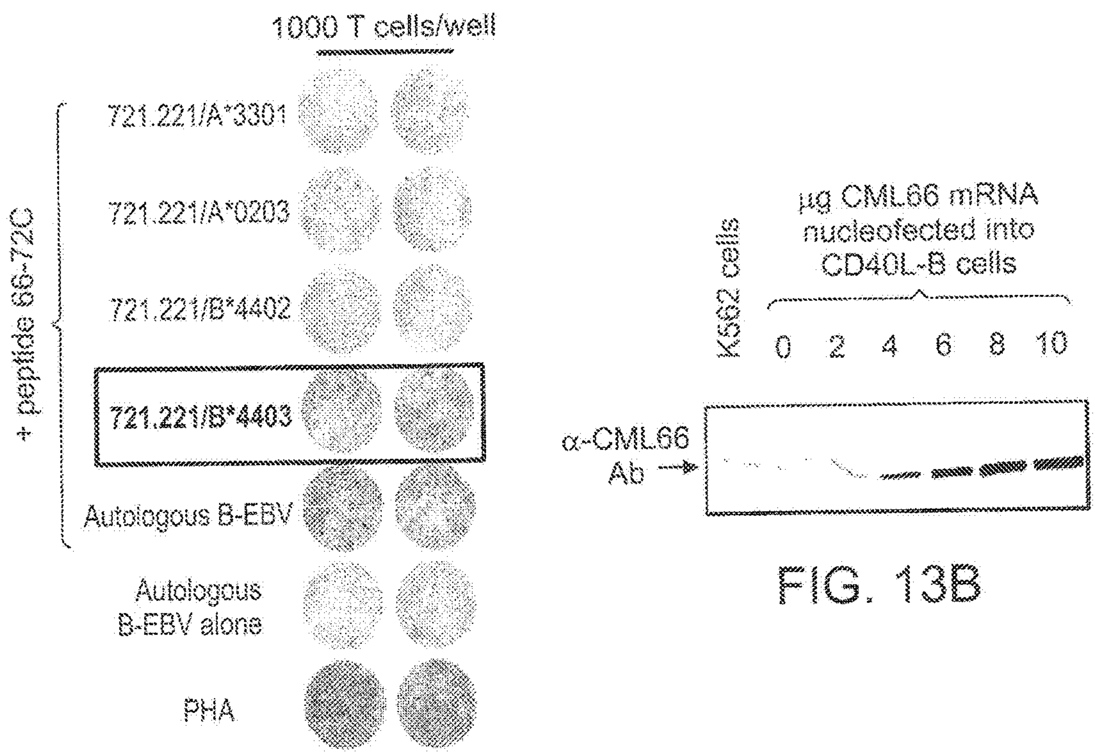
FIG. 13A
FIG. 13B
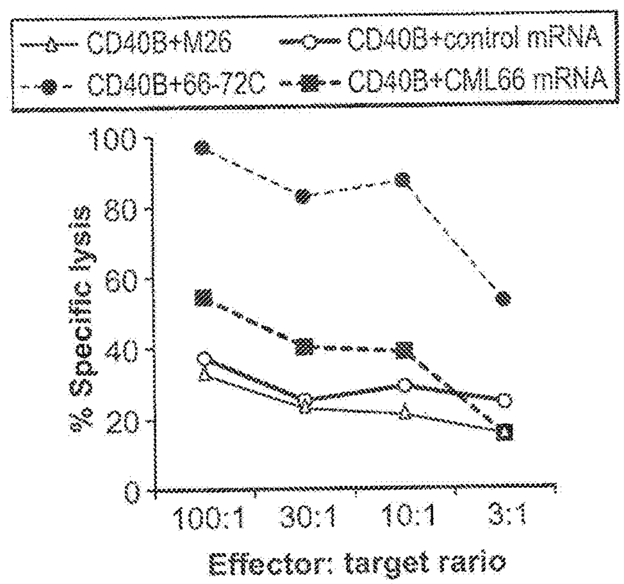
FIG. 13C

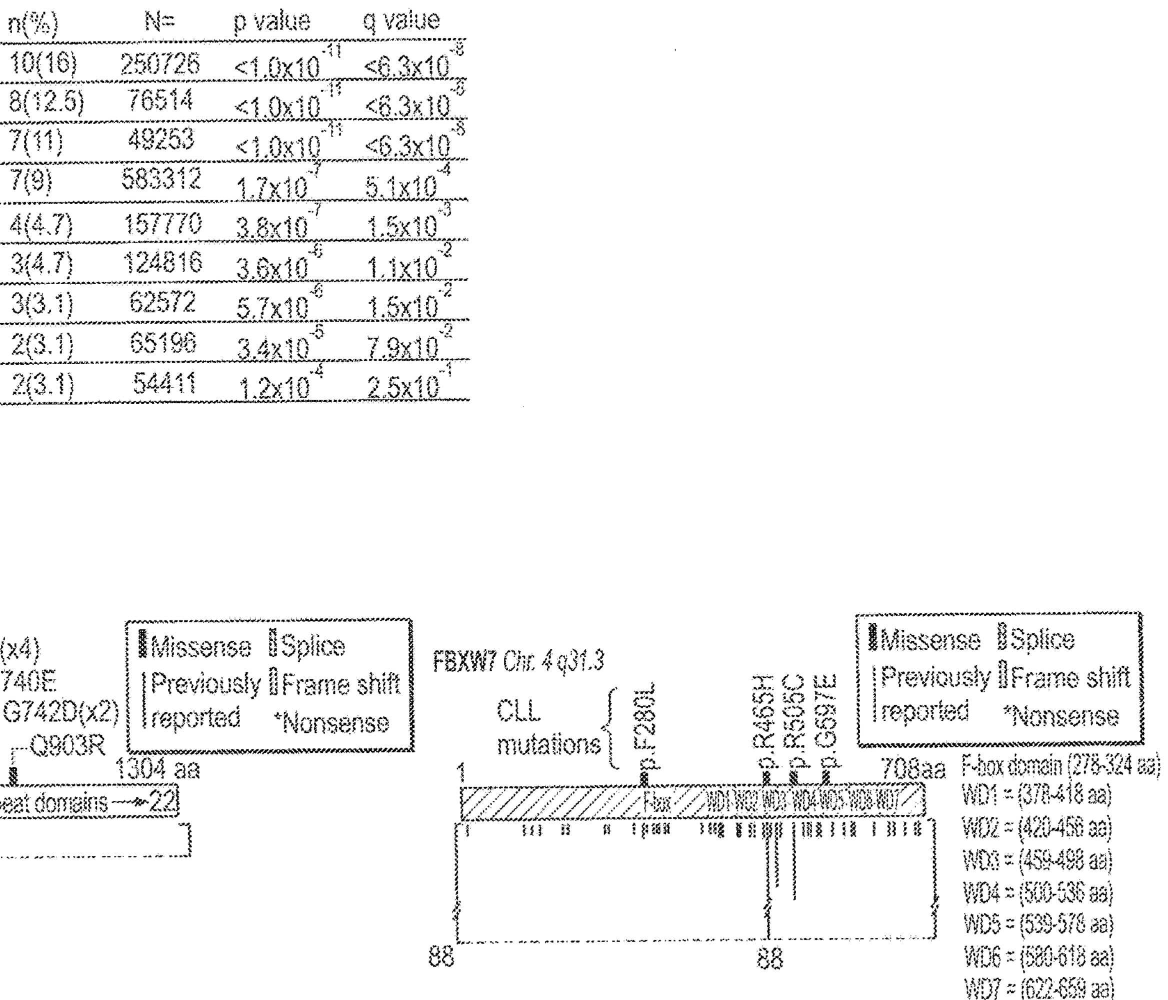
| Gene | n(%) | N= | p value | q value |
|---|---|---|---|---|
| SF3B1 | 10(16) | 250726 | $<1.0\times10^{-11}$ | $<6.3\times10^{-8}$ |
| TP53 | 8(12.5) | 76514 | $<1.0\times10^{-11}$ | $<6.3\times10^{-8}$ |
| MYD88 | 7(11) | 49253 | $<1.0\times10^{-11}$ | $<6.3\times10^{-8}$ |
| ATM | 7(9) | 583312 | $1.7\times10^{-7}$ | $5.1\times10^{-4}$ |
| FBXW7 | 4(4.7) | 157770 | $3.8\times10^{-7}$ | $1.5\times10^{-3}$ |
| DDX3X | 3(4.7) | 124816 | $3.6\times10^{-6}$ | $1.1\times10^{-2}$ |
| MAPK1 | 3(3.1) | 62572 | $5.7\times10^{-6}$ | $1.5\times10^{-2}$ |
| GNB1 | 2(3.1) | 65196 | $3.4\times10^{-5}$ | $7.9\times10^{-2}$ |
| M6PR | 2(3.1) | 54411 | $1.2\times10^{-4}$ | $2.5\times10^{-1}$ |

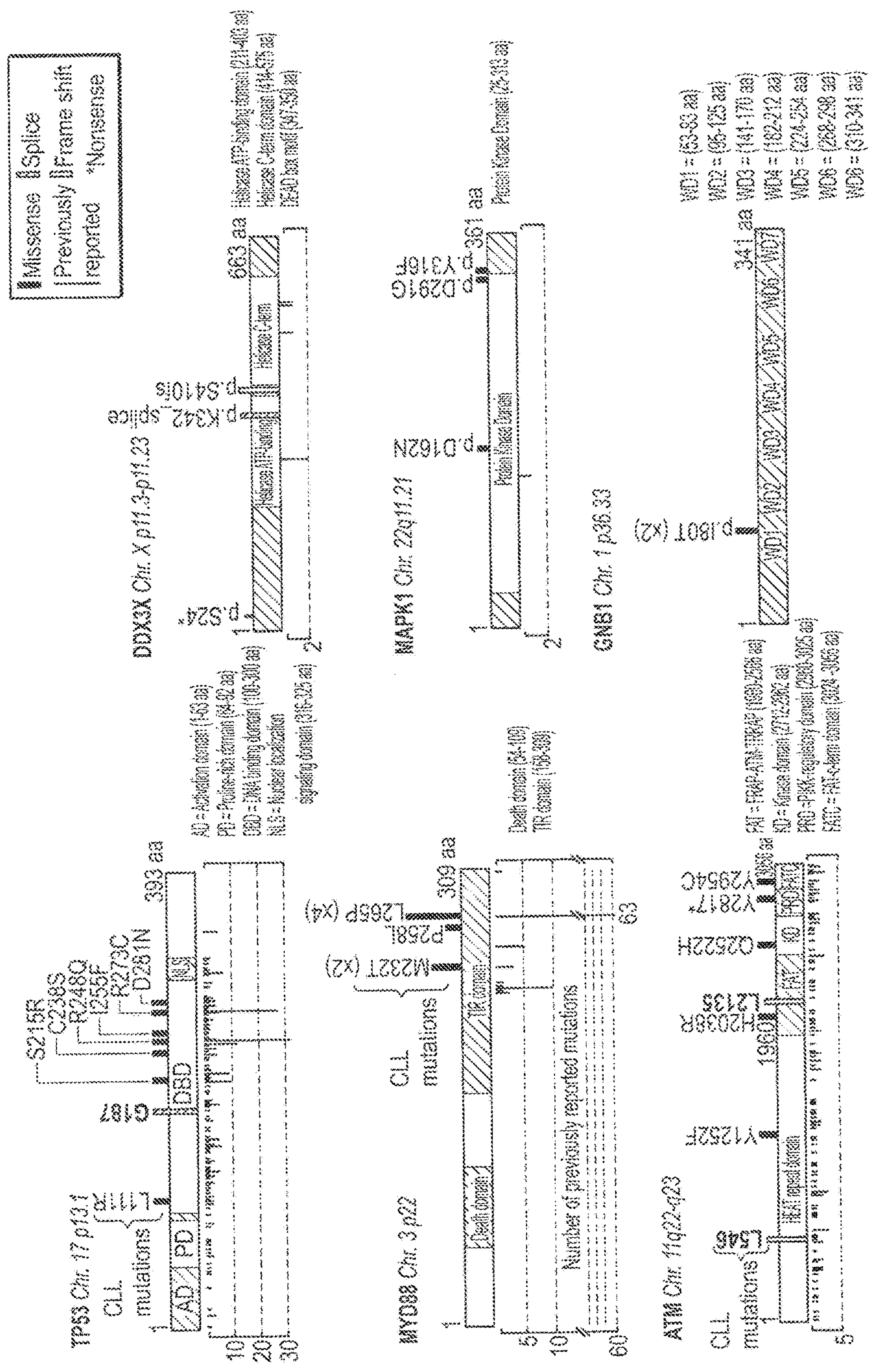

FIG. 14C
Missense
Splice
Previously reported
Frame shift
*Nonsense
TP53 Chr. 17 p13.1
CLL mutations
L111R
G187
S215R
C238S
R248Q
I255F
R273C
D281N
393 aa
AD
PD
DBD
NLS
AD = Activation domain (1-63 aa)
PD = Proline-rich domain (64-92 aa)
DBD = DNA binding domain (100-300 aa)
NLS = Nuclear localization signaling domain (316-325 aa)
MYD88 Chr. 3 p22
CLL mutations
M232T (x2)
P258L
L265P (x4)
309 aa
Death domain
TIR domain
Number of previously reported mutations
Death domain (54-109)
TIR domain (156-309)
ATM Chr. 11q22-q23
CLL mutations
L546
Y1252F
1960
H2038R
L2135
Q2522H
Y2817*
Y2954C
HEAT repeat domain
FAT
KD
PRD
FATC
FAT = FRAP-ATM-TRRAP (1960-2566 aa)
KD = Kinase domain (2712-2962 aa)
PRD = PIKK-regulatory domain (2960-3025 aa)
FATC = FAT-c-term domain (3024-3056 aa)
DDX3X Chr. X p11.3-p11.23
p.S24*
p.K342_splice
p.S410fs
663 aa
Helicase ATP-binding
Helicase C-term
Helicase ATP-binding domain (211-403 aa)
Helicase C-term domain (414-575 aa)
DEAD box motif (347-350 aa)
MAPK1 Chr. 22q11.21
p.D162N
p.D291G
p.Y316F
361 aa
Protein Kinase Domain
Protein Kinase Domain (25-313 aa)
GNB1 Chr. 1 p36.33
p.I80T (x2)
341 aa
WD1
WD2
WD3
WD4
WD5
WD6
WD7
WD1 = (53-93 aa)
WD2 = (95-125 aa)
WD3 = (141-170 aa)
WD4 = (182-212 aa)
WD5 = (224-254 aa)
WD6 = (268-298 aa)
WD6 = (310-341 aa)

SF3B1 expression is high in CLL cells

COMPOSITIONS AND METHODS OF IDENTIFYING TUMOR SPECIFIC NEOANTIGENS

RELATED APPLICATIONS

This application is a continuation of U.S. application Ser. No. 15/187,174, filed on Jun. 20, 2016, which is divisional of U.S. application Ser. No. 14/794,449 filed Jul. 8, 2015, which is a divisional of U.S. application Ser. No. 13/108,610 filed May 16, 2011, and which claims the benefits of U.S. provisional application No. 61/334,866, filed May 14, 2010, which is incorporated herein by reference in its entirety.

INCORPORATION-BY-REFERENCE OF SEQUENCE LISTING

The contents of the text file name "BIS-70701_ST25.txt", which was created on Jul. 19, 2011 and is 73 KB in size, are hereby incorporated by reference it their entirety.

FIELD OF THE INVENTION

The present invention relates generally to the identification of tumor specific neoantigens and the uses of these neoantigens to produce cancer vaccines.

BACKGROUND OF THE INVENTION

Tumor vaccines are typically composed of tumor antigens and immunostimulatory molecules (e.g. cytokines or TLR ligands) that work together to induce antigen-specific cytotoxic T cells (CTLs) that recognize and lyse tumor cells. At this time, almost all vaccines contain either shared tumor antigens or whole tumor cell preparations (Gilboa, 1999). The shared tumor antigens are immunogenic proteins with selective expression in tumors across many individuals and are commonly delivered to patients as synthetic peptides or recombinant proteins (Boon et al., 2006). In contrast, whole tumor cell preparations are delivered to patients as autologous irradiated cells, cell lysates, cell fusions, heat-shock protein preparations or total mRNA (Parmiani et al., 2007). Since whole tumor cells are isolated from the autologous patient, the cells express patient-specific tumor antigens as well as shared tumor antigens. Finally, there is a third class of tumor antigens that has rarely been used in vaccines due to technical difficulties in identifying them (Sensi et al. 2006). This class consists of proteins with tumor-specific mutations that result in altered amino acid sequences. Such mutated proteins have the potential to: (a) uniquely mark a tumor (relative to non-tumor cells) for recognition and destruction by the immune system (Lennerz et al., 2005); (b) avoid central and sometimes peripheral T cell tolerance, and thus be recognized by more effective, high avidity T cells receptors (Gotter et al., 2004).

Thus a need exists for a method of identifying neoepitopes that are useful as tumor vaccines.

SUMMARY OF THE INVENTION

The present invention relates in part to the discovery of a method of identifying peptides that are capable of elicting a tumor specific T-cell response.

In one aspect the invention provides methods of identifying a neoantigen by identifying a tumor specific mutation in an expressed gene of a subject having cancer. In some aspects when the mutation is a point mutation the method further comprises identifying the mutant peptide having the mutation. Preferably the mutant peptide binds to a class I HLA protein with a greater affinity than a wild-type peptide and has an IC50 less than 500 nm; In other aspects when the mutation is a splice-site, frameshift, read-through or gene-fusion mutation the method further comprise identifying the mutant polypeptide encoded by the mutation. Preferably, the mutant polypeptide binds to a class I HLA protein.

Optionally, the method further includes selecting peptides or polypeptides that activate anti-tumor CD8 T cells.

The mutant peptide or polypeptide preferably binds to a class I HLA protein with a greater affinity than a wild-type peptide and has an IC50 less than 500 nM. Preferably, the peptide or polypeptide has an IC50 less than 250 nM. More preferably, the peptide or polypeptide has an IC50 less than 100 nM. Most preferably, the peptide or polypeptide has an IC50 less than 50 nM.

The mutant peptide is about 8-10 amino acids in length. In another aspect is about 8-50 amino acids in length. For example, mutant peptide is greater than 10 amino acids in length, greater than 15 amino acids in length, greater than 20 amino acids in length, greater than 30 amino acids in length. Preferably the the mutant peptides is about 24-40 amino acids in length.

In a further aspect the invention provides methods of inducing a tumor specific immune response in a subject by administering one or more peptides or polypeptides identified according to the methods of the invention and an adjuvant. The adjuvant is for example, a TLR-based adjuvant or a mineral oil based adjuvant. In some aspects the peptide or polypeptide and TLR-based adjuvant is emulsified with a mineral oil based adjuvant. Optionally, the method further includes administering an anti-immunosuppressive agent such as an anti-CTLA-4 antibody, an anti-PD1 antibody an anti-PD-L1 antibody an anti-CD25 antibody or an inhibitor of IDO.

In yet another aspect the invention provides methods of inducing a tumor specific immune response in a subject by administering to the subject autologous dendritic cells or antigen presenting cells that have been pulsed with one or more of the peptides or polypeptides identified according to the methods of the inventions. Optionally, the method further includes administering an adjuvant such as for example, a TLR-based adjuvant or a mineral oil based adjuvant. In some aspects the peptide or polypeptide and TLR-based adjuvant is emulsified with a mineral oil based adjuvant. In some embodiments the method further includes administering an anti-immunosuppressive agent. Anti-immunosuppressive agents include for example an anti-CTLA-4 antibody, an anti-PD1 antibody an anti-PD-L1 antibody an anti-CD25 antibody or an inhibitor of IDO.

In another aspect the invention provides a method of vaccinating or treating a subject for cancer by identifying a plurality of tumor specific mutations in an expressed gene of the subject, identifying mutant peptides or polypeptides having the identified tumor specific mutations, selecting one or more of the identified mutant peptide or polypeptides that binds to a class I HLA protein preferably with a greater affinity than a wild-type peptide and is capable of activating anti-tumor CD8 T-cells, and administering to the subject the one or more selected peptides, polypeptides or autologous dendritic cells or antigen presenting cells pulsed with the one or more identified peptides or polypeptides. The mutant peptide is about 8-10 amino acids in length. In another aspect is about 8-50 amino acids in length. For example, mutant peptide is greater than 10 amino acids in length, greater than 15 amino acids in length, greater than 20 amino acids in length, greater than 30 amino acids in length. Preferably, the mutant peptides is about 24-40 amino acids in length.

Optionally, the method further includes administering an adjuvant such as for example, a TLR-based adjuvant or a mineral oil based adjuvant. In some aspects the peptide or polypeptide and TLR-based adjuvant is emulsified with a mineral oil based adjuvant. In some embodiments the method further includes administering an anti-immunosuppressive agent. Anti-immunosuppressive agents include for example an anti-CTLA-4 antibody, an anti-PD1 antibody an anti-PD-L1 antibody an anti-CD25 antibody or an inhibitor of IDO.

The subject is a human, dog, cat, or horse. The cancer is breast cancer, ovarian cancer, prostate cancer, lung cancer, kidney cancer, gastric cancer, colon cancer, testicular cancer, head and neck cancer, pancreatic cancer, brain cancer, melanoma lymphoma, such as B-cell lumphoma or leukemia, such as cute myelogenous leukemia, chronic myelogenous leukemia, chronic lymphocytic leukemia, or T cell lymphocytic leukemia.

Also included in the invention are pharmaceutical compositions containing the peptide or polypeptide identified according the methods of the invention and a pharmaceutically acceptable carrier.

For example, the invention provides a composition containing least two distinct SF3B1 peptides wherein each peptide is equal to or less than 50 amino acids in length and contains a leucine at amino acid position 625;
a histidine at amino acid position 626;
a glutamic acid at amino acid position 700;
an aspartic acid at amino acid position 742; or
an arginine at amino acid position 903, when numbered in accordance with wild-type SF3B1.

The invention also provides a composition containing at least two distinct MYD88 peptides where each peptide is equal to or less than 50 amino acids in length and contains a threonine at amino acid position 232; a leucine at amino acid position 258; or a proline at amino acid position 265, when numbered in accordance with wild-type MYD88

The invention further provides composition containing at least two distinct TP53 peptides where each peptide is equal to or less than 50 amino acids in length and contains an arginine at amino acid position 111; an arginine at amino acid position 215; a serine at amino acid position 238; a glutamine at amino acid position 248; a phenylalanine at amino acid position 255; a cysteine at amino acid position 273 or an asparagine at amino acid position 281, when numbered in accordance with wild-type TP53.

The invention further provides composition containing at least two distinct ATM peptides wherein each peptide is equal to or less than 50 amino acids in length and contain a phenylalanine at amino acid position 1252; an arginine at amino acid position 2038; a histidine at amino acid position 2522; or a cysteine at amino acid position 2954, when numbered in accordance with wild-type ATM.

A composition comprising at least two distinct Abl peptides wherein each peptide is equal to or less than 50 amino acids in length and contains a valine at amino acid position 244; a valine at amino acid position 248;
a glutamic acid at amino acid position 250; an alanine at amino acid position 250; a histidine at amino acid position 252; an arginine at amino acid position 252; a phenylalanine at amino acid position 253; a histidine at amino acid position 253; a lysine at amino acid position 255; a valine at amino acid position 255; a glycine at amino acid position 276; an isoleucine at amino acid position 315; an asparagine at amino acid position 315; a leucine at amino acid position 317; a threonine at amino acid position 343; a threonine at amino acid position 351; a glycine at amino acid position 355; a valine at amino acid position 359; an alanine at amino acid position 359; an isoleucine at amino acid position 379; a leucine at amino acid position 382; a methionine at amino acid position 387; a proline at amino acid position 396; an arginine at amino acid position 396; a tyrosine at amino acid position 417; or a serine at amino acid position 486, when numbered in accordance with wild-type ABL.

Further included in the invention is a composition containing at least two distinct FBXW7 peptides where each peptide is equal to or less than 50 amino acids in length and contains a leucine at amino acid position 280; a histidine at amino acid position 465; a cysteine at amino acid position 505; or a glutamic acid at amino acid position 597, when numbered in accordance with wild-type FBXW7.

In a further a aspect the invention provides a composition containing at least two distinct MAPK1 peptides where each peptide is equal to or less than 50 amino acids in length and contains an asparagine at amino acid position 162; a glycine at amino acid position 291; or a phenylalanine at amino acid position 316, when numbered in accordance with wild-type MAPK1.

The invention also provides a composition containing at least two distinct GNB1 peptides wherein each peptide is equal to or less than 50 amino acids in length and contains a threonine at amino acid position 180, when numbered in accordance with wild-type GNB1.

Also provided by the invention is a method of treating a subject with an imatinib resistant tumor to a HLA-A3 positive subject a composition of Bcr-abl peptide equal to or less than 50 amino acid in length that contains a lysine at position 255 when numbered in accordance with wild-type bcr-abl.

Further provided by the invention, is method of treating a subject with an imatinib resistant tumor comprising administering to the subject one or more peptides containing a bcr-abl mutation where the peptide is equal to or less than 50 amino acid and binds to a class I HLA protein with an IC50 less than 500 nm.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

Overexpressed tumor antigens are slightly more specific because they have been selected for much higher and more selective expression in tumors compared to other cells in the body. Nevertheless, it is impossible to test every cell in the body for the expression of these antigens and there is a substantial risk that other cells express them. Finally, mutated proteins generate neoepitopes that are present only in tumor cells and provide the greatest level of specificity.

Figure 2:
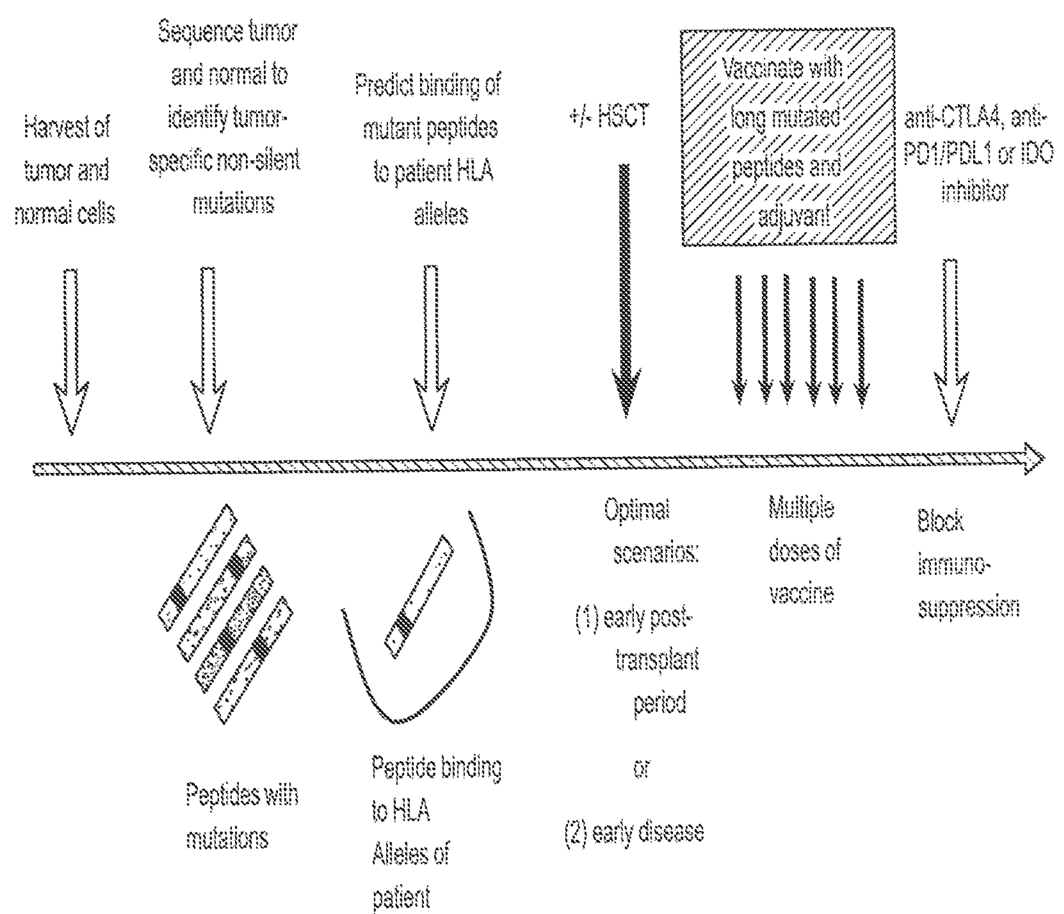

FIG. 2 is a schema for a personalized neoantigen vaccination strategy that can be applied to the treatment of any cancer. We also highlight the possibility of applying this strategy in two unique scenarios. In the first case, a patient is vaccinated in the early period following hematopoietic stem cell transplantation (HSCT) (e.g. as is done for CLL, CML and other leukemias). The early post-HSCT period is a unique therapeutic setting as the immune system is competent due to reconstitution with HSCT, thus overcoming tumor- or treatment-induced host immune defects. Moreover, the abundance of homeostatic cytokines in a lymphopenia milieu, such as in the early post-HSCT setting, can contribute to rapid expansion of T cells. In the second case, a patient is vaccinated early in the disease course when immune competence may be more intact in the early stages of disease, before impairment by exposure to chemotherapy (e.g. for solid or hematopoeitic tumors). Since the immune system is likely to be most active in these two specific situations, we suggest that these are the ideal situations for applying tumor vaccination strategies.

Figure 3:
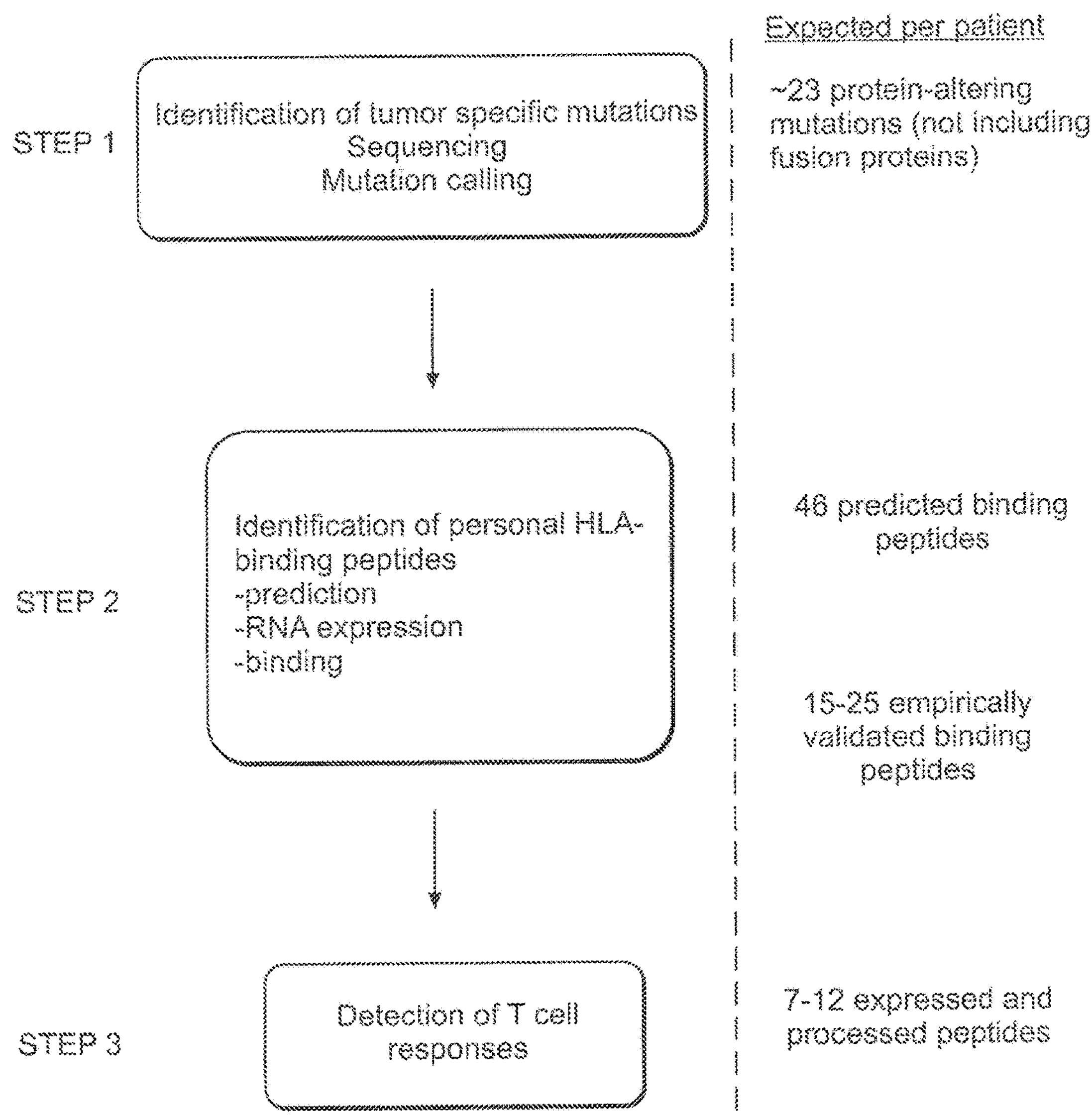

FIG. 3 shows a strategy for identifying tumor neoepitopes is described in 3 steps: (1) using sequencing technologies, detect gene mutations that are present in tumor but not germline DNA of a single patient; (2) using prediction algorithms, predict whether mutated peptides have the potential to bind personal HLA allele; these predicted peptides may optionally be tested experimentally for binding to appropriate HLA proteins. In addition, these genes must also be expressed in tumor cells. (3) generate T cells ex vivo and test whether they are able to recognize cells expressing the mutated protein; alternatively, mass spectrometry can be used to detect peptides eluted from tumor cell surface HLA proteins. For chronic lymphocytic leukemia, our studies to date demonstrate that there are an average of 23 protein-altering mutations per patient, 46 predicted binding mutant peptides and 15-25 validated binding mutant peptides. Of these, we anticipate that ~7-12 peptides are expressed and processed in tumor cells (though this may differ across tumors and patients).

FIG. 4 shows five classes of mutations generate potential tumor neoepitopes. New tumor-specific epitopes can arise as a result of missense, splice-site, frameshift or read-through point mutations (red asterisk), or from the fusion of two genes (or within the same gene). In particular, splice-site, frameshift, read-through mutations and gene fusions can each generate novel stretches of amino acids (in magenta) that are normally not translated, but now are expressed and translated as a result of mutation. Missense mutations lead to peptides with single amino acid changes.

Figure 5:
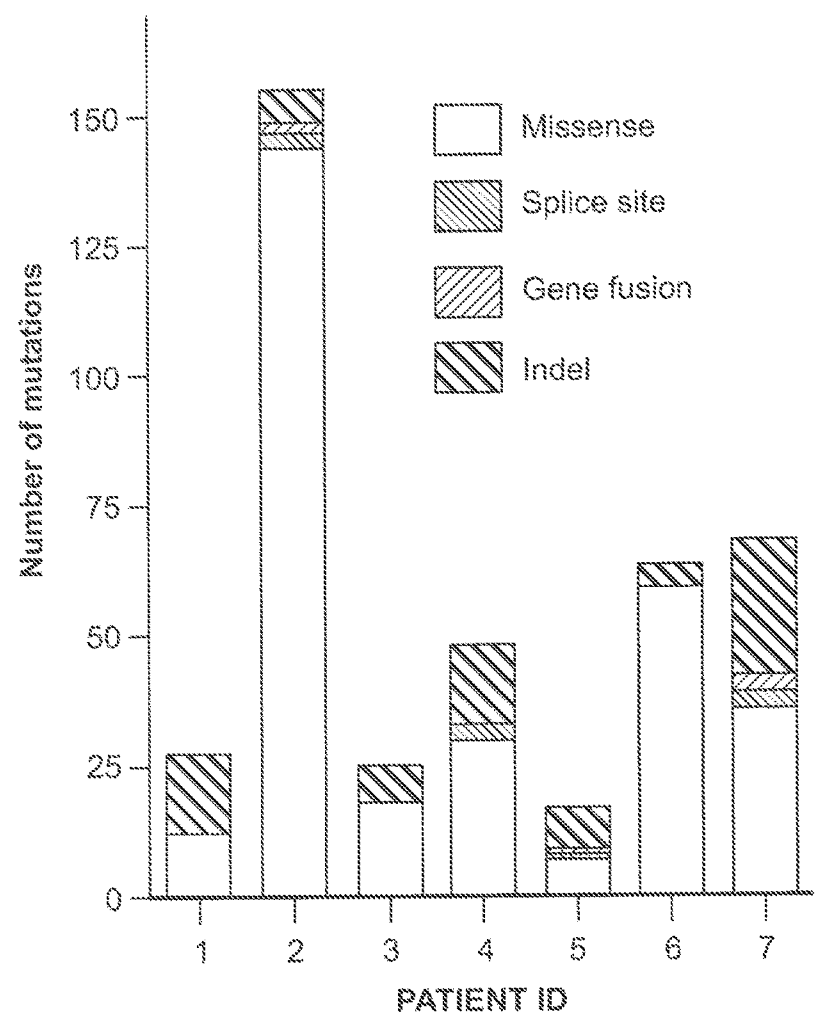

FIG. 5 shows the frequency of mutations per class in CLL patients. Our studies applying next-generation sequencing to a series of 7 CLL tumors reveal that CLL cells harbor many mutations that provide a rich source of possible mutated peptides. We observe that the total number of nonsilent gene alterations in CLL ranged from 17-155 per individual, the majority of which were somatically altered point mutations (missense). The tumors of 4 patients also harbored splice-site mutations; for 3 patients, novel gene fusions were identified by RNA sequencing.

FIG. 6 shows data from automated predictions (Step 2A of the strategy in FIG. 3) of peptide binding (for peptides that harbor a specific missense mutation) against each of a patient's 6 HLA (MHC Class I) alleles. Magenta=strong binders; green=intermediate binders.

Figure 7:
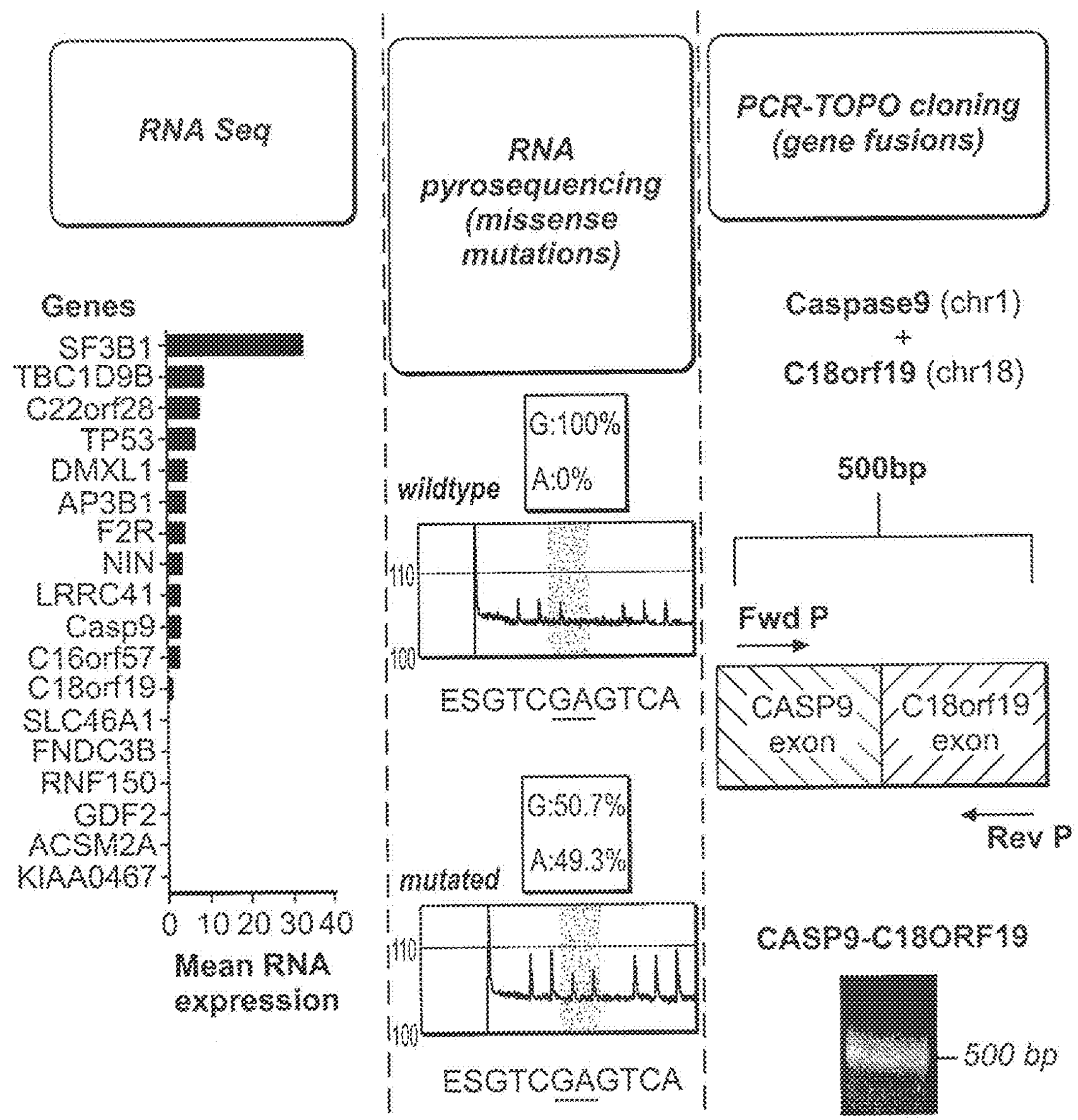

FIG. 7 shows methods for confirming RNA expression of mutated genes (Step 2B of the strategy in FIG. 3). A. For CLL patient 7, we found that more than half of the mutated genes with predicted HLA-binding peptides were expressed at the RNA level. B. We have also used RNA pyrosequencing to detect expressed RNAs harboring specific mutations found in DNA. C. We can validate novel gene fusions that were seen by DNA sequencing using PCR-TOPO cloning of the breakpoint region (depicted is a fusion discovered for patient 2).

FIG. 8A-8C shows a method and data for experimental validation of HLA-peptide binding (Step 2C of the strategy in FIG. 3). A. Schema for experimental validation of peptide binding to specific HLA alleles. B. Summary of candidate mutated peptides identified in patients 1 and 2. Shaded cells indicate that analysis is in progress. C. Data for predicted vs experimentally verified binding affinity of peptides generated from gene alterations (missense mutation or gene fusion) for patient 2. A prediction cutoff of $IC_{50}$<120 nM (solid vertical line on left) results in all peptides showing experimental binding to class I HLA.

Figure 9:
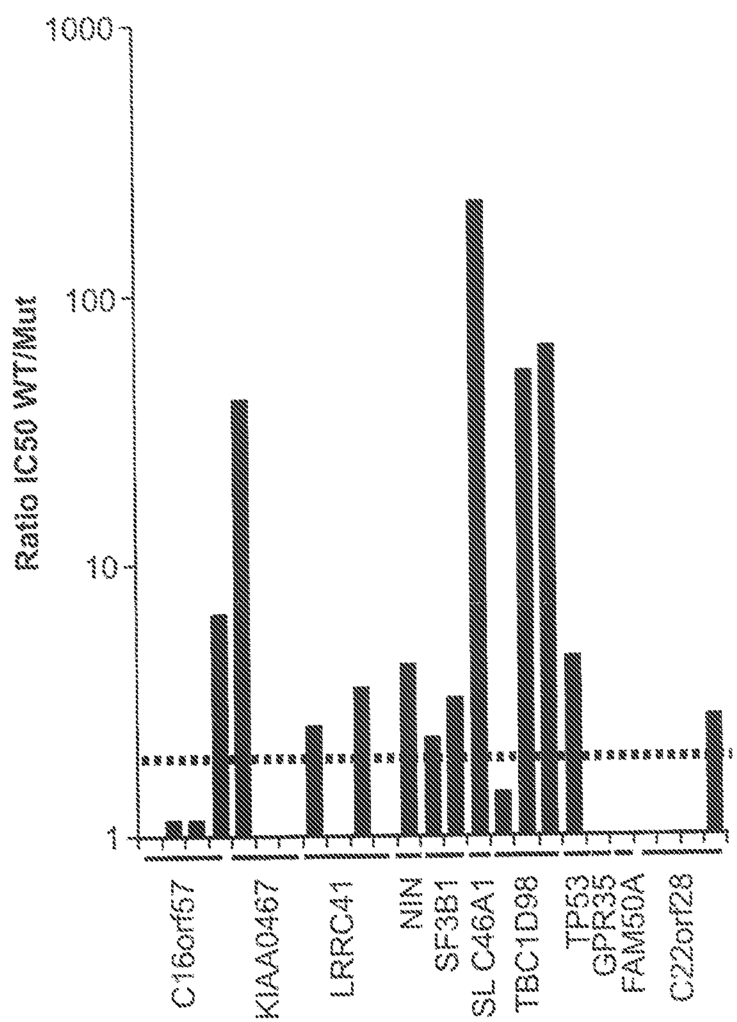

FIG. 9 shows predicted differential binding of mutated vs germline (i.e also called parental, wild type or normal) peptides to HLA alleles. 12 of 25 predicted HLA binding mutated peptides of Pt 2 have >2 fold greater binding (cutoff=red dotted line) than parental peptides. This further increases the specificity of mutated peptides. Mutated peptides are specific for two reasons: first, many of the T cell receptors that recognize a mutated peptide are not likely to detect the wild type parental peptide; second, some of the mutated peptides can bind HLA with higher affinity than the parental peptide. Since the first property cannot be computationally predicted, we will focus on predicting the second property and selecting for inclusion in vaccines only those peptides that show higher binding to HLA for mutated relative to wild type peptides.

Figure 10:
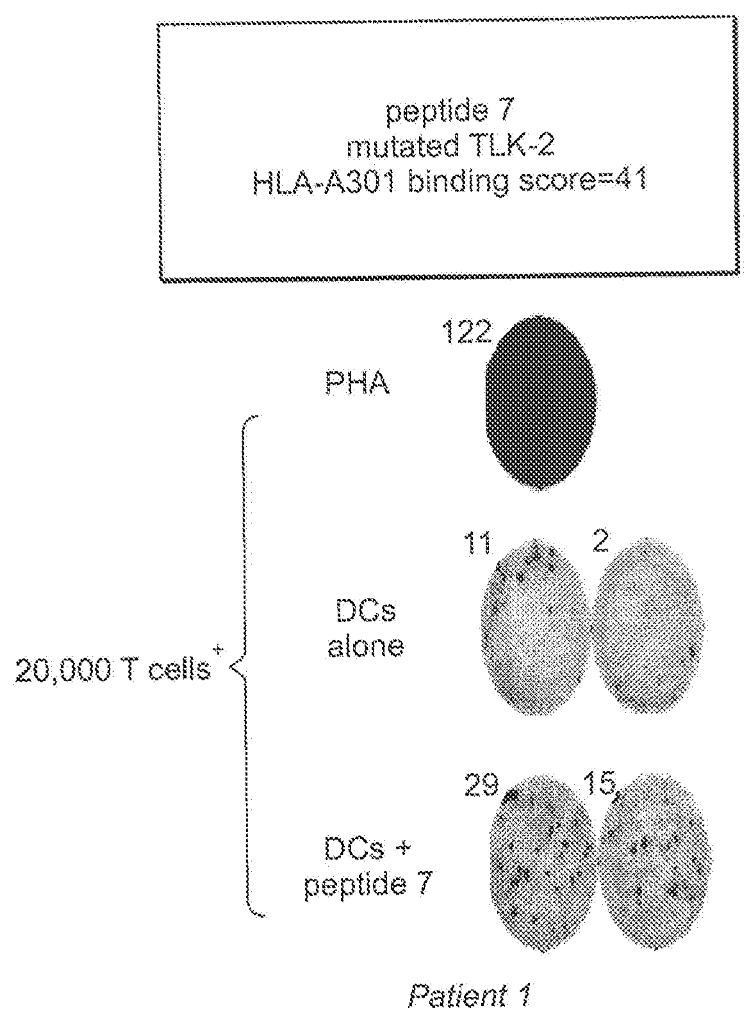

FIG. 10 shows T cell reactivity against a candidate personal CLL neoepitope (Step 3 of the strategy in FIG. 3). We observed that T cells isolated from patient 1 post-therapy can detect a specific mutated TLK2 peptide (peptide #7) (using the Elispot assay).

FIG. 11 shows that BCR-ABL mutations generate many peptides predicted to bind HLA-A and HLA-B alleles. By applying the NetMHC prediction algorithm (Nielsen et al. PLoS One. 2007, 2(8):e796), we predicted peptides generated from the BCR-ABL mutations with potential to bind to 8 common HLA-A and -B alleles. The most common BCR-ABL mutations are ordered in decreasing frequency (from left to right), and predicted IC50 of various class I MHC binding peptides are depicted. In total, we predicted 84 peptides to bind with good affinity, defined as an IC50 of less than 1000, across a wide range of HLA alleles. Of all the predicted peptides, 24 of 84 (29%) were predicted to be strong binders with an IC50<50. 42 peptides (50%) were intermediate binders, defined as IC50 between 50 and 500. 18 peptides (21%) were weak binders defined as IC50 between 500 and 1000.

FIG. 12A-12D shows BCR-ABL peptide harboring the E255K mutation binds HLA proteins and is associated with specific, polyfunctional T cells present in CIVIL patients. A. Experimentally-derived binding scores of E255K-B (and parental peptide) to HLA A3 and supertype members. B. In CD8+ T cells expanded from a HLAA3+ E255K+patient following HSCT, we detected IFNgamma secretion against the E255K-B (MUT) peptide and A3+ expressing APCs expressing the E255K minigene (MG). This response was abrogated in the presence of the class I blocking antibody (w6/32). C. IFNgamma-secreting cells were also tetramer+ for the mutated peptide and were (D) polyfunctional, secreting IP10, TNFalpha and GM-CSF (based on the Luminex assay).

FIG. 13A-13C shows that patient-derived T cell clones can recognize tumor-specific epitopes and kill cells presenting these epitopes. A. Reactivity to the CD8+ T cell epitope of CML66 (peptide 66-72C) is restricted by HLA B-4403. B. CML66 mRNA can be efficiently nucleofected into CD40L-expanded B cells. C. CML66-specific CD8+ T cells are cytotoxic to CD40L B cells expressing CML66 by RNA nucleofection or by peptide pulse, but not control targets.

FIG. 14A-14C shows significantly mutated genes in CLL. A. The 9 most significantly mutated genes among 64 CLL samples. N—total covered territory in base pairs across 64 sequenced samples. p- and q-values were calculated by comparing the probability of seeing the observed constellation of mutations to the background mutation rates calculated across the dataset. Red bars—genes not previously known to be mutated in CLL; grey bars—genes in which mutation in CLL has been previously reported. B-C. Type (missense, splice-site, nonsense) and location of mutations in ATM, SF3B1, TP53, MYD88, FBXW7, DDX3X, MAPK1, and GNB1 discovered among the 64 CLLs (position and mutation in CLL samples shown above the gene) compared to previously reported mutations in literature or in the COSMIC database (lines show position of mutations below the gene).

Figure 15:
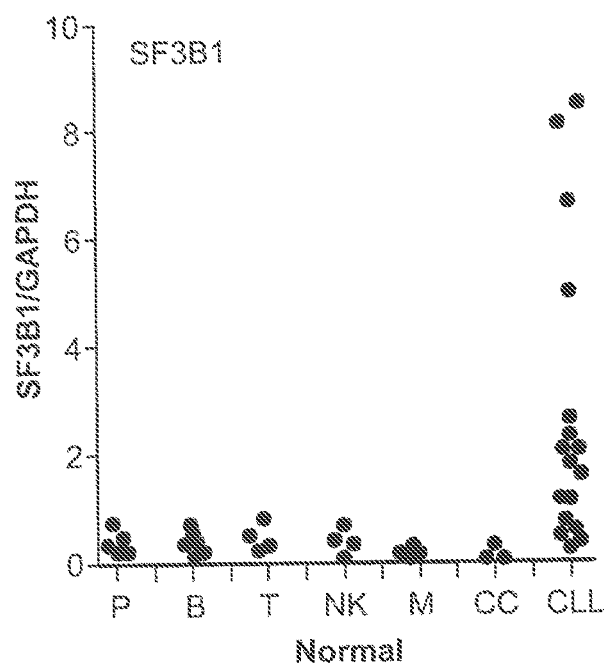

FIG. 15 shows that SF3B1 is expressed in CLL samples (7th column in graph) and has higher expression than many control cells, including: PBMC, M: monocyte, CC: cancer cell lines (includes K562, Jurkat, IM9, MCF-7, Hela, Ovcar, RPMI, OTM, MCF-CAR, KM12BM and MM1S).

Figure 16:
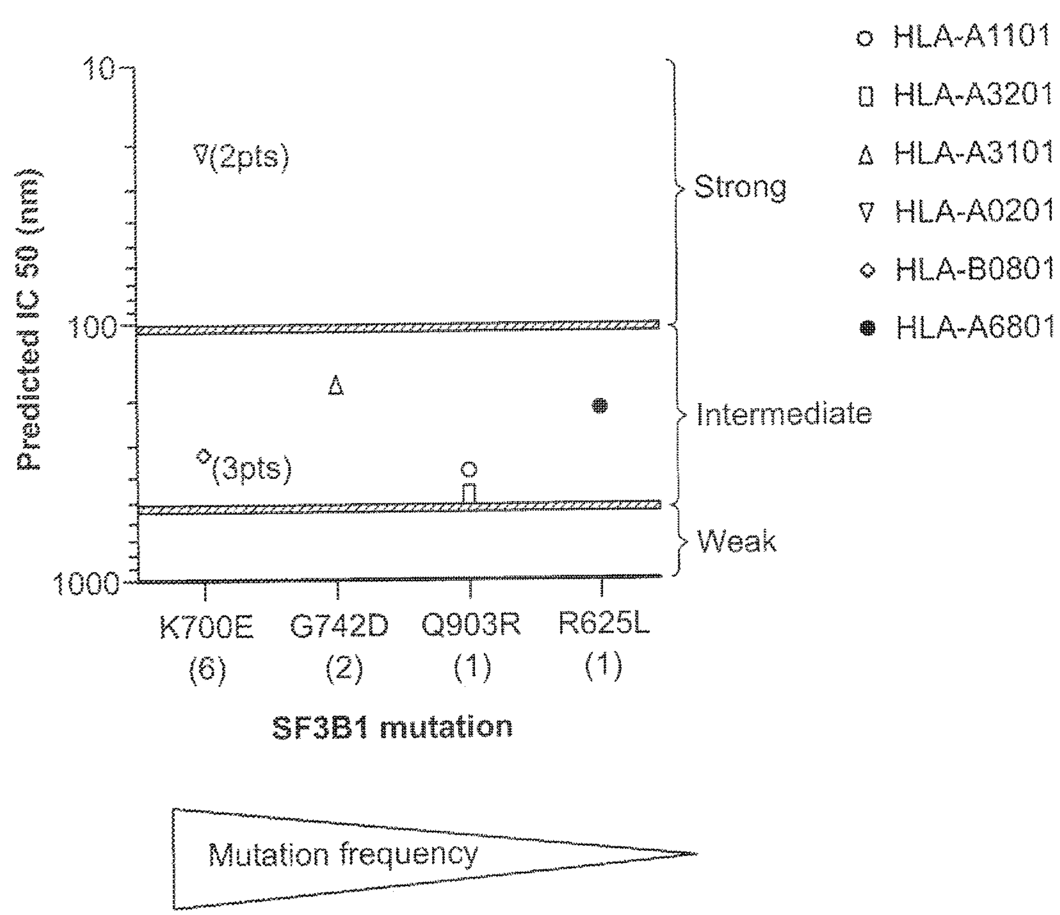

FIG. 16 shows that SF3B1 mutations generate peptides that are predicted to bind to patient-specific HLA alleles. For example, one peptide that includes the common SF3B1 K700E mutation is predicted to bind HLA strongly.

DETAILED DESCRIPTION OF THE INVENTION

One of the critical barriers to developing curative and tumor-specific immunotherapy is the identification and selection of highly restricted tumor antigens to avoid autoimmunity. Tumor neoantigens, which arise as a result of genetic change within malignant cells, represent the most tumor-specific class of antigens. Neoantigens have rarely been used in vaccines due to technical difficulties in identifying them. Our approach to identify tumor-specific neoepitopes involves three steps. (1) identification of DNA mutations using whole genome or whole exome (i.e. only captured exons) or RNA sequencing of tumor versus matched germline samples from each patient; (2) application of validated peptide-MHC binding prediction algorithms to generate a set of candidate T cell epitopes that may bind patient HLA alleles and are based on non-silent mutations present in tumors; and (3) optional demonstration of antigen-specific T cells against mutated peptides or demonstration that a candidate peptide is bound to HLA proteins on the tumor surface.

Accordingly, the present invention relates to methods for identifying and/or detecting T-cell epitopes of an antigen. Specifically, the invention provides method of identifying and/or detecting tumor specific neoantigens that are useful in inducing a tumor specific immune response in a subject.

In particular, the invention provides a method of vaccinating or treating a subject by identifying a plurality of tumor specific mutations in the genome of a subject. Mutant peptides and polypeptides having the identified mutations and that binds to a class I HLA protein are selected. Optionally, these peptide and polypeptides binds to a class I HLA proteins with a greater affinity than the wild-type peptide and/or are capable of activating anti-tumor CD8 T-cells These peptides are administered to the subject. Alternatively, autologous antigen-presenting cells that have been pulsed with the peptides are administered.

Figure 1:
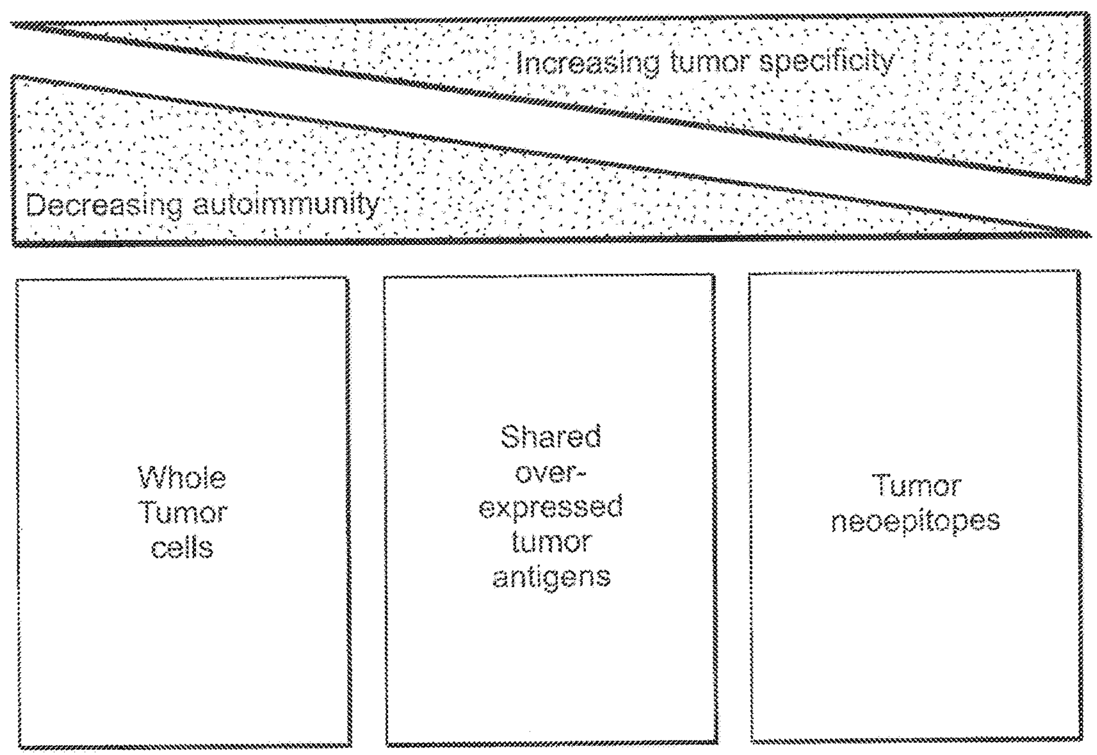
FIG. 1 shows the balance of specificity and autoimmune toxicity using 3 classes of antigens for tumor vaccines. Whole tumor cells may be the the least specific antigen formulation for tumor vaccines since the full set of protein antigens expressed in tumor cells include thousands of proteins that are also present in other cells of the body.

The importance of mutated antigens, or neoepitopes, in the immune control of tumors has been appreciated in seminal studies showing that: (a) mice and humans often mount T cell responses to mutated antigens (Parmiani et al., 2007; Sensi and Anichini, 2006); (b) mice can be protected from a tumor by immunization with a single mutated peptide that is present in the tumor (Mandelboim et al., 1995); (c) spontaneous or vaccine-mediated long-term melanoma survivors mount strong memory cytotoxic T cell (CTL) responses to mutated antigens (Huang et al., 2004; Lennerz et al., 2005; Zhou et al., 2005a); (d) finally, follicular lymphoma patients show molecular remission when immunized with patient-specific mutated immunoglobulin proteins that are present in autologous tumor cells. (Baskar et al., 2004). Furthermore, the CTL responses in these patients are directed toward the mutated rather than shared regions of the immunoglobulin protein. Additionally, such mutated peptides have the potential to: (a) uniquely mark a tumor for recognition and destruction by the immune system, thus reducing the risk for autoimmunity; and (b) avoid central and peripheral T cell tolerance, allowing the antigen to be recognized by more effective, high avidity T cells receptors. (FIG. 1)

Identical mutations in any particular gene are rarely found across tumors (and are even at low frequency for the most common driver mutations). Thus, the methods of the present invention will comprehensively identify patient-specific tumor mutations. Using highly parallel sequencing technologies, HLA-peptide binding prediction tools and biochemical assays the methods of the invention will allow: (1) comprehensive identification of mutated peptides that are expressed and bind HLA proteins present in a patient's tumor; (2) monitoring of the natural immune response of cancer patients to these identified neoepitopes; (3) determining whether cytotoxic T cells that recognize these peptides in the context of patient HLA proteins can selectively lyse autologous tumor cells ex vivo. This strategy addresses several fundamental questions related to how the immune system of cancer patients interacts with tumor neoepitopes. These include: which and what fraction of tumor neoepitopes are detected by T cells, how many T cell precursors are able to respond to neoepitopes, how frequent are neoepitope-specific memory and effector T cells in circulation and in the tumor, how much avidity do T cells have for these epitopes, are neoepitope-specific T cells functional? The answers to these questions provide both the justification and strategy for using tumor neoepitopes in human vaccines.

The immune system of a human can be classified into two functional subsystems, i.e., the innate and the acquired immune system. The innate immune system is the first line of defense against infections, and most potential pathogens are rapidly neutralized before they can cause, for example, a noticeable infection. The acquired immune system reacts to molecular structures, referred to as antigens, of the intruding organism. There are two types of acquired immune reactions, i.e. the humoral immune reaction and the cell-mediated immune reaction. In the humoral immune reaction, the antibodies secreted by B cells into bodily fluids bind to pathogen-derived antigens, leading to the elimination of the pathogen through a variety of mechanisms, e.g. complement-mediated lysis. In the cell-mediated immune reaction, T-cells capable of destroying other cells are activated. If, for example, proteins associated with a disease are present in a cell, they are, within the cell, fragmented proteolytically to peptides. Specific cell proteins then attach themselves to the antigen or peptide formed in this manner and transport them to the surface of the cell, where they are presented to the molecular defense mechanisms, in particular T-cells, of the body. Cytotoxic T cells recognize these antigens and kill the cells that harbor the antigens.

The molecules which transport and present peptides on the cell surface are referred to as proteins of the major histocompatibility complex (MHC). The MHC proteins are classified into MHC proteins of class I and of class II. The structures of the proteins of the two MHC classes are very similar; however, they differ quite considerably in their function. Proteins of MHC class I are present on the surface of almost all cells of the body, including most tumor cells. The proteins of MHC class I are loaded with antigens that usually originate from endogenous proteins or from pathogens present inside cells, and are then presented to cytotoxic T-lymphocytes (CTLs). The MHC proteins of class II are only present on dendritic cells, B-lymphocytes, macrophages and other antigen-presenting cells. They present mainly peptides, which are processed from external antigen sources, i.e. outside of the cells, to T-helper (Th) cells. Most of the peptides bound by the MHC proteins of class I originate from cytoplasmic proteins produced in the healthy host organism itself and don't normally stimulate an immune reaction. Accordingly, cytotoxic T-lymphocytes which recognize such self-peptide-presenting MHC molecules of class I are deleted in the thymus or, after their release from the thymus, are deleted or inactivated, i.e. tolerized. MHC molecules are only capable of stimulating an immune reaction when they present peptides to non-tolerized cytotoxic T-lymphocytes. Cytotoxic T-lymphocytes have, on their surface, both T-cell receptors (TCR) and CD8 molecules. T-Cell receptors are capable of recognizing and binding peptides complexed with the molecules of MHC class I. Each cytotoxic T-lymphocyte expresses a unique T-cell receptor which is capable of binding specific MHC/peptide complexes.

The peptides attach themselves to the molecules of MHC class I by competitive affinity binding within the endoplasmic reticulum, before they are presented on the cell surface. Here, the affinity of an individual peptide is directly linked to its amino acid sequence and the presence of specific binding motifs in defined positions within the amino acid sequence. If the sequence of such a peptide is known, it is possible, for example, to manipulate the immune system against diseased cells using, for example, peptide vaccines.

Using computer algorithms, it is possible to predict potential T-cell epitopes, i.e. peptide sequences, which are bound by the MHC molecules of class I or class II in the form of a peptide-presenting complex and then, in this form, recognized by the T-cell receptors of T-lymphocytes. Currently, use is made, in particular, of two programs, namely SYFPEITHI (Rammensee et al., Immunogenetics, 50 (1999), 213-219) and HLA_BIND (Parker et al., J. Immunol., 152 (1994), 163-175). The peptide sequences determined in this manner, which potentially may bind to MHC molecules of class I, then have to be examined in vitro for their actual binding capacity.

The technical object of the present invention is to provide an improved method for identifying and screening potential T-cell epitopes present in tumor cells, which method allows for simultaneous and rapid examination of a large number of peptide sequences, for their capability of binding to specific MHC molecules.

In the present invention, the technical object on which it is based is achieved by providing a method for identifying and/or detecting mutated antigens that are present in tumors but not in normal tissue. The method uses massively parallel genomic sequencing of the entire coding portion of a cancer patient genome to identify the specific mutated genes in a tumor. In order to narrow down the mutant peptides to those with potential to bind more strongly to HLA than the wild type peptides and thus confer tumor specificity, well-established algorithms will be used to predict peptides that bind any of the 6 unique class I HLA alleles of each patient and a predicted IC50 for all 9- or 10-mer peptides with tumor-specific mutant residues vs. those with the germline residue will be calculated. Typically, peptides with predicted IC50<50 nM, are generally considered medium to high affinity binding peptides and will be selected for testing their affinity empirically using biochemical assays of HLA-binding. Finally, it will be determined whether the human immune system can mount effective immune responses against these mutated tumor antigens and thus effectively kill tumor but not normal cells.

Definitions

A "T-cell epitope" is to be understood as meaning a peptide sequence which can be bound by the MHC molecules of class I or II in the form of a peptide-presenting MHC molecule or MHC complex and then, in this form, be recognized and bound by cytotoxic T-lymphocytes or T-helper cells, respectively A "receptor" is to be understood as meaning a biological molecule or a molecule grouping capable of binding a ligand. A receptor may serve, to transmit information in a cell, a cell formation or an organism. The receptor comprises at least one receptor unit and preferably two receptor units, where each receptor unit may consist of a protein molecule, in particular a glycoprotein molecule. The receptor has a structure which complements that of a ligand and may complex the ligand as a binding partner. The information is transmitted in particular by conformational changes of the receptor following complexation of the ligand on the surface of a cell. According to the invention, a receptor is to be understood as meaning in particular proteins of MHC classes I and II capable of forming a receptor/ligand complex with a ligand, in particular a peptide or peptide fragment of suitable length.

A "ligand" is to be understood as meaning a molecule which has a structure complementary to that of a receptor and is capable of forming a complex with this receptor. According to the invention, a ligand is to be understood as meaning in particular a peptide or peptide fragment which has a suitable length and suitable binding motives in its amino acid sequence, so that the peptide or peptide fragment is capable of forming a complex with proteins of MHC class I or MHC class II.

A "receptor/ligand complex" is also to be understood as meaning a "receptor/peptide complex" or "receptor/peptide fragment complex", in particular a peptide- or peptide fragment-presenting MHC molecule of class I or of class II.

"Proteins or molecules of the major histocompatibility complex (MHC)", "MHC molecules", "MHC proteins" or "HLA proteins" are to be understood as meaning, in particular, proteins capable of binding peptides resulting from the proteolytic cleavage of protein antigens and representing potential T-cell epitopes, transporting them to the cell surface and presenting them there to specific cells, in particular cytotoxic T-lymphocytes or T-helper cells. The major histocompatibility complex in the genome comprises the genetic region whose gene products expressed on the cell surface are important for bindung and presenting endogenous and/or foreign antigens and thus for regulating immunological processes. The major histocompatibility complex is classified into two gene groups coding for different proteins, namely molecules of MHC class I and molecules of MHC class II. The molecules of the two MHC classes are specialized for different antigen sources. The molecules of MHC class I present endogenously synthesized antigens, for example viral proteins and tumor antigens. The molecules of MHC class II present protein antigens originating from exogenous sources, for example bacterial products. The cellular biology and the expression patterns of the two MHC classes are adapted to these different roles.

MHC molecules of class I consist of a heavy chain and a light chain and are capable of binding a peptide of about 8 to 11 amino acids, but usually 9 or 10 amino acids, if this peptide has suitable binding motifs, and presenting it to cytotoxic T-lymphocytes. The peptide bound by the MHC molecules of class I originates from an endogenous protein antigen. The heavy chain of the MHC molecules of class I is preferably an HLA-A, HLA-B or HLA-C monomer, and the light chain is β-2-microglobulin.

MHC molecules of class II consist of an α-chain and a β-chain and are capable of binding a peptide of about 15 to 24 amino acids if this peptide has suitable binding motifs, and presenting it to T-helper cells. The peptide bound by the MHC molecules of class II usually originates from an extracellular of exogenous protein antigen. The α-chain and the β-chain are in particular HLA-DR, HLA-DQ and HLA-DP monomers.

A "vaccine" is to be understood as meaning a composition for generating immunity for the prophylaxis and/or treatment of diseases. Accordingly, vaccines are medicaments which comprise antigens and are intended to be used in humans or animals for generating specific defense and protective substance by vaccination.

"Isolated" means that the polynucleotide or polypeptide or fragment, variant, or derivative thereof has been essentially removed from other biological materials with which it is naturally associated, or essentially free from other biological materials derived, e.g., from a recombinant host cell that has been genetically engineered to express the polypeptide of the invention.

"Neoantigen" means a class of tumor antigens which arises from tumor-specific mutations in expressed protein.

"Purified" means that the polynucleotide or polypeptide or fragment, variant, or derivative thereof is substantially free of other biological material with which it is naturally associated, or free from other biological materials derived, e.g., from a recombinant host cell that has been genetically engineered to express the polypeptide of the invention. That is, e.g., a purified polypeptide of the present invention is a polypeptide that is at least about 70-100% pure, i.e., the polypeptide is present in a composition wherein the polypeptide constitutes about 70-100% by weight of the total composition. In some embodiments, the purified polypeptide of the present invention is about 75%-99% by weight pure, about 80%-99% by weight pure, about 90-99% by weight pure, or about 95% to 99% by weight pure.

Identification of Tumor Specific Mutations

The present invention is based, on the identification of certain mutations (e.g., the variants or alleles that are present in cancer cells). In particular, these mutations are present in the genome of cancer cells of a subject having cancer but not in normal tissue from the subject.

Genetic mutations in tumors would be considered useful for the immunological targeting of tumors if they lead to changes in the amino acid sequence of a protein exclusively in the tumor. Useful mutations include: (1) non-synonymous mutations leading to different amino acids in the protein; (2) read-through mutations in which a stop codon is modified or deleted, leading to translation of a longer protein with a novel tumor-specific sequence at the C-terminus; (3) splice site mutations that lead to the inclusion of an intron in the mature mRNA and thus a unique tumor-specific protein sequence; (4) chromosomal rearrangements that give rise to a chimeric protein with tumor-specific sequences at the junction of 2 proteins (i.e., gene fusion); (5) frameshift mutations or deletions that lead to a new open reading frame with a novel tumor-specific protein sequence.

Peptides with mutations or mutated polypeptides arising from for example, splice-site, frameshift, readthrough, or gene fusion mutations in tumor cells may be identified by sequencing DNA, RNA or protein in tumor versus normal cells.

Also within the scope of the inventions are peptides including previous identified tumor specific mutations. Know tumor mutation can be found at the Catalogue of Somatic Mutations in Cancer (COSMIC).

A variety of methods are available for detecting the presence of a particular mutation or allele in an individual's DNA or RNA. Advancements in this field have provided accurate, easy, and inexpensive large-scale SNP genotyping. Most recently, for example, several new techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods require amplification of the target genetic region, typically by PCR. Still other newly developed methods, based on the generation of small signal molecules by invasive cleavage followed by mass spectrometry or immobilized padlock probes and rolling-circle amplification, might eventually eliminate the need for PCR. Several of the methods known in the art for detecting specific single nucleotide polymorphisms are summarized below. The method of the present invention is understood to include all available methods.

PCR based detection means can include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

Several methods have been developed to facilitate analysis of single nucleotide polymorphisms in genomic DNA or celluar RNA. In one embodiment, the single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. Cohen, D. et al. (French Patent 2,650,840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA® is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al., Nucl. Acids. Res. 17:7779-7784 (1989); Sokolov, B. P., Nucl. Acids Res. 18:3671 (1990); Syvanen, A.-C., et al., Genomics 8:684-692 (1990); Kuppuswamy, M. N. et al., Proc. Natl. Acad. Sci. (U.S.A.) 88:1143-1147 (1991); Prezant, T. R. et al., Hum. Mutat. 1:159-164 (1992); Ugozzoli, L. et al., GATA 9:107-112 (1992); Nyren, P. et al., Anal. Biochem. 208:171-175 (1993)). These methods differ from GBA® in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al., Amer. J. Hum. Genet. 52:46-59 (1993)).

A number of initiatives are currently underway to obtain sequence information directly from millions of individual molecules of DNA or RNA in parallel. Real-time single molecule sequencing-by-synthesis technologies rely on the detection of fluorescent nucleotides as they are incorporated into a nascent strand of DNA that is complementary to the template being sequenced. In one method, oligonucleotides 30-50 bases in length are covalently anchored at the 5' end to glass cover slips. These anchored strands perform two functions. First, they act as capture sites for the target template strands if the templates are configured with capture tails complementary to the surface-bound oligonucleotides. They also act as primers for the template directed primer extension that forms the basis of the sequence reading. The capture primers function as a fixed position site for sequence determination using multiple cycles of synthesis, detection, and chemical cleavage of the dye-linker to remove the dye. Each cycle consists of adding the polymerase/labeled nucleotide mixture, rinsing, imaging and cleavage of dye. In an alternative method, polymerase is modified with a fluorescent donor molecule and immobilized on a glass slide, while each nucleotide is color-coded with an acceptor fluorescent moiety attached to a gamma-phosphate. The system detects the interaction between a fluorescently-tagged polymerase and a fluorescently modified nucleotide as the nucleotide becomes incorporated into the de novo chain. Other sequencing-by-synthesis technologies also exist.

Preferably, any suitable sequencing-by-synthesis platform can be used to identify mutations. As described above, four major sequencing-by-synthesis platforms are currently available: the Genome Sequencers from Roche/454 Life Sciences, the 1G Analyzer from Illumina/Solexa, the SOLiD system from Applied BioSystems, and the Heliscope system from Helicos Biosciences. Sequencing-by-synthesis platforms have also been described by Pacific BioSciences and VisiGen Biotechnologies. Each of these platforms can be used in the methods of the invention. In some embodiments, a plurality of nucleic acid molecules being sequenced is bound to a support (e.g., solid support). To immobilize the nucleic acid on a support, a capture sequence/universal priming site can be added at the 3' and/or 5' end of the template. The nucleic acids may be bound to the support by hybridizing the capture sequence to a complementary sequence covalently attached to the support. The capture sequence (also referred to as a universal capture sequence) is a nucleic acid sequence complementary to a sequence attached to a support that may dually serve as a universal primer.

As an alternative to a capture sequence, a member of a coupling pair (such as, e.g., antibody/antigen, receptor/ligand, or the avidin-biotin pair as described in, e.g., US Patent Application No. 2006/0252077) may be linked to each fragment to be captured on a surface coated with a respective second member of that coupling pair.

Subsequent to the capture, the sequence may be analyzed, for example, by single molecule detection/sequencing, e.g., as described in the Examples and in U.S. Pat. No. 7,283,337, including template-dependent sequencing-by-synthesis. In sequencing-by-synthesis, the surface-bound molecule is exposed to a plurality of labeled nucleotide triphosphates in the presence of polymerase. The sequence of the template is determined by the order of labeled nucleotides incorporated into the 3' end of the growing chain. This can be done in real time or can be done in a step-and-repeat mode. For real-time analysis, different optical labels to each nucleotide may be incorporated and multiple lasers may be utilized for stimulation of incorporated nucleotides.

Any cell type or tissue may be utilized to obtain nucleic acid samples for use in the diagnostics described herein. In a preferred embodiment, the DNA or RNA sample is obtained from a tumor or a bodily fluid, e.g., blood, obtained by known techniques (e.g. venipuncture) or saliva. Alternatively, nucleic acid tests can be performed on dry samples (e.g. hair or skin).

Alternatively, protein mass spectrometry may be used to identify or validate the presence of mutated peptides bound to MHC proteins on tumor cells. Peptides can be acid-eluted from tumor cells or from HLA molecules that are immunoprecipitated from tumor, and then identified using mass spectrometry.

Neoantigenic Peptides

The invention further includes isolated peptides that comprise the tumor specific mutations identified by the methods of the invention, peptides that comprise know tumor specific mutations, and mutant polypeptides or fragments thereof identified by the method of the invention. These peptides and polypeptides are referred to herein as "neoantigenic peptides" or "neoantigenic polypeptides". The term "peptide" is used interchangeably with "mutant peptide" and "neoantigenic peptide" in the present specification to designate a series of residues, typically L-amino acids, connected one to the other, typically by peptide bonds between the α-amino and carboxyl groups of adjacent amino acids. Similarly, the term "polypeptide" is used interchangeably with "mutant polypeptide" and "neoantigenic polypeptide" in the present specification to designate a series of residues, typically L-amino acids, connected one to the other, typically by peptide bonds between the α-amino and carboxyl groups of adjacent amino acids. The polypeptides or peptides can be a variety of lengths, either in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described.

In certain embodiments the size of the at least one neoantigenic peptide molecule may comprise, but is not limited to, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 60, about 70, about 80, about 90, about 100, about 110, about 120 or greater amino molecule residues, and any range derivable therein. In specific embodiments the neoantigenic peptide molecules are equal to or less than 50 amino acids.

In some embodiments the particular neoantigenic peptides and polypeptides of the invention are: for MHC Class I 13 residues or less in length and usually consist of between about 8 and about 11 residues, particularly 9 or 10 residues; for MHC Class II, 15-24 residues.

A longer peptide may be designed in several ways. In one case, when HLA-binding peptides are predicted or known, a longer peptide could consist of either: (1) individual binding peptides with an extensions of 2-5 amino acids toward the N- and C-terminus of each corresponding gene product; (2) a concentration of some or all of the binding peptides with extended sequences for each. In another case, when sequencing reveals a long (>10 residues) neoepitope sequence present in the tumor (e.g. due to a frameshift, read-through or intron inclusion that leads to a novel peptide sequence), a longer peptide would consist of: (3) the entire stretch of novel tumor-specific amino acids—thus bypassing the need for computational prediction or in vitro testing of peptide binding to HLA proteins. In both cases, use of a longer peptide allows endogenous processing by patient cells and may lead to more effective antigen presentation and induction of T cell responses.

The neoantigenic peptides and polypeptides bind an HLA protein. In some aspect the neoantigenic peptides and polypeptides binds an HLA protein. with greater affinity than a wild-type peptide. The neoantigenic peptide or polypeptide has an IC50 of at least less than 5000 nM, at least less than 500 nM, at least less then 250 nM, at least less than 200 nM, at least less than 150 nM, at least less than 100 nM, at least less than 50 nM or less.

The neoantigenic peptides and polypeptides does not induce an autoimmune response and/or invoke immunological tolerance when administered to a subject.

The invention also provides compositions comprising at least two or more neoantigenic peptides. In some embodiments the composition contains at least two distinct peptides. Preferably, the at least two distinct peptides are derived from the same polypeptide. By distinct polypeptides is meant that the peptide vary by length, amino acid sequence or both. The peptides are derived from any polypeptide know to or have been found to by the methods of the invention to contain a tumor specific mutation. Suitable polypeptides from which the neoantigenic peptides may be derived can be found for example at the COSMIC database. COSMIC curates comprehensive information on somatic mutations in human cancer. The peptide contains the tumor specific mutation. In some aspects the tumor specific mutation is a driver mutation for a particular cancer type. In some aspects, the peptides are derived from a SF3B1 polypeptide, a MYD88 polypeptide, a TP53 polypeptide, an ATM polypeptide, an Abl polypeptide, A FBXW7 polypeptide, a DDX3X polypeptide, a MAPK1 polypeptide of a GNB1 polypeptide.

By a SF3B1 peptide is meant that the peptide contains a portion of a SF3B1 polypeptide. Preferably, a SF3B1 peptide includes either leucine at amino acid position 625; a histidine at amino acid position 626; a glutamic acid at amino acid position 700; an aspartic acid at amino acid position 742; or an arginine at amino acid position 903, when numbered in accordance with wild-type SF3B1. A wild type SF3B1 is shown in Table A (SEQ ID NO:1).

TABLE A

| Wild Type SF3B1 (SEQ ID NO: 1) |
|---|
| makiakthedieaqireiqgkkaaldeaqgvgldstgyydqeiyggsdsr |
| fagyvtsiaateledddddysssts llgqkkpgyhapvallndipqsteq |
| ydpfaehrppkiadredeykkhrrtmiisperldpfadggktpdpkmnar |
| tymdvmreqhltkeereirqqlaekakagelkvvngaaasqppskrkrrw |
| dqtadqtpgatpkklsswdqaetpghtpslrwdetpgrakgsetpgatpg |
| skiwdptpshtpagaatpgrgdtpghatpghggatssarknrwdetpkte |
| rdtpghgsgwaetprtdrggdsigetptpgaskrksrwdetpasqmggst |
| pvltpgktpigtpamnmatptpghimsmtpeqlqawrwereidernrpls |
| deeldamfpegykvlpppagyvpirtparkltatptplggmtgfhmqted |
| rtmksvndqpsgnlpflkpddiqyfdkllvdvdestlspeeqkerkimkl |
| llkikngtppmrkaalrqitdkarefgagplfnqilpllmsptledqerh |
| llvkvidrilykldd lvrpyvhkilvviepllidedyyarvegreiisnl |
| akaaglatmistmrpdidnmdeyvrnttarafavvasalgipsllpflka |

TABLE A-continued

| Wild Type SF3B1 (SEQ ID NO: 1) |
| --- |
| vckskkswqarhtgikivqqiailmgcailphlrslveiiehglvdeqqk |
| vrtisalaiaalaeaatpygiesfdsvlkplwkgirqhrgkglaaflkai |
| gyliplmdaeyanyytrevmlilirefqspdeemkkivlkvvkqccgtdg |
| veanyikteilppffkhfwqhrmaldrrnyrqlvdttvelankvgaaeii |
| srivddlkdeaeqyrkmvmetiekimgnlgaadidhkleeqlidgilyaf |
| qeqttedsvmlngfgtvvnalgkrvkpylpqicgtvlwrinnksakvrqq |
| aadlisrtavvmktcqeeklmghlgvvlyeylgeeypevlgsilgalkai |
| vnvigmhkmtppikdllprltpilknrhekvqencidlvgriadrgaeyv |
| sarewmricfellellkahkkairratvntfgyiakaigphdvlatllnn |
| lkvqerqnrvcttvaiaivaetcspftvlpalmneyrvpelnvqngvlks |
| lsflfeyigemgkdyiyavtplledalmdrdlvhrqtasavvqhmslgvy |
| gfgcedslnhllnyvwpnvfetsphviqavmgaleglrvaigpcrmlqyc |
| lqglfhparkvrdvywkiynsiyigsqdaliahypriynddkntyiryel |
| dyil |

By a MYD88 peptide is meant that the peptide contains a portion of a MYD88 polypeptide. Preferably, a MYD88 peptide includes either a threonine at amino acid position 232; a leucine at amino acid position 258; or a proline at amino acid position 265, when numbered in accordance with wild-type MYD88 when numbered in accordance with wild-type MYD88. A wild type MYD88 is shown in Table B (SEQ ID NO:2).

TABLE B

| Wild Type MYD88 (SEQ ID NO: 2) |
| --- |
| mrpdraeapgppamaaggpgagsaapvsstsslplaalnmrvrrrlslfl |
| nvrtqvaadwtalaeemdfeyleirqletqadptgrlldawqgrpgasvg |
| rllelltklgrddvllelgpsieedcqkyilkqqqeeaekplqvaavdss |
| vprtaelagittlddplghmperfdaficycpsdiqfvqemirqleqtny |
| rlklcvsdrdvlpgtcvwsiaseliekrcrrmvvvvsddylqskecdfqt |
| kfalslspgahqkrlipikykamkkefpsilrfitvcdytnpctkswfwt |
| rlakalslp |

By a TP53 peptide is meant that the peptide contains a portion of a TP53 polypeptide. Preferably, a TP53 peptide includes either an arginine at amino acid position 111; an arginine at amino acid position 215; a serine at amino acid position 238; a glutamine at amino acid position 248; a phenylalanine at amino acid position 255; a cysteine at amino acid position 273 or an asparagine at amino acid position 281, when numbered in accordance with wild-type TP53. A wild type TP53 is shown in Table C (SEQ ID NO:3).

TABLE C

| Wild Type TP53 (SEQ ID NO: 3) |
| --- |
| meepqsdpsvepplsqetfsdlwkllpennvlsplpsqamddlmlspddi |
| eqwftedpgpdeaprmpeaappvapapaaptpaapapapswplsssvpsq |
| ktyqgsygfrlgflhsgtaksvtctyspalnkmfcqlaktcpvqlwvdst |
| pppgtrvramaiykqsghmtevvrrcphhercsdsdglappghlirvegn |
| lrveylddrntfrhsvvvpyeppevgsdcttihynymcnsscmggmnrrp |
| iltiitledssgnllgrnsfevrvcacpgrdrrteeenlrkkgephhelp |
| pgstkralpnntssspqpkkkpldgeyftlqirgrerfemfrelnealel |
| kdaqagkepggsrahsshlkskkgqstsrhkklmfktegpdsd |

By an ATM peptide is meant that the peptide contains a portion of a SF3B1 polypeptide. Preferably, a ATM peptide includes either a phenylalanine at amino acid position 1252; an arginine at amino acid position 2038; a histidine at amino acid position 2522; or a cysteine at amino acid position 2954, when numbered in accordance with wild-type ATM. A wild type ATM is shown in Table D (SEQ ID NO:4).

TABLE D

| Wild Type ATM (SEQ ID NO: 4) |
| --- |
| mslylndlliccrqlehdraterkkevekfkrlirdpetikhldrhsdsk |
| qgkylnwdavfrflqkyiqketeclriakpnvsastqasrqkkmqeissl |
| vkyfikcanrraprlkcqellnyimdtvkdssngaiygadcsnillkdil |
| syrkywceisqqqwlelfsvyfrlylkpsqdvhrvlvariihavtkgccs |
| qtdglnskfldffskaiqcarqeksssglnhilaaltiflktlavnfrir |
| vcelgdeilptllyiwtqhrlndslkeviielfqlqiyihhpkgaktqek |
| gayestkwrsilynlydllvneishigsrgkyssgfrniavkenlielma |
| dichqvfnedtrsleisqsytttqressdysvpckrkkielgwevikdhl |
| qksqndfdlvpwlqiatqliskypaslpncelspllmilsqllpqqrhge |
| rtpyvlrcltevalcqdkrsnlessqksdllklwnkiwcitfrgisseqi |
| qaenfgllgaiiqgslvevdrefwklftgsacrpscpavccltlalttsi |
| vpgtvkmgieqnmcevnrsfslkesimkwilfyqlegdlenstevppilh |
| snfphlvlekilvsltmknckaamnffqsvpecehhqkdkeelsfsevee |
| lflqttfdkmdfltivrecgiekhqssigfsvhqnlkesldrcllglseq |
| llnnysseitnsetlvrcsrllvgvlgcycymgviaeeeaykselfqkak |
| slmqcagesitlfknktneefrigslrnmmqlctrclsnctkkspnkias |
| gfflrlltsklmndiadickslasfikkpfdrgevesmeddtngnlmeve |
| dqssmnlfndypdssysdanepgesqstigainplaeeylskqdllfldm |
| lkflclcvttaqtntvsfraadirrkllmlidsstleptkslhlhmylml |
| lkelpgeeyplpmedvlellkplsnvcslyrrdqdvcktilnhvlhvvkn |
| lgqsnmdsentrdaqgqfltvigafwhltkerkyifsvrmalvnclktll |
| eadpyskwailnvmgkdfpvnevftqfladnhhqvrmlaaesinrlfqdt |
| kgdssrllkalplklqqtafenaylkagegmremshsaenpetldeiynr |
| ksvlltliavvlscspicekqalfalcksvkenglephlvkkvlekvset |

TABLE D-continued

| Wild Type ATM (SEQ ID NO: 4) |
|---|
| fgyrrledfmashldylvlewlnlqdteynlssfpfillnytniedfyrs |
| cykvliphlvirshfdevksianqiqedwksllltdcfpkilvnilpyfay |
| egtrdsgmaqqretatkvydmlksenllgkqidhlfisnlpeivvellmt |
| lhepanssasqstdlcdfsgdldpapnpphfpshvikatfayisnchktk |
| lksileilskspdsyqkillaiceqaaetnnvykkhrilkiyhlfvslll |
| kdiksglggawafvlrdviytlihyinqrpscimdvslrsfslccdllsq |
| vcqtavtyckdalenhlhvivgtliplvyeqvevqkqvldllkylvidnk |
| dnenlyitiklldpfpdhvvfkdlritqqkikysrgpfslleeinhflsv |
| svydalpltrleglkdlrrqlelhkdqmvdimrasqdnpqdgimvklvvn |
| llqlskmainhtgekevleavgsclgevgpidfstiaiqhskdasytkal |
| klfedkelqwtfimltylnntivedcvkvrsaavtclknilatktghsfw |
| eiykmttdpmlaylqpfrtsrkkflevprfdkenpfeglddinlwiplse |
| nhdiwiktltcafldsggtkceilqllkpmcevktdfcgtvlpylihdil |
| lqdtneswrnllsthvqgfftsclrhfsqtsrsttpanldsesehffrcc |
| ldkksqrtmlavvdymrrqkrpssgtifndafwldlnylevakvaqscaa |
| hftallyaeiyadkksmddqekrslafeegsqsttisslsekskeetgis |
| lqdllleiyrsigepdslygcgggkmlqpitrlrtyeheamwgkalvtyd |
| letaipsstrqagiiqalqnlglchilsvylkgldyenkdwcpeleelhy |
| qaawrnmqwdhctsvskevegtsyheslynalqslrdrefstfyeslkya |
| rvkeveemckrslesvyslyptlsrlqaigelesigelfsrsvthrqlse |
| vyikwqkhsqllkdsdfsfqepimalrtvileilmekemdnsqrecikdi |
| ltkhlvelsilartfkntqlperaifqikqynsvscgvsewqleeaqvfw |
| akkeqslalsilkqmikkldascaannpslkltyteclrvcgnwlaetcl |
| enpavimqtylekavevagnydgessdelrngkmkaflslarfsdtqyqr |
| ienymkssefenkgallkrakeevgllrehkiqtnrytvkvqreleldel |
| alralkedrkrflckavenyincllsgeehdmwvfrlcslwlensgvsev |
| ngmmkrdgmkiptykflplmyqlaarmgtkmmgglgfhevlnnlisrism |
| dhphhtlfiilalananrdefltkpevarrsritknvpkqssqldedrte |
| aanriictirsrrpqmvrsvealcdayiilanldatqwktqrkginipad |
| qpitklknledvvvptmeikvdhtgeygnlvtiqsfkaefrlaggvnlpk |
| iidcvgsdgkerrqlvkgrddlrqdavmqqvfqmcntllqrntetrkrkl |
| tictykvvplsgrsgvlewctgtvpigeflvnnedgahkryrpndfsafg |
| cqkkmmevgkksfeekyevfmdvcqnfgpvfryfcmekfldpaiwfekrl |
| aytrsvatssivgyilglgdrhvgnilineqsaelvhidlgvafeqgkil |
| ptpetvpfrltrdivdgmgitgvegvfrrccektmevmrnsqetlltive |
| vllydplfdwtmnplkalylqqrpedetelhptlnaddqeckrnlsdidq |
| sfnkvaervlmrlqeklkgveegtvlsvgggvnlliqqaidpknlsrlfp |
| gwkawv |

By an Abl peptide is meant that the peptide contains a portion of an Abl polypeptide. Preferably, a Bcr-abl peptide includes a valine at amino acid position 244; a valine at amino acid position 248; a glutamic acid at amino acid position 250; an alanine at amino acid position 250; a histidine at amino acid position 252; an arginine at amino acid position 252; a phenylalanine at amino acid position 253; a histidine at amino acid position 253; a lysine at amino acid position 255; a valine at amino acid position 255; a glycine at amino acid position 276; an isoleucine at amino acid position 315; an asparagine at amino acid position 315; a leucine at amino acid position 317; a threonine at amino acid position 343; a threonine at amino acid position 351; a glycine at amino acid position 355; a valine at amino acid position 359; an alanine at amino acid position 359; an isoleucine at amino acid position 379; a leucine at amino acid position 382; a methionine at amino acid position 387; a proline at amino acid position 396; an arginine at amino acid position 396; a tyrosine at amino acid position 417; or a serine at amino acid position 486, when numbered in accordance with wild-type Abl. A wild type Abl is shown in Table E (SEQ ID NO:5).

TABLE E

| Wild Type Abl (SEQ ID NO: 5) |
|---|
| MLEICLKLVGCKSKKGLSSSSSCYLEEALQRPVASDFEPQGLSEAARWNS |
| KENLLAGPSENDPNLFVALYDFVASGDNTLSITKGEKLRVLGYNHNGEWC |
| EAQTKNGQGWVPSNYITPVNSLEKHSWYHGPVSRNAAEYLLSSGINGSFL |
| VRESESSPGQRSISLRYEGRVYHYRINTASDGKLYVSSESRFNTLAELVH |
| HHSTVADGLITTLHYPAPKRNKPTVYGVSPNYDKWEMERTDITMKHKLGG |
| GQYGEVYEGVWKKYSLTVAVKTLKEDTMEVEEFLKEAAVMKEIKHPNLVQ |
| LLGVCTREPPFYIITEFMTYGNLLDYLRECNRQEVNAVVLLYMATQISSA |
| MEYLEKKNFIHRDLAARNCLVGENHLVKVADFGLSRLMTGDTYTAHAGAK |
| FPIKWTAPESLAYNKFSIKSDVWAFGVLLWEIATYGMSPYPGIDLSQVYE |
| LLEKDYRMERPEGCPEKVYELMRACWQWNPSDRPSFAEIHQAFETMFQES |
| SISDEVEKELGKQGVRGAVSTLLQAPELPTKTRTSRRAAEHRDTTDVPEM |
| PHSKGQGESDPLDHEPAVSPLLPRKERGPPEGGLNEDERLLPKDKKTNLF |
| SALIKKKKKTAPTPPKRSSSFREMDGQPERRGAGEEEGRDISNGALAFTP |
| LDTADPAKSPKPSNGAGVPNGALRESGGSGFRSPHLWKKSSTLTSSRLAT |
| GEEEGGGSSSKRFLRSCSASCVPHGAKDTEWRSVTLPRDLQSTGRQFDSS |
| TFGGHKSEKPALPRKRAGENRSDQVTRGTVTPPPRLVKKNEEAADEVFKD |
| IMESSPGSSPPNLTPKPLRRQVTVAPASGLPHKEEAGKGSALGTPAAAEP |
| VTPTSKAGSGAPGGTSKGPAEESRVRRHKHSSESPGRDKGKLSRLKPAPP |
| PPPAASAGKAGGKPSQSPSQEAAGEAVLGAKTKATSLVDAVNSDAAKPSQ |
| PGEGLKKPVLPATPKPQSAKPSGTPISPAPVPSTLPSASSALAGDQPSST |
| AFIPLISTRVSLRKTRQPPERIASGAITKGVVLDSTEALCLAISRNSEQM |
| ASHSAVLEAGKNLYTFCVSYVDSIQQMRNKFAFREAINKLENNLRELQIC |
| PATAGSGPAATQDFSKLLSSVKEISDIVQR |

By a FBXW7 peptide is meant that the peptide contains a portion of a FBXW7 polypeptide. Preferably, a FBXW7 peptide includes either a leucine at amino acid position 280;

a histidine at amino acid position 465; a cysteine at amino acid position 505; or a glutamic acid at amino acid position 597, when numbered in accordance with wild-type FBXW7. A wild type FBXW7 is shown in Table F (SEQ ID NO6).

TABLE F

| Wild Type FBXW7 (SEQ ID NO: 6) |
|---|
| mnqellsvgskrrrtggslrgnpsssqvdeeqmnrvveeeqqqlrqqee |
| ehtarngevvgveprpggqndsqqgqleennnrfisvdedssgnqeeqee |
| deehageqdeedeeeeemdqesddfdqsddssredehthtnsvtnsssiv |
| dlpvhqlsspfytkttkmkrkldhgsevrsfslgkkpckvseytsttglv |
| pcsatpttfgdlraangqgqqrrritsvqpptglqewlkmfqswsgpekl |
| laldelidsceptqvkhmmqviepqfqrdfisllpkelalyvlsflepkd |
| llqaaqtcrywrilaednllwrekckeegideplhikrrkvikpgfihsp |
| wksayirqhridtnwrrgelkspkvlkghddhvitclqfcgnrivsgsdd |
| ntlkvwsavtgkclrtlvghtggvwssqmrdniiisgstdrtlkvwnaet |
| gecihtlyghtstvrcmhlhekrvvsgsrdatlrvwdietgqclhvlmgh |
| vaavrcvqydgrrvvsgaydfmvkvwdpetetclhtlqghtnrvyslqfd |
| gihvvsgsldtsirvwdvetgncihtltghqsltsgmelkdnilvsgnad |
| stvkiwdiktgqclqtlqgpnkhqsavtclqfnknfvitssddgtvklwd |
| lktgefirnlvtlesggsggvvwrirasntklvcavgsrngteetkllvl |
| dfdvdmk |

By a DDX3X peptide is meant that the peptide contains a portion of a DDX3X polypeptide. A DDX3X peptide is a peptide that is the result of a missence mutation at amino acid position 24; a splice site at amino acid position 342 or a frame shift at amino acid position 410 when numbered in accordance with wild-type DDX3X. A wild type DDX3X is shown in Table G (SEQ ID NO:7).

TABLE G

| Wild Type DDX3X (SEQ ID NO: 7) |
|---|
| mshvavenalgldqqfagldlnssdnqsggstaskgryipphlrnreatk |
| gfydkdssgwssskdkdayssfgsrsdsrgkssffsdrgsgsrgrfddrg |
| rsdydgigsrgdrsgfgkferggnsrwcdksdeddwskplppserleqel |
| fsggntginfekyddipveatgnncpphiesfsdvemgeiimgnieltry |
| trptpvqkhaipiikekrdlmacaqtgsgktaafllpilsqiysdgpgea |
| lramkengrygrrkqypislvlaptrelavqiyeearkfsyrsrvrpcvv |
| yggadigqqirdlergchllvatpgrlvdmmergkigldfckylvldead |
| rmldmgfepqirriveqdtmppkgvrhtmmfsatfpkeiqmlardfldey |
| iflavgrvgstsenitqkvvwveesdkrsflldllnatgkdsltivfvet |
| kkgadsledflyhegyactsihgdrsqrdreealhqfrsgkspilvatav |
| aargldisnvkhvinfdlpsdieeyvhrigrtgrvgnlglatsffnerni |
| nitkdlldllveakqevpswlenmayehhykgssrgrskssrfsggfgar |
| dyrqssgassssfsssrasssrsgggghgssrgfggggyggfynsdgygg |
| nynsqgvdwwgn |

By a MAPK1 peptide is meant that the peptide contains a portion of a MAPK1 polypeptide. Preferably, a MAPK1 peptide includes either an asparagine at amino acid position 162; a glycine at amino acid position 291; or a phenylalanine at amino acid position 316, when numbered in accordance with wild-type MAPK1. A wild type MAPK1 is shown in Table H (SEQ ID NO:8).

TABLE H

| Wild Type MAPK1 (SEQ ID NO: 8) |
|---|
| maaaaaagagpemvrgqvfdvgprytnlsyigegaygmvcsaydnvnkvr |
| vaikkispfehqtycqrtlreikillrfrheniigindiiraptieqmkd |
| vyivqdlmetdlykllktqhlsndhicyflyqilrglkyihsanvlhrdl |
| kpsnlllnttcdlkicdfglarvadpdhdhtgflteyvatrwyrapeiml |
| nskgytksidiwsvgcilaemlsnrpifpgkhyldqlnhilgilgspsqe |
| dlnciinlkarnyllslphknkvpwnrlfpnadskaldlldkmltfnphk |
| rieveqalahpyleqyydpsdepiaeapfkfdmelddlpkeklkelifee |
| tarfqpgyrs |

By a GNB1 peptide is meant that the peptide contains a portion of a GNB1 polypeptide. Preferably, a GNB1 peptide includes a threonine at amino acid position 180, when numbered in accordance with wild-type GNB1. A wild type GNB1 is shown in Table I (SEQ ID NO9).

TABLE I

| Wild Type GNB1 (SEQ ID NO: 9) |
|---|
| mseldqlrqeaeqlknqirdarkacadatlsqitnnidpvgriqmrtrrt |
| lrghlakiyamhwgtdsrllvsasqdgkliiwdsyttnkvhaiplrsswv |
| mtcayapsgnyvacggldnicsiynlktregnvrvsrelaghtgylsccr |
| flddnqivtssgdttcalwdietgqqtttftghtgdvmslslapdtrlfv |
| sgacdasaklwdvregmcrqtftghesdinaicffpngnafatgsddatc |
| rlfdlradqelmtyshdniicgitsvsfsksgrlllagyddfncnvwdal |
| kadragvlaghdnrvsclgvtddgmavatgswdsflkiwn |

Neoantigenic peptides and polypeptides having the desired activity may be modified as necessary to provide certain desired attributes, e.g. improved pharmacological characteristics, while increasing or at least retaining substantially all of the biological activity of the unmodified peptide to bind the desired MHC molecule and activate the appropriate T cell. For instance, the neoantigenic peptide and polypeptides may be subject to various changes, such as substitutions, either conservative or non-conservative, where such changes might provide for certain advantages in their use, such as improved MHC binding. By conservative substitutions is meant replacing an amino acid residue with another which is biologically and/or chemically similar, e.g., one hydrophobic residue for another, or one polar residue for another. The substitutions include combinations such as Gly, Ala; Val, Ile, Leu, Met; Asp, Glu; Asn, Gln; Ser, Thr; Lys, Arg; and Phe, Tyr. The effect of single amino acid substitutions may also be probed using D-amino acids. Such modifications may be made using well known peptide synthesis procedures, as described in e.g., Merrifield, Science 232:341-347 (1986), Barany & Merrifield, The Peptides, Gross & Meienhofer, eds. (N.Y., Academic Press), pp. 1-284 (1979); and Stewart & Young, Solid Phase Peptide Synthesis, (Rockford, Ill., Pierce), 2d Ed. (1984).

The neoantigenic peptide and polypeptides can also be modified by extending or decreasing the compound's amino acid sequence, e.g., by the addition or deletion of amino acids. The peptides, polypeptides or analogs can also be modified by altering the order or composition of certain residues, it being readily appreciated that certain amino acid residues essential for biological activity, e.g., those at critical contact sites or conserved residues, may generally not be altered without an adverse effect on biological activity. The non-critical amino acids need not be limited to those naturally occurring in proteins, such as L-α-amino acids, or their D-isomers, but may include non-natural amino acids as well, such as β-γ-δ-amino acids, as well as many derivatives of L-α-amino acids.

Typically, a series of peptides with single amino acid substitutions are employed to determine the effect of electrostatic charge, hydrophobicity, etc. on binding. For instance, a series of positively charged (e.g., Lys or Arg) or negatively charged (e.g., Glu) amino acid substitutions are made along the length of the peptide revealing different patterns of sensitivity towards various MHC molecules and T cell receptors. In addition, multiple substitutions using small, relatively neutral moieties such as Ala, Gly, Pro, or similar residues may be employed. The substitutions may be homo-oligomers or hetero-oligomers. The number and types of residues which are substituted or added depend on the spacing necessary between essential contact points and certain functional attributes which are sought (e.g., hydrophobicity versus hydrophilicity). Increased binding affinity for an MHC molecule or T cell receptor may also be achieved by such substitutions, compared to the affinity of the parent peptide. In any event, such substitutions should employ amino acid residues or other molecular fragments chosen to avoid, for example, steric and charge interference which might disrupt binding.

Amino acid substitutions are typically of single residues. Substitutions, deletions, insertions or any combination thereof may be combined to arrive at a final peptide. Substitutional variants are those in which at least one residue of a peptide has been removed and a different residue inserted in its place. Such substitutions generally are made in accordance with the following Table when it is desired to finely modulate the characteristics of the peptide.

| Original Residue | Exemplary Substitution |
|---|---|
| Ala | Ser |
| Arg | Lys, His |
| Asn | Gln |
| Asp | Glu |
| Cys | Ser |
| Gln | Asn |
| Glu | Asp |
| Gly | Pro |
| His | Lys; Arg |
| Ile | Leu; Val |
| Leu | Ile; Val |
| Lys | Arg; His |
| Met | Leu; Ile |
| Phe | Tyr; Trp |
| Ser | Thr |
| Thr | Ser |
| Trp | Tyr; Phe |
| Tyr | Trp; Phe |
| Val | Ile; Leu |
| Pro | Gly |

Substantial changes in function (e.g., affinity for MHC molecules or T cell receptors) are made by selecting substitutions that are less conservative than those in above Table, i.e., selecting residues that differ more significantly in their effect on maintaining (a) the structure of the peptide backbone in the area of the substitution, for example as a sheet or helical conformation, (b) the charge or hydrophobicity of the molecule at the target site or (c) the bulk of the side chain. The substitutions which in general are expected to produce the greatest changes in peptide properties will be those in which (a) hydrophilic residue, e.g. seryl, is substituted for (or by) a hydrophobic residue, e.g. leucyl, isoleucyl, phenylalanyl, valyl or alanyl; (b) a residue having an electropositive side chain, e.g., lysl, arginyl, or histidyl, is substituted for (or by) an electronegative residue, e.g. glutamyl or aspartyl; or (c) a residue having a bulky side chain, e.g. phenylalanine, is substituted for (or by) one not having a side chain, e.g., glycine.

The peptides and polypeptides may also comprise isosteres of two or more residues in the neoantigenic peptide or polypeptides. An isostere as defined here is a sequence of two or more residues that can be substituted for a second sequence because the steric conformation of the first sequence fits a binding site specific for the second sequence. The term specifically includes peptide backbone modifications well known to those skilled in the art. Such modifications include modifications of the amide nitrogen, the α-carbon, amide carbonyl, complete replacement of the amide bond, extensions, deletions or backbone crosslinks. See, generally, Spatola, Chemistry and Biochemistry of Amino Acids, Peptides and Proteins, Vol. VII (Weinstein ed., 1983).

Modifications of peptides and polypeptides with various amino acid mimetics or unnatural amino acids are particularly useful in increasing the stability of the peptide and polypeptide in vivo. Stability can be assayed in a number of ways. For instance, peptidases and various biological media, such as human plasma and serum, have been used to test stability. See, e.g., Verhoef et al., Eur. J. Drug Metab Pharmacokin. 11:291-302 (1986). Half life of the peptides of the present invention is conveniently determined using a 25% human serum (v/v) assay. The protocol is generally as follows. Pooled human serum (Type AB, non-heat inactivated) is delipidated by centrifugation before use. The serum is then diluted to 25% with RPMI tissue culture media and used to test peptide stability. At predetermined time intervals a small amount of reaction solution is removed and added to either 6% aqueous trichloracetic acid or ethanol. The cloudy reaction sample is cooled (4° C.) for 15 minutes and then spun to pellet the precipitated serum proteins. The presence of the peptides is then determined by reversed-phase HPLC using stability-specific chromatography conditions.

The peptides and polypeptides may be modified to provide desired attributes other than improved serum half life. For instance, the ability of the peptides to induce CTL activity can be enhanced by linkage to a sequence which contains at least one epitope that is capable of inducing a T helper cell response. Particularly preferred immunogenic peptides/T helper conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer.

When present, the spacer will usually be at least one or two residues, more usually three to six residues. Alternatively, the peptide may be linked to the T helper peptide without a spacer.

The neoantigenic peptide may be linked to the T helper peptide either directly or via a spacer either at the amino or carboxy terminus of the peptide. The amino terminus of either the neoantigenic peptide or the T helper peptide may be acylated. Exemplary T helper peptides include tetanus toxoid 830-843, influenza 307-319, malaria circumsporozoite 382-398 and 378-389.

Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and may be found at computerized databases known to those of ordinary skill in the art. One such database is the National Center for Biotechnology Information's Genbank and GenPept databases located at the National Institutes of Health website. The coding regions for known genes may be amplified and/or expressed using the techniques disclosed herein or as would be known to those of ordinary skill in the art. Alternatively, various commercial preparations of proteins, polypeptides and peptides are known to those of skill in the art.

In a further aspect of the invention provides a nucleic acid (e.g. polynucleotide) encoding a neoantigenic peptide of the invention. The polynucleotide may be e.g. DNA, cDNA, PNA, CNA, RNA, either single- and/or double-stranded, or native or stabilized forms of polynucleotides, such as e.g. polynucleotides with a phosphorothiate backbone, or combinations thereof and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention. Expression vectors for different cell types are well known in the art and can be selected without undue experimentation. Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Guidance can be found e.g. in Sambrook et al. (1989) Molecular Cloning, A Laboratory Manual, Cold Spring Harbor Laboratory, Cold Spring Harbor, N.Y.

Vaccine Compositions

The present invention is directed to an immunogenic composition, e.g., a vaccine composition capable of raising a specific T-cell response. The vaccine composition comprises mutant peptides and mutant polypeptides corresponding to tumor specific neoantigens identified by the methods described herein.

A person skilled in the art will be able to select preferred peptides, polypeptide or combination of thereof by testing, for example, the generation of T-cells in vitro as well as their efficiency and overall presence, the proliferation, affinity and expansion of certain T-cells for certain peptides, and the functionality of the T-cells, e.g. by analyzing the IFN-γ production or tumor killing by T-cells. Usually, the most efficient peptides are then combined as a vaccine.

A suitable vaccine will preferably contain between 1 and 20 peptides, more preferably 2, 3, 4, 5, 6, 7, 8, 9, 10, 11, 12, 13, 14, 15, 16, 17, 18, 19, or 20 different peptides, further preferred 6, 7, 8, 9, 10 11, 12, 13, or 14 different peptides, and most preferably 12, 13 or 14 different peptides.

In one embodiment of the present invention the different peptides and/or polypeptides are selected so that one vaccine composition comprises peptides and/or polypeptides capable of associating with different MHC molecules, such as different MHC class I molecule. Preferably, one vaccine composition comprises peptides and/or polypeptides capable of associating with the most frequently occurring MHC class I molecules. Hence vaccine compositions according to the invention comprises different fragments capable of associating with at least 2 preferred, more preferably at least 3 preferred, even more preferably at least 4 preferred MHC class I molecules.

The vaccine composition is capable of raising a specific cytotoxic T-cells response and/or a specific helper T-cell response.

The vaccine composition can further comprise an adjuvant and/or a carrier. Examples of useful adjuvants and carriers are given herein below. The peptides and/or polypeptides in the composition can be associated with a carrier such as e.g. a protein or an antigen-presenting cell such as e.g. a dendritic cell (DC) capable of presenting the peptide to a T-cell.

Adjuvants are any substance whose admixture into the vaccine composition increases or otherwise modifies the immune response to the mutant peptide. Carriers are scaffold structures, for example a polypeptide or a polysaccharide, to which the neoantigenic peptides, is capable of being associated. Optionally, adjuvants are conjugated covalently or non-covalently to the peptides or polypeptides of the invention.

The ability of an adjuvant to increase the immune response to an antigen is typically manifested by a significant increase in immune-mediated reaction, or reduction in disease symptoms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th response into a primarily cellular, or Th response.

Suitable adjuvants include, but are not limited to 1018 ISS, aluminium salts, Amplivax, AS15, BCG, CP-870,893, CpG7909, CyaA, dSLIM, GM-CSF, IC30, IC31, Imiquimod, ImuFact IMP321, IS Patch, ISS, ISCOMATRIX, JuvImmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel® vector system, PLG microparticles, resiquimod, SRL172, Virosomes and other Virus-like particles, YF-17D, VEGF trap, R848, beta-glucan, Pam3Cys, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox. Quil or Superfos. Adjuvants such as incomplete Freund's or GM-CSF are preferred. Several immunological adjuvants (e.g., MF59) specific for dendritic cells and their preparation have been described previously (Dupuis M, et al., Cell Immunol. 1998; 186(1):18-27; Allison A C; Dev Biol Stand. 1998; 92:3-11).

Also cytokines may be used. Several cytokines have been directly linked to influencing dendritic cell migration to lymphoid tissues (e.g., TNF-alpha), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12) (Gabrilovich D I, et al., J Immunother Emphasis Tumor Immunol. 1996 (6):414-418).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly, it enhances dendritic cell maturation and differentiation, resulting in enhanced activation of TH1 cells and strong cytotoxic T-lymphocyte (CTL) generation, even in the absence of CD4 T-cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nano particles, lipid emulsions or similar formulations, which are especially necessary for inducing a strong response when the antigen is relatively weak. They also accelerate the immune response and enabled the antigen doses to be reduced by approximately two orders of magnitude, with comparable antibody responses to the full-dose vaccine without CpG in some experiments (Arthur M. Krieg, Nature Reviews, Drug Discovery, 5 Jun. 2006, 471-484). U.S. Pat. No. 6,406,705 B1 describes the combined use of CpG oligonucleotides, non-nucleic acid adjuvants and an antigen to induce an antigen-specific immune response. A commercially available CpG TLR9 antagonist is dSLIM (double Stem Loop Immunomodulator) by Mologen (Berlin, GERMANY), which is a preferred component of the pharmaceutical composition of the present invention. Other TLR binding molecules such as RNA binding TLR 7, TLR 8 and/or TLR 9 may also be used.

Other examples of useful adjuvants include, but are not limited to, chemically modified CpGs (e.g. CpR, Idera), Poly(I:C)(e.g. polyi:CI2U), non-CpG bacterial DNA or RNA as well as immunoactive small molecules and antibodies such as cyclophosphamide, sunitinib, bevacizumab, celebrex, NCX-4016, sildenafil, tadalafil, vardenafil, sorafinib, XL-999, CP-547632, pazopanib, ZD2171, AZD2171, ipilimumab, tremelimumab, and SC58175, which may act therapeutically and/or as an adjuvant. The amounts and concentrations of adjuvants and additives useful in the context of the present invention can readily be determined by the skilled artisan without undue experimentation. Additional adjuvants include colony-stimulating factors, such as Granulocyte Macrophage Colony Stimulating Factor (GM-CSF, sargramostim).

A vaccine composition according to the present invention may comprise more than one different adjuvants. Furthermore, the invention encompasses a therapeutic composition comprising any adjuvant substance including any of the above or combinations thereof. It is also contemplated that the peptide or polypeptide, and the adjuvant can be administered separately in any appropriate sequence.

A carrier may be present independently of an adjuvant. The function of a carrier can for example be to increase the molecular weight of in particular mutant in order to increase their activity or immunogenicity, to confer stability, to increase the biological activity, or to increase serum half-life. Furthermore, a carrier may aid presenting peptides to T-cells. The carrier may be any suitable carrier known to the person skilled in the art, for example a protein or an antigen presenting cell. A carrier protein could be but is not limited to keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier must be a physiologically acceptable carrier acceptable to humans and safe. However, tetanus toxoid and/or diptheria toxoid are suitable carriers in one embodiment of the invention. Alternatively, the carrier may be dextrans for example sepharose.

Cytotoxic T-cells (CTLs) recognize an antigen in the form of a peptide bound to an MHC molecule rather than the intact foreign antigen itself. The MHC molecule itself is located at the cell surface of an antigen presenting cell. Thus, an activation of CTLs is only possible if a trimeric complex of peptide antigen, MHC molecule, and APC is present. Correspondingly, it may enhance the immune response if not only the peptide is used for activation of CTLs, but if additionally APCs with the respective MHC molecule are added. Therefore, in some embodiments the vaccine composition according to the present invention additionally contains at least one antigen presenting cell.

The antigen-presenting cell (or stimulator cell) typically has an MHC class I or II molecule on its surface, and in one embodiment is substantially incapable of itself loading the MHC class I or II molecule with the selected antigen. As is described in more detail below, the MHC class I or II molecule may readily be loaded with the selected antigen in vitro.

Preferably, the antigen presenting cells are dendritic cells. Suitably, the dendritic cells are autologous dendritic cells that are pulsed with the neoantigenic peptide. The peptide may be any suitable peptide that gives rise to an appropriate T-cell response. T-cell therapy using autologous dendritic cells pulsed with peptides from a tumor associated antigen is disclosed in Murphy et al. (1996) The Prostate 29, 371-380 and Tjua et al. (1997) The Prostate 32, 272-278.

Thus, in one embodiment of the present invention the vaccine composition containing at least one antigen presenting cell is pulsed or loaded with one or more peptides of the present invention. Alternatively, peripheral blood mononuclear cells (PBMCs) isolated from a patient may be loaded with peptides ex vivo and injected back into the patient.

As an alternative the antigen presenting cell comprises an expression construct encoding a peptide of the present invention. The polynucleotide may be any suitable polynucleotide and it is preferred that it is capable of transducing the dendritic cell, thus resulting in the presentation of a peptide and induction of immunity.

Therapeutic Methods

The invention further provides a method of inducing a tumor specific immune response in a subject, vaccinating against a tumor, treating and or alleviating a symptom of cancer in a subject by administering the subject a neoantigenic peptide or vaccine composition of the invention.

The subject has been diagnosed with cancer or is at risk of developing cancer. The subject has a imatinib resistant tumor. The subject is a human, dog, cat, horse or any animal in which a tumor specific immune response is desired. The tumor is any solid tumor such as breast, ovarian, prostate, lung, kidney, gastric, colon, testicular, head and neck, pancreas, brain, melanoma, and other tumors of tissue organs and hematological tumors, such as lymphomas and leukemias, including acute myelogenous leukemia, chronic myelogenous leukemia, chronic lymphocytic leukemia, T cell lymphocytic leukemia, and B cell lymphomas.

The peptide or composition of the invention is administered in an amount sufficient to induce a CTL response.

In specific embodiments, the invention provides methods of treating an imatinib resistant tumor by administering to a subject one or more neoantigenic peptides that contain a bcr-abl mutation. In some embodiments the subject is HLA-A3. Bcr-abl mutations include for example T315I, E255K, M351T, Y253H, Q252H, F317L, F359V, G250E, Y253F, E355G, E255V, M244V, L248V, G250A, Q252R, D276G, T315N, M343T, F359A, V379I, F382L, L387M, H396P, H396R, S417Y, F486S.

The neoantigenic peptide, polypeptide or vaccine composition of the invention can be administered alone or in combination with other therapeutic agents. The therapeutic agent is for example, a chemotherapeutic agent, radiation, or immunotherapy. Any suitable therapeutic treatment for a particular cancer may be administered. Examples of chemotherapeutic agents include, but are not limited to, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, epoetin alpha, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol®), pilocarpine, prochloroperazine, rituximab, tamoxifen, taxol, topotecan hydrochloride, trastuzumab, vinblastine, vincristine and vinorelbine tartrate. For prostate cancer treatment, a preferred chemotherapeutic agent with which anti-CTLA-4 can be combined is paclitaxel (Taxol®).

In addition, the subject may be further administered an anti-immunosuppressive/immunostimulatory agent. For example, the subject is further administered an anti-CTLA antibody or anti-PD-1 or anti-PD-L1. Blockade of CTLA-4 or PD-L1 by antibodies can enhance the immune response to cancerous cells in the patient. In particular, CTLA-4 blockade has been shown effective when following a vaccination protocol.

The optimum amount of each peptide to be included in the vaccine composition and the optimum dosing regimen can be determined by one skilled in the art without undue experimentation. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. For example, doses of between 1 and 500 mg 50 μg and 1.5 mg, preferably 125 μg to 500 of peptide or DNA may be given and will depend from the respective peptide or DNA. Doses of this range were successfully used in previous trials (Brunsvig P F, et al., Cancer Immunol Immunother. 2006; 55(12):1553-1564; M. Staehler, et al., ASCO meeting 2007; Abstract No 3017). Other methods of administration of the vaccine composition are known to those skilled in the art.

The inventive pharmaceutical composition may be compiled so that the selection, number and/or amount of peptides present in the composition is/are tissue, cancer, and/or patient-specific. For instance, the exact selection of peptides can be guided by expression patterns of the parent proteins in a given tissue to avoid side effects. The selection may be dependent on the specific type of cancer, the status of the disease, earlier treatment regimens, the immune status of the patient, and, of course, the HLA-haplotype of the patient. Furthermore, the vaccine according to the invention can contain individualized components, according to personal needs of the particular patient. Examples include varying the amounts of peptides according to the expression of the related neoantigen in the particular patient, unwanted side-effects due to personal allergies or other treatments, and adjustments for secondary treatments following a first round or scheme of treatment.

For a composition to be used as a vaccine for cancer, peptides whose endogenous parent proteins are expressed in high amounts in normal tissues will be avoided or be present in low amounts in the composition of the invention. On the other hand, if it is known that the tumor of a patient expresses high amounts of a certain protein, the respective pharmaceutical composition for treatment of this cancer may be present in high amounts and/or more than one peptide specific for this particularly protein or pathway of this protein may be included.

Pharmaceutical compositions comprising the peptide of the invention may be administered to an individual already suffering from cancer. In therapeutic applications, compositions are administered to a patient in an amount sufficient to elicit an effective CTL response to the tumor antigen and to cure or at least partially arrest symptoms and/or complications. An amount adequate to accomplish this is defined as "therapeutically effective dose." Amounts effective for this use will depend on, e.g., the peptide composition, the manner of administration, the stage and severity of the disease being treated, the weight and general state of health of the patient, and the judgment of the prescribing physician, but generally range for the initial immunization (that is for therapeutic or prophylactic administration) from about 1.0 μg to about 50,000 μg of peptide for a 70 kg patient, followed by boosting dosages or from about 1.0 μg to about 10,000 μg of peptide pursuant to a boosting regimen over weeks to months depending upon the patient's response and condition by measuring specific CTL activity in the patient's blood. It must be kept in mind that the peptide and compositions of the present invention may generally be employed in serious disease states, that is, life-threatening or potentially life threatening situations, especially when the cancer has metastasized. In such cases, in view of the minimization of extraneous substances and the relative nontoxic nature of the peptide, it is possible and may be felt desirable by the treating physician to administer substantial excesses of these peptide compositions.

For therapeutic use, administration should begin at the detection or surgical removal of tumors. This is followed by boosting doses until at least symptoms are substantially abated and for a period thereafter.

The pharmaceutical compositions (e.g., vaccine compositions) for therapeutic treatment are intended for parenteral, topical, nasal, oral or local administration. Preferably, the pharmaceutical compositions are administered parenterally, e.g., intravenously, subcutaneously, intradermally, or intramuscularly. The compositions may be administered at the site of surgical excision to induce a local immune response to the tumor. The invention provides compositions for parenteral administration which comprise a solution of the peptides and vaccine compositions are dissolved or suspended in an acceptable carrier, preferably an aqueous carrier. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The peptide of the invention may also be administered via liposomes, which target the peptides to a particular cells tissue, such as lymphoid tissue. Liposomes are also useful in increasing the half-life of the peptides. Liposomes include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes filled with a desired peptide of the invention can be directed to the site of lymphoid cells, where the liposomes then deliver the selected therapeutic/immunogenic peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., Ann. Rev. Biophys. Bioeng. 9; 467 (1980), U.S. Pat. Nos. 4,235,871, 4,501,728, 4,837,028 and 5,019,369.

For targeting to the immune cells, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional or nanoparticle nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, the immunogenic peptides are preferably supplied in finely divided form along with a surfactant and propellant. Typical percentages of peptides are 0.01%-20% by weight, preferably 1%-10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included as desired, as with, e.g., lecithin for intranasal delivery.

For therapeutic or immunization purposes, nucleic acids encoding the peptide of the invention and optionally one or more of the peptides described herein can also be administered to the patient. A number of methods are conveniently used to deliver the nucleic acids to the patient. For instance, the nucleic acid can be delivered directly, as "naked DNA". This approach is described, for instance, in Wolff et al., Science 247: 1465-1468 (1990) as well as USA U.S. Pat. Nos. 5,580,859 and 5,589,466. The nucleic acids can also be administered using ballistic delivery as described, for instance, in U.S. Pat. No. 5,204,253. Particles comprised solely of DNA can be administered. Alternatively, DNA can be adhered to particles, such as gold particles.

The nucleic acids can also be delivered complexed to cationic compounds, such as cationic lipids. Lipid-mediated gene delivery methods are described, for instance, in 9618372WOAWO 96/18372; 9324640WOAWO 93/24640; Mannino & Gould-Fogerite, BioTechniques 6(7): 682-691 (1988); 5279833USARose U.S. Pat. No. 5,279,833; 9106309WOAWO 91/06309; and Felgner et al., Proc. Natl. Acad. Sci. USA 84: 7413-7414 (1987).

The peptides and polypeptided of the invention can also be expressed by attenuated viral hosts, such as vaccinia or fowlpox. This approach involves the use of vaccinia virus as a vector to express nucleotide sequences that encode the peptide of the invention. Upon introduction into an acutely or chronically infected host or into a noninfected host, the recombinant vaccinia virus expresses the immunogenic peptide, and thereby elicits a host CTL response. Vaccinia vectors and methods useful in immunization protocols are described in, e.g., U.S. Pat. No. 4,722,848. Another vector is BCG (Bacille Calmette Guerin). BCG vectors are described in Stover et al. (Nature 351:456-460 (1991)). A wide variety of other vectors useful for therapeutic administration or immunization of the peptides of the invention, e.g., *Salmonella typhi* vectors and the like, will be apparent to those skilled in the art from the description herein.

A preferred means of administering nucleic acids encoding the peptide of the invention uses minigene constructs encoding multiple epitopes. To create a DNA sequence encoding the selected CTL epitopes (minigene) for expression in human cells, the amino acid sequences of the epitopes are reverse translated. A human codon usage table is used to guide the codon choice for each amino acid. These epitope-encoding DNA sequences are directly adjoined, creating a continuous polypeptide sequence. To optimize expression and/or immunogenicity, additional elements can be incorporated into the minigene design. Examples of amino acid sequence that could be reverse translated and included in the minigene sequence include: helper T lymphocyte, epitopes, a leader (signal) sequence, and an endoplasmic reticulum retention signal. In addition, MHC presentation of CTL epitopes may be improved by including synthetic (e.g. poly-alanine) or naturally-occurring flanking sequences adjacent to the CTL epitopes.

The minigene sequence is converted to DNA by assembling oligonucleotides that encode the plus and minus strands of the minigene. Overlapping oligonucleotides (30-100 bases long) are synthesized, phosphorylated, purified and annealed under appropriate conditions using well known techniques. The ends of the oligonucleotides are joined using T4 DNA ligase. This synthetic minigene, encoding the CTL epitope polypeptide, can then cloned into a desired expression vector.

Standard regulatory sequences well known to those of skill in the art are included in the vector to ensure expression in the target cells. Several vector elements are required: a promoter with a down-stream cloning site for minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences can also be considered for increasing minigene expression. It has recently been proposed that immunostimulatory sequences (ISSs or CpGs) play a role in the immunogenicity of DNA' vaccines. These sequences could be included in the vector, outside the minigene coding sequence, if found to enhance immunogenicity.

In some embodiments, a bicistronic expression vector, to allow production of the minigene-encoded epitopes and a second protein included to enhance or decrease immunogenicity can be used. Examples of proteins or polypeptides that could beneficially enhance the immune response if co-expressed include cytokines (e.g., IL2, IL12, GM-CSF), cytokine-inducing molecules (e.g. LeIF) or costimulatory molecules. Helper (HTL) epitopes could be joined to intracellular targeting signals and expressed separately from the CTL epitopes. This would allow direction of the HTL epitopes to a cell compartment different than the CTL epitopes. If required, this could facilitate more efficient entry of HTL epitopes into the MHC class II pathway, thereby improving CTL induction. In contrast to CTL induction, specifically decreasing the immune response by co-expression of immunosuppressive molecules (e.g. TGF-β) may be beneficial in certain diseases.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

Purified plasmid DNA can be prepared for injection using a variety of formulations. The simplest of these is reconstitution of lyophilized DNA in sterile phosphate-buffer saline (PBS). A variety of methods have been described, and new techniques may become available. As noted above, nucleic acids are conveniently formulated with cationic lipids. In addition, glycolipids, fusogenic liposomes, peptides and compounds referred to collectively as protective, interactive, non-condensing (PINC) could also be complexed to purified plasmid DNA to influence variables such as stability, intramuscular dispersion, or trafficking to specific organs or cell types.

Target cell sensitization can be used as a functional assay for expression and MHC class I presentation of minigene-encoded CTL epitopes. The plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 labeled and used as target cells for epitope-specific CTL lines. Cytolysis, detected by 51 Cr release, indicates production of MHC presentation of mini gene-encoded CTL epitopes.

In vivo immunogenicity is a second approach for functional testing of minigene DNA formulations. Transgenic mice expressing appropriate human MHC molecules are immunized with the DNA product. The dose and route of administration are formulation dependent (e.g. IM for DNA in PBS, IP for lipid-complexed DNA). Twenty-one days after immunization, splenocytes are harvested and restimulated for 1 week in the presence of peptides encoding each epitope being tested. These effector cells (CTLs) are assayed for cytolysis of peptide-loaded, chromium-51 labeled target cells using standard techniques. Lysis of target cells sensitized by MHC loading of peptides corresponding to minigene-encoded epitopes demonstrates DNA vaccine function for in vivo induction of CTLs.

Peptides may be used to elicit CTL ex vivo, as well. The resulting CTL, can be used to treat chronic tumors in patients that do not respond to other conventional forms of therapy, or will not respond to a peptide vaccine approach of therapy. Ex vivo CTL responses to a particular tumor antigen are induced by incubating in tissue culture the patient's CTL precursor cells (CTLp) together with a source of antigen-presenting cells (APC) and the appropriate peptide. After an appropriate incubation time (typically 1-4 weeks), in which the CTLp are activated and mature and expand into effector CTL, the cells are infused back into the patient, where they will destroy their specific target cell (i.e., a tumor cell). In order to optimize the in vitro conditions for the generation of specific cytotoxic T cells, the culture of stimulator cells is maintained in an appropriate serum-free medium.

Prior to incubation of the stimulator cells with the cells to be activated, e.g., precursor CD8+ cells, an amount of antigenic peptide is added to the stimulator cell culture, of sufficient quantity to become loaded onto the human Class I molecules to be expressed on the surface of the stimulator cells. In the present invention, a sufficient amount of peptide is an amount that will allow about 200, and preferably 200 or more, human Class I MHC molecules loaded with peptide to be expressed on the surface of each stimulator cell. Preferably, the stimulator cells are incubated with >2 μg/ml peptide. For example, the stimular cells are incubates with >3, 4, 5, 10, 15, or more μg/ml peptide.

Resting or precursor CD8+ cells are then incubated in culture with the appropriate stimulator cells for a time period sufficient to activate the CD8+ cells. Preferably, the CD8+ cells are activated in an antigen-specific manner. The ratio of resting or precursor CD8+(effector) cells to stimulator cells may vary from individual to individual and may further depend upon variables such as the amenability of an individual's lymphocytes to culturing conditions and the nature and severity of the disease condition or other condition for which the within-described treatment modality is used. Preferably, however, the lymphocyte:stimulator cell ratio is in the range of about 30:1 to 300:1. The effector/stimulator culture may be maintained for as long a time as is necessary to stimulate a therapeutically useable or effective number of CD8+ cells.

The induction of CTL in vitro requires the specific recognition of peptides that are bound to allele specific MHC class I molecules on APC. The number of specific MHC/peptide complexes per APC is crucial for the stimulation of CTL, particularly in primary immune responses. While small amounts of peptide/MHC complexes per cell are sufficient to render a cell susceptible to lysis by CTL, or to stimulate a secondary CTL response, the successful activation of a CTL precursor (pCTL) during primary response requires a significantly higher number of MHC/peptide complexes. Peptide loading of empty major histocompatability complex molecules on cells allows the induction of primary cytotoxic T lymphocyte responses. Peptide loading of empty major histocompatability complex molecules on cells enables the induction of primary cytotoxic T lymphocyte responses.

Since mutant cell lines do not exist for every human MHC allele, it is advantageous to use a technique to remove endogenous MHC-associated peptides from the surface of APC, followed by loading the resulting empty MHC molecules with the immunogenic peptides of interest. The use of non-transformed (non-tumorigenic), noninfected cells, and preferably, autologous cells of patients as APC is desirable for the design of CTL induction protocols directed towards development of ex vivo CTL therapies. This application discloses methods for stripping the endogenous MHC-associated peptides from the surface of APC followed by the loading of desired peptides.

A stable MHC class I molecule is a trimeric complex formed of the following elements: 1) a peptide usually of 8-10 residues, 2) a transmembrane heavy polymorphic protein chain which bears the peptide-binding site in its $\alpha1$ and $\alpha2$ domains, and 3) a non-covalently associated non-polymorphic light chain, β2microglobuiin. Removing the bound peptides and/or dissociating the β2microglobulin from the complex renders the MHC class I molecules nonfunctional and unstable, resulting in rapid degradation. All MHC class I molecules isolated from PBMCs have endogenous peptides bound to them. Therefore, the first step is to remove all endogenous peptides bound to MHC class I molecules on the APC without causing their degradation before exogenous peptides can be added to them.

Two possible ways to free up MHC class I molecules of bound peptides include lowering the culture temperature from 37° C. to 26° C. overnight to destablize β2microglobulin and stripping the endogenous peptides from the cell using a mild acid treatment. The methods release previously bound peptides into the extracellular environment allowing new exogenous peptides to bind to the empty class I molecules. The cold-temperature incubation method enables exogenous peptides to bind efficiently to the MHC complex, but requires an overnight incubation at 26° C. which may slow the cell's metabolic rate. It is also likely that cells not actively synthesizing MHC molecules (e.g., resting PBMC) would not produce high amounts of empty surface MHC molecules by the cold temperature procedure.

Harsh acid stripping involves extraction of the peptides with trifluoroacetic acid, pH 2, or acid denaturation of the immunoaffinity purified class I-peptide complexes. These methods are not feasible for CTL induction, since it is important to remove the endogenous peptides while preserving APC viability and an optimal metabolic state which is critical for antigen presentation. Mild acid solutions of pH 3 such as glycine or citrate-phosphate buffers have been used to identify endogenous peptides and to identify tumor associated T cell epitopes. The treatment is especially effective, in that only the MHC class I molecules are destabilized (and associated peptides released), while other surface antigens remain intact, including MHC class II molecules. Most importantly, treatment of cells with the mild acid solutions do not affect the cell's viability or metabolic state. The mild acid treatment is rapid since the stripping of the endogenous peptides occurs in two minutes at 4° C. and the APC is ready to perform its function after the appropriate peptides are loaded. The technique is utilized herein to make peptide-specific APCs for the generation of primary antigen-specific CTL. The resulting APC are efficient in inducing peptide-specific CD8+ CTL.

Activated CD8+ cells may be effectively separated from the stimulator cells using one of a variety of known methods. For example, monoclonal antibodies specific for the stimulator cells, for the peptides loaded onto the stimulator cells, or for the CD8+ cells (or a segment thereof) may be utilized to bind their appropriate complementary ligand. Antibody-tagged molecules may then be extracted from the stimulator-effector cell admixture via appropriate means, e.g., via well-known immunoprecipitation or immunoassay methods.

Effective, cytotoxic amounts of the activated CD8+ cells can vary between in vitro and in vivo uses, as well as with the amount and type of cells that are the ultimate target of these killer cells. The amount will also vary depending on the condition of the patient and should be determined via consideration of all appropriate factors by the practitioner. Preferably, however, about $1\times10^6$ to about $1\times10^{12}$, more preferably about $1\times10^8$ to about $1\times10^{11}$, and even more preferably, about $1\times10^9$ to about $1\times10^{10}$ activated CD8+ cells are utilized for adult humans, compared to about $5\times10^6$-$5\times10^7$ cells used in mice.

Preferably, as discussed above, the activated CD8+ cells are harvested from the cell culture prior to administration of the CD8+ cells to the individual being treated. It is important to note, however, that unlike other present and proposed treatment modalities, the present method uses a cell culture system that is not tumorigenic. Therefore, if complete separation of stimulator cells and activated CD8+ cells is not achieved, there is no inherent danger known to be associated with the administration of a small number of stimulator cells, whereas administration of mammalian tumor-promoting cells may be extremely hazardous.

Methods of re-introducing cellular components are known in the art and include procedures such as those exemplified in U.S. Pat. No. 4,844,893 to Honsik, et al. and U.S. Pat. No. 4,690,915 to Rosenberg. For example, administration of activated CD8+ cells via intravenous infusion is appropriate.

The invention will be further described in the following examples, which do not limit the scope of the invention described in the claims.

EXAMPLES

Example 1: A Strategy to Identify Neoepitopes for Vaccination

Our approach to identify tumor-specific neoepitopes involves 3 steps. (1) Identification of DNA mutations using whole genome or whole exome (i.e. only captured exons) sequencing of tumor versus matched germline samples from each patient. Our preliminary studies demonstrate that CLL cells contain many distinct genetic changes that alter amino acid sequence and could generate potential novel T cell epitopes. (2) Application of highly validated peptide-MHC binding prediction algorithms to generate a set of candidate T cell epitopes based on non-silent mutations present in tumors. We will confirm expression of mutated genes as RNA in CLL samples, and then confirm the peptide-HLA binding predictions using an experimental approach to quantify binding of candidate peptides to HLA alleles. (3) Generation of antigen-specific T cells against mutated peptides.

Example 2: Tumor and Normal Genome Sequencing for the Identification of Mutated Genes in Tumors of Patients with Chronic Lymphocytic Leukemia (Step 1)

To detect tumor-specific mutations (that are not present in normal tissues), samples were collected from tumors and from normal tissues of each patient. For leukemias, tumors were purified using magnetic bead isolation or fluorescence-activated cell sorting using antibodies specific to tumor cells, e.g., the tumor cells of patients with chronic lymphocytic leukemia (CLL) express the CD5 and CD19 surface markers. Skin fibroblasts were used as a normal tissue control. DNA or RNA for sequencing was purified from isolated tumor or normal tissue cells. For melanoma, ovarian and other solid tumors (in which there is contamination with non-tumor cells), DNA and RNA were isolated from relatively homogeneous short-term cultures of tumor cells or from laser-captured tumor. PBMCs were used as normal control cells. For all samples, PBMCs were cryopreserved until needed for expansion of mutated peptide-specific T cells. Finally, short-term cultures of tumor cells were also cryopreserved for later use as targets of expanded T cells. Isolated genomic DNA or RNA was tested for nucleic acid integrity and purity prior to sequencing.

For each sample of DNA, whole genomic DNA was sheared and sequenced, or coding exons were captured by complementary oligonucleotides using hybrid selection and then sequenced (Gnirke et al., Nat Biotechnol. 2009, 27(2): 182-9). DNA and RNA libraries were generated and sequenced using Illumina next-generation sequencing instruments.

Sequencing of 64 patients with chronic lymphocytic leukemia (CLL) yielded an average of 23 non-silent mutations that alter protein amino acid sequences (FIG. 3) in the tumor relative to the germline DNA sequence. These non-silent mutations fall into 5 distinct classes with the potential to generate neoepitopes: missense, splice-site, frame-shift (indel, insertions and deletions), read-through and gene fusions (FIG. 4). The frequencies of these mutations vary across individual patients (FIG. 5). All these mutations provide potential neoepitopes for immunization, with frame-shift, read-through and splice-site (e.g. with retained introns) mutations generating longer stretches of novel peptides, missense mutations leading to short peptides with single amino acid changes and finally, fusion genes generating hybrid peptides with novel junction sequences.

Example 3: Identification of HLA-Binding Peptides Derived from Expressed Proteins Harboring Tumor-Specific Mutations (Step 2)

The next question is whether mutated genes may generate peptides that can be presented by patient MHC/HLA proteins. First, several algorithms were used to predict 30 and 137 HLA-binding peptides with IC50 scores <500 nM from 10 missense mutations of Patient 1, and from 53 missense 1 indel and 2 gene fusions of Patient 2. An example for one missense mutation in a patient with 6 specific HLA alleles is shown with 2 predicted binding peptides out of 54 combinations of 9-mers peptides and HLA alleles (FIG. 6). To confirm that these genes are expressed in tumors, we measure RNA levels for the mutated genes (using several approaches that depend on the mutation class, FIG. 7), and found that 98% of mutated genes with HLA binding peptides were expressed.

The HLA binding capacity of all predicted peptides that pass RNA expression validation are then experimentally validated by performing competitive binding assays with test peptides versus reference peptides known to bind to the HLA allele. (Sidney et al. Curr Protoc Immunol. 2001, Chapter 18:Unit 18.3) (FIG. 8A). Of the subset that we submitted for experimental confirmation of HLA binding, 8 of 17 (47%) predicted peptides from missense mutations in Pt 1 were confirmed to have high binding affinities for HLA alleles ($IC_{50}$<500)(FIG. 8B). For Pt 2, 25 of 49 predicted peptides were experimentally confirmed as HLA binding (FIG. 8B). These results suggest that all peptides with predicted $IC_{50}$<150 nM show HLA binding experimentally, while a cut-off of <500 nM generates true binding peptides 40-50% of the time (FIG. 8C). Of note, 12 of the 25 confirmed mutated peptides of Pt 2 have >2-fold better binding affinity than the germline peptide (FIG. 9). While such peptides are preferable for incorporating in a tumor vaccine to reduce the chance of T cells cross-reacting with the germline peptide, peptides that do not show differential binding may still provide tumor-specific responses due to differential recognition of mutant vs. germline peptide by the T cell receptor.

Example 4: CD8+ T Cell Responses Against Mutated Peptides Identified by Sequencing CLL Patient Samples (Step 3)

Based on the predicted or experimentally verified HLA-binding mutated peptides, we can now determine whether T cells can be generated to recognize these tumor-specific mutated peptides. We thus synthesized peptides with binding scores of less than 1000 nM that are derived from genes with validated expression in tumor cells. To generate T cells of desired specificity, we stimulated T cells of the sequenced patients with peptide-pulsed (either using an individual peptide or a peptide pool) autologous APCs (dendritic cells and CD40L-expanded autologous B cells) on a weekly basis, in the presence of IL-2 and IL-7. After 3-4 rounds of stimulation, the expanded CD8+ cells were tested on ELISpot for evidence of reactivity against the peptide, based on IFNgamma secretion. Of the 17 candidate peptides of Patient 1 (FIG. 10), we have detected IFNgamma secretion in T cells against autologous DCs pulsed with a mutated peptide from the TLK2 gene.

Example 5: Mutated BCR-ABL Gene Binds to Patient MHC/HLA Proteins and can Elicit Mutant-Peptide-Specific CD8+ T Cells We performed a more complete study of T cell responses to tumor-specific mutant peptides in patients with another type of leukemia, chronic myeloid leukemia (CIVIL). CIVIL is defined by the expression of a tumor-specific translocation, the product of the BCR-ABL gene fusion.

Mutations in BCR-ABL develop in CIVIL patients who develop drug resistance to front-line pharmacologic therapy with imatinib mesylate, which targets BCR-ABL. Potentially, these mutations may generate neoepitopes that T cells from the host, or an engrafted normal donor, can recognize when bound to MHC proteins; these T cells are likely to be minimally tolerized.

We considered the 20 most common mutations that evolve in patients with resistance to imatinib, and predicted the binding of 9- and 10-mer peptides tiled around each mutation. Using either the NetMHC (Nielsen et al. PLoS One. 2007, 2(8):e796) or IEDB (Vita R et al. Nucleic Acids Res. 2010, 38:D854-62) predictive algorithms, we predicted binding of 84 peptides from 20 common mutations to one or more 8 common HLA alleles ($IC_{50}<1000$), with many peptides derived from the three most common mutations. 24 of 84 peptides were predicted to be strong binders ($IC_{50}<50$) (FIG. 11), 42 peptides intermediate binders ($50<IC_{50}<500$), and 18 peptides weak binders ($500<IC_{50}<1000$).

Figures 12A, 12B, 12C, 12D:
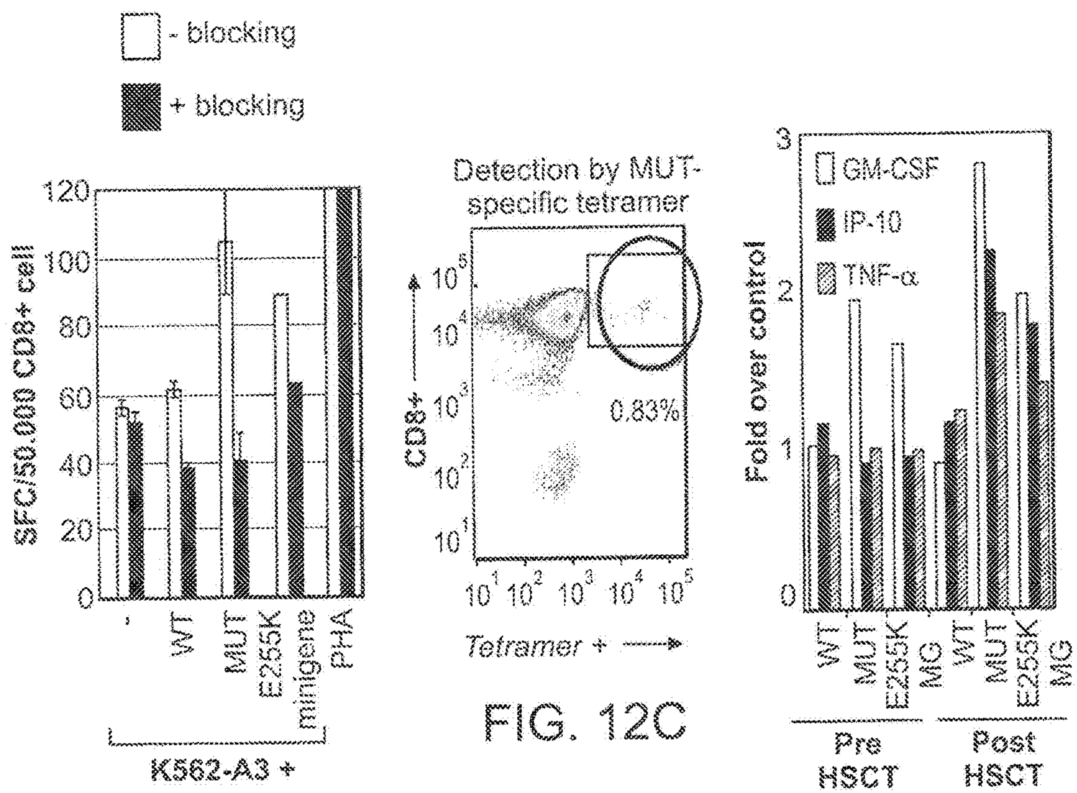

We focused our attention on a mutant peptide generated from the E255K ($E255K\text{-}B_{255\text{-}263}$) mutation (KVYEGVWKK) (SEQ ID NO: 10) that is predicted to bind with high affinity to HLA-A3. ($IC_{50}$=33.1). Using a competitive MHC binding assay (FIG. 8A), we experimentally confirmed the high binding affinity of E255K-B for HLA-A3 ($IC_{50}$=17 nM) with ~10-fold stronger HLA-binding of the mutant peptide compared to the parental (wildtype) peptide (FIG. 12A). E255K-B was also experimentally verified to bind other A3 supertype family members HLA-A*1101 and HLA-A*68. We next generated T cell lines against E255K-B from a normal HLA-A3+ donor and 2 E255K+/HLA-A3+ CML patients that each demonstrated greater specificity against the mutated than the parental peptide (FIG. 12B 12C). E255K-B appears to be endogenously processed and presented since T cells reactive for E255K-B also responded to HLA-A3+APCs transfected with a minigene encompassing 227 base pairs surrounding the E255K mutation. Finally, E255K reactivity in one patient developed only following curative allo-HSCT (FIG. 12D). These studies demonstrate that leukemia-driven genetic alterations can provide novel immunogenic tumor-specific antigen targets that are associated with clinical response in vivo. Our approach to identifying immunogenic T cell epitopes of mutated BCR-ABL thus illustrates an effective strategy for applying bioinformatics tools to discover T cell epitopes from mutated genes.

Example 6: Patient T Cell Clones that Recognize Tumor Epitopes can Selectively Kill Cells Presenting Mutated Epitopes Confirmation of target specificity of T cells is best addressed by characterization of individual T cell clones. We therefore typically isolate mutated peptide-specific T cell clones by limiting dilution of reactive T cell lines and then use standard chromium release assays to screen for T cell clones that demonstrate differential killing of mutated vs germ line peptide-pulsed autologous APCs. Using a standard dilution series for each peptide, we measure the concentration of peptide required for 50% killing. If the ratio of wild type to mutant peptides needed for 50% killing is greater than 10-fold, we conclude that there is differential recognition of these peptides by T cells, as seen previously for mutated tumor antigens. We have carried out this procedure for a CML tumor antigen, CML66. To determine whether CML66-peptide-specific T cells recognize processed and presented epitopes, CML66-peptide-reactive T cells were incubated with autologous APCs transduces to express the entire CML66 protein. We expressed CML66 by nucleofection of either plasmid DNA, or in vitro transcribed RNA (in DCs, CD40L-expanded B cells, or K562 cells with engineered HLA molecules). As shown in FIG. 13A, stimulated T cells were specific to HLA-B4403 bound CML66-derived peptide epitope (peptide 66-72C). Since whole CML66 protein was efficiently expressed when CD40L-expanded B cells were nucleofected with CML66 mRNA (FIG. 13B), we were able to use these cells (or peptide pulsed cells) as targets in a standard chromium release assay and found that the T cells lysed these targets cell effectively (FIG. 13C). Comparable assays, including lysing of patient-matched tumor cells, are being carried out for each of the mutated peptide-specific T cell lines generated from each cancer patient (e.g. using the T cell lines described in Examples 6 and 7).

Example 7: Mutated Tumor Drivers as Potential Tumor Antigens

Of 1188 nonsilent mutations across 64 patients, we identified 8 recurrent mutations, including SF3B1 (16% of CLL patients), TP53 (12.5%), MYD88 (9%), ATM (9%), FBXW7 (6%), MAPK1 (5%), GNB1 (3%) and M6PR (3%) (FIG. 14A-14C). These mutations (especially the most frequent ones: SF3B1, TP53, MYD88 and ATM) are predicted to be driver mutations that are essential for tumor development or progression. These driver genes represent promising tumor-specific antigens for inclusion in a vaccine.

SF3B1 is the most frequently mutated gene in CLL, is mutated at conserved sites, is highly expressed in CLL patients (FIG. 15), and has not been previously described. The most common SF3B1 mutation was K700E (40% of SF3B1 mutations); genotyping of an additional 89 independent CLL patients uncovered 6 more patient tumors harboring this mutation. By applying peptide-HLA binding algorithms to the SF3B1 mutations, we predict binding of the mutated peptides to the most common HLA-A2 allele (FIG. 16). If a peptide that harbors the most common mutation in CLL (SF3B1 K700E) binds the most common class I HLA allele (HLA-A2), then this peptide is an excellent candidate for inclusion in a CLL vaccine for many CLL patients.

REFERENCES

Albert, T. J., Molla, M. N., Muzny, D. M., Nazareth, L., Wheeler, D., Song, X., Richmond, T. A., Middle, C. M., Rodesch, M. J., Packard, C. J., et al. (2007). Direct selection of human genomic loci by microarray hybridization. Nat Methods 4, 903-905.

Alyea, E. P., Soiffer, R. J., Canning, C., Neuberg, D., Schlossman, R., Pickett, C., Collins, H., Wang, Y., Anderson, K. C., and Ritz, J. (1998). Toxicity and efficacy of defined doses of CD4(+) donor lymphocytes for treatment of relapse after allogeneic bone marrow transplant. Blood 91, 3671-3680.

Annunziata, C. M., Davis, R. E., Demchenko, Y., Bellamy, W., Gabrea, A., Zhan, F., Lenz, G., Hanamura, I., Wright, G., Xiao, W., et al. (2007). Frequent engagement of the classical and alternative NF-kappaB pathways by diverse genetic abnormalities in multiple myeloma. Cancer Cell 12, 115-130.

Attia, P., Phan, G. Q., Maker, A. V., Robinson, M. R., Quezado, M. M., Yang, J. C., Sherry, R. M., Topalian, S. L., Kammula, U. S., Royal, R. E., et al. (2005). Autoimmunity correlates with tumor regression in patients with metastatic melanoma treated with anti-cytotoxic T-lymphocyte antigen-4. J Clin Oncol 23, 6043-6053.

Austen, B., Powell, J. E., Alvi, A., Edwards, I., Hooper, L., Starczynski, J., Taylor, A. M., Fegan, C., Moss, P., and Stankovic, T. (2005). Mutations in the ATM gene lead to impaired overall and treatment-free survival that is independent of IGVH mutation status in patients with B-CLL. Blood 106, 3175-3182.

Balakrishnan, A., Bleeker, F. E., Lamba, S., Rodolfo, M., Daniotti, M., Scarpa, A., van Tilborg, A. A., Leenstra, S., Zanon, C., and Bardelli, A. (2007). Novel somatic and germline mutations in cancer candidate genes in glioblastoma, melanoma, and pancreatic carcinoma. Cancer Res 67, 3545-3550.

Baskar, S., Kobrin, C. B., and Kwak, L. W. (2004). Autologous lymphoma vaccines induce human T cell responses against multiple, unique epitopes. J Clin Invest 113, 1498-1510. Baurain, J. F., Colau, D., van Baren, N., Landry, C., Martelange, V., Vikkula, M., Boon, T., and Coulie, P. G. (2000). High frequency of autologous anti-melanoma CTL directed against an antigen generated by a point mutation in a new helicase gene. J Immunol 164, 6057-6066. Beck, K. E., Blansfield, J. A., Tran, K. Q., Feldman, A. L., Hughes, M. S., Royal, R. E., Kammula, U. S., Topalian, S. L., Sherry, R. M., Kleiner, D., et al. (2006). Enterocolitis in patients with cancer after antibody blockade of cytotoxic T-lymphocyte-associated antigen 4. J Clin Oncol 24, 2283-2289.

Bellucci, R., Wu, C. J., Chiaretti, S., Weller, E., Davies, F. E., Alyea, E. P., Dranoff, G., Anderson, K. C., Munshi, N. C., and Ritz, J. (2004). Complete response to donor lymphocyte infusion in multiple myeloma is associated with antibody responses to highly expressed antigens. Blood 103, 656-663.

Boon, T., Coulie, P. G., Van den Eynde, B. J., and van der Bruggen, P. (2006). Human T cell responses against melanoma. Annu Rev Immunol 24, 175-208.

Brandle, D., Brasseur, F., Weynants, P., Boon, T., and Van den Eynde, B. (1996). A mutated HLA-A2 molecule recognized by autologous cytotoxic T lymphocytes on a human renal cell carcinoma. J Exp Med 183, 2501-2508.

Carpten, J. D., Faber, A. L., Horn, C., Donoho, G. P., Briggs, S. L., Robbins, C. M., Hostetter, G., Boguslawski, S., Moses, T. Y., Savage, S., et al. (2007). A transforming mutation in the pleckstrin homology domain of AKT1 in cancer. Nature 448, 439-444.

Chiari, R., Foury, F., De Plaen, E., Baurain, J. F., Thonnard, J., and Coulie, P. G. (1999). Two antigens recognized by autologous cytolytic T lymphocytes on a melanoma result from a single point mutation in an essential housekeeping gene. Cancer Res 59, 5785-5792.

De Plaen, E., Lurquin, C., Van Pel, A., Mariame, B., Szikora, J. P., Wolfel, T., Sibille, C., Chomez, P., and Boon, T. (1988). Immunogenic (tum-) variants of mouse tumor P815: cloning of the gene of tum-antigen P91A and identification of the tum-mutation. Proc Natl Acad Sci USA 85, 2274-2278.

Dudley, M. E., Wunderlich, J. R., Robbins, P. F., Yang, J. C., Hwu, P., Schwartzentruber, D. J., Topalian, S. L., Sherry, R., Restifo, N. P., Hubicki, A. M., et al. (2002). Cancer regression and autoimmunity in patients after clonal repopulation with antitumor lymphocytes. Science 298, 850-854.

Estep, A. L., Palmer, C., McCormick, F., and Rauen, K. A. (2007). Mutation Analysis of BRAF, MEK1 and MEK2 in 15 Ovarian Cancer Cell Lines: Implications for Therapy. PLoS ONE 2, e1279.

Garcia-Marco, J. A., Caldas, C., Price, C. M., Wiedemann, L. M., Ashworth, A., and Catovsky, D. (1996). Frequent somatic deletion of the 13q12.3 locus encompassing BRCA2 in chronic lymphocytic leukemia. Blood 88, 1568-1575.

Gilboa, E. (1999). The makings of a tumor rejection antigen. Immunity 11, 263-270. Greenman, C., Stephens, P., Smith, R., Dalgliesh, G. L., Hunter, C., Bignell, G., Davies, H., Teague, J., Butler, A., Stevens, C., et al. (2007). Patterns of somatic mutation in human cancer genomes. Nature 446, 153-158.

Gueguen, M., Patard, J. J., Gaugler, B., Brasseur, F., Renauld, J. C., Van Cangh, P. J., Boon, T., and Van den Eynde, B. J. (1998). An antigen recognized by autologous CTLs on a human bladder carcinoma. J Immunol 160, 6188-6194.

Herman, J., Jongeneel, V., Kuznetsov, D., and Coulie, P. G. (1999). Differences in the recognition by CTL of peptides presented by the HLA-B*4402 and the HLA-B*4403 molecules which differ by a single amino acid. Tissue Antigens 53, 111-121.

Hocker, T., and Tsao, H. (2007). Ultraviolet radiation and melanoma: a systematic review and analysis of reported sequence variants. Hum Mutat 28, 578-588.

Hodi, F. S., Butler, M., Oble, D. A., Seiden, M. V., Haluska, F. G., Kruse, A., Macrae, S., Nelson, M., Canning, C., Lowy, I., et al. (2008). Immunologic and clinical effects of antibody blockade of cytotoxic T lymphocyte-associated antigen 4 in previously vaccinated cancer patients. Proc Natl Acad Sci USA 105, 3005-3010.

Hodi, F. S., Mihm, M. C., Soiffer, R. J., Haluska, F. G., Butler, M., Seiden, M. V., Davis, T., Henry-Spires, R., MacRae, S., Willman, A., et al. (2003). Biologic activity of cytotoxic T lymphocyte-associated antigen 4 antibody blockade in previously vaccinated metastatic melanoma and ovarian carcinoma patients. Proc Natl Acad Sci USA 100, 4712-4717.

Huang, J., El-Gamil, M., Dudley, M. E., Li, Y. F., Rosenberg, S. A., and Robbins, P. F. (2004). T cells associated with tumor regression recognize frameshifted products of the CDKN2A tumor suppressor gene locus and a mutated HLA class I gene product. J Immunol 172, 6057-6064. Jocham, D., Richter, A., Hoffmann, L., Iwig, K., Fahlenkamp, D., Zakrzewski, G., Schmitt, E., Dannenberg, T., Lehmacher, W., von Wietersheim, J., and Doehn, C. (2004). Adjuvant autologous renal tumour cell vaccine and risk of tumour progression in patients with renal-cell carcinoma after radical nephrectomy: phase III, randomised controlled trial. Lancet 363, 594-599.

Kanzler, H., Barrat, F. J., Hessel, E. M., and Coffman, R. L. (2007). Therapeutic targeting of innate immunity with Toll-like receptor agonists and antagonists. Nat Med 13, 552-559. Keats, J. J., Fonseca, R., Chesi, M., Schop, R., Baker, A., Chng, W. J., Van Wier, S., Tiedemann, R., Shi, C. X., Sebag, M., et al. (2007). Promiscuous mutations activate the noncanonical NF-kappaB pathway in multiple myeloma. Cancer Cell 12, 131-144.

Ladetto, M., Omede, P., Sametti, S., Donovan, J. W., Astolfi, M., Drandi, D., Volpato, F., Giaccone, L., Giaretta, F., Palumbo, A., et al. (2002). Real-time polymerase chain reaction in multiple myeloma: quantitative analysis of tumor contamination of stem cell harvests. Exp Hematol 30, 529-536.

Lennerz, V., Fatho, M., Gentilini, C., Frye, R. A., Lifke, A., Ferel, D., Wolfel, C., Huber, C., and Wolfel, T. (2005).

The response of autologous T cells to a human melanoma is dominated by mutated neoantigens. Proc Natl Acad Sci USA 102, 16013-16018.

Lin, H. H., Ray, S., Tongchusak, S., Reinherz, E., and Brusic, V. (2008). Evaulation of MHC class I peptide binding prediction servers: applications for vaccine research. BMC Bioinformatics (in press).

Maker, A. V., Yang, J. C., Sherry, R. M., Topalian, S. L., Kammula, U. S., Royal, R. E., Hughes, M., Yellin, M. J., Haworth, L. R., Levy, C., et al. (2006). Intrapatient dose escalation of anti-CTLA-4 antibody in patients with metastatic melanoma. J Immunother (1997) 29, 455-463.

Mandelboim, O., Vadai, E., Fridkin, M., Katz-Hillel, A., Feldman, M., Berke, G., and Eisenbach, L. (1995). Regression of established murine carcinoma metastases following vaccination with tumour-associated antigen peptides. Nat Med 1, 1179-1183.

Mandruzzato, S., Brasseur, F., Andry, G., Boon, T., and van der Bruggen, P. (1997). A CASP-8 mutation recognized by cytolytic T lymphocytes on a human head and neck carcinoma. J Exp Med 186, 785-793.

Marijt, W. A., Heemskerk, M. H., Kloosterboer, F. M., Goulmy, E., Kester, M. G., van der Hoorn, M. A., van Luxemburg-Heys, S. A., Hoogeboom, M., Mutis, T., Drijfhout, J. W., et al. (2003). Hematopoiesis-restricted minor histocompatibility antigens HA-1- or HA-2-specific T cells can induce complete remissions of relapsed leukemia. Proc Natl Acad Sci USA 100, 2742-2747.

Marina O, Hainz U, Biernacki M A, et al. (2010) Serologic markers of effective tumor immunity against chronic lymphocytic leukemia include nonmutated B-cell antigens. Cancer Res. 70, 1344-1355.

Mullally, A., and Ritz, J. (2007). Beyond HLA: the significance of genomic variation for allogeneic hematopoietic stem cell transplantation. Blood 109, 1355-1362.

Ofran, Y., Brusic, V., Soiffer, R., Antin, J. H., and Ritz, J. (2008). Identification of human minor histocompatibility antigens (mHa) by combining bioinformatic prediction of peptide epitopes with validation of T cell reactivity in patient blood samples after allogeneic hematopoietic stem cell transplantation. Biol Bone Marrow Transplant 14, 1.

Parmiani, G., De Filippo, A., Novellino, L., and Castelli, C. (2007). Unique human tumor antigens: immunobiology and use in clinical trials. J Immunol 178, 1975-1979.

Pasmant, E., Laurendeau, I., Heron, D., Vidaud, M., Vidaud, D., and Bieche, I. (2007). Characterization of a germ-line deletion, including the entire INK4/ARF locus, in a melanoma-neural system tumor family; identification of ANRIL, an antisense noncoding RNA whose expression coclusters with ARF. Cancer Res 67, 3963-3969.

Peters, B., Sidney, J., Bourne, P., Bui, H. H., Buus, S., Doh, G., Fleri, W., Kronenberg, M., Kubo, R., Lund, O., et al. (2005). The immune epitope database and analysis resource: from vision to blueprint. PLoS Biol 3, e91.

Phan, G. Q., Yang, J. C., Sherry, R. M., Hwu, P., Topalian, S. L., Schwartzentruber, D. J., Restifo, N. P., Haworth, L. R., Seipp, C. A., Freezer, L. J., et al. (2003). Cancer regression and autoimmunity induced by cytotoxic T lymphocyte-associated antigen 4 blockade in patients with metastatic melanoma. Proc Natl Acad Sci USA 100, 8372-8377.

Provan, D., Bartlett-Pandite, L., Zwicky, C., Neuberg, D., Maddocks, A., Corradini, P., Soiffer, R., Ritz, J., Nadler, L. M., and Gribben, J. G. (1996). Eradication of polymerase chain reaction-detectable chronic lymphocytic leukemia cells is associated with improved outcome after bone marrow transplantation. Blood 88, 2228-2235.

Reifenberger, J., Knobbe, C. B., Sterzinger, A. A., Blaschke, B., Schulte, K. W., Ruzicka, T., and Reifenberger, G. (2004). Frequent alterations of Ras signaling pathway genes in sporadic malignant melanomas. Int J Cancer 109, 377-384.

Ribas, A., Camacho, L. H., Lopez-Berestein, G., Pavlov, D., Bulanhagui, C. A., Millham, R., Comin-Anduix, B., Reuben, J. M., Seja, E., Parker, C. A., et al. (2005). Antitumor activity in melanoma and anti-self responses in a phase I trial with the anti-cytotoxic T lymphocyte-associated antigen 4 monoclonal antibody CP-675,206. J Clin Oncol 23, 8968-8977. Robbins, P. F., El-Gamil, M., Li, Y. F., Kawakami, Y., Loftus, D., Appella, E., and Rosenberg, S. A. (1996). A mutated beta-catenin gene encodes a melanoma-specific antigen recognized by tumor infiltrating lymphocytes. J Exp Med 183, 1185-1192.

Rondon, G., Giralt, S., Huh, Y., Khouri, I., Andersson, B., Andreeff, M., and Champlin, R. (1996). Graft-versus-leukemia effect after allogeneic bone marrow transplantation for chronic lymphocytic leukemia. Bone Marrow Transplant 18, 669-672.

Rosenberg, S. A., Yang, J. C., and Restifo, N. P. (2004). Cancer immunotherapy: moving beyond current vaccines. Nat Med 10, 909-915.

Rubinfeld, B., Robbins, P., El-Gamil, M., Albert, I., Porfiri, E., and Polakis, P. (1997). Stabilization of beta-catenin by genetic defects in melanoma cell lines. Science 275, 1790-1792.

Sanderson, K., Scotland, R., Lee, P., Liu, D., Groshen, S., Snively, J., Sian, S., Nichol, G., Davis, T., Keler, T., et al. (2005). Autoimmunity in a phase I trial of a fully human anti-cytotoxic T-lymphocyte antigen-4 monoclonal antibody with multiple melanoma peptides and Montanide ISA 51 for patients with resected stages III and IV melanoma. J Clin Oncol 23, 741-750.

Sato, E., Olson, S. H., Ahn, J., Bundy, B., Nishikawa, H., Qian, F., Jungbluth, A. A., Frosina, D., Gnjatic, S., Ambrosone, C., et al. (2005). Intraepithelial CD8+ tumor-infiltrating lymphocytes and a high CD8+/regulatory T cell ratio are associated with favorable prognosis in ovarian cancer. Proc Natl Acad Sci USA 102, 18538-18543.

Schaffner, C., Stilgenbauer, S., Rappold, G. A., Dohner, H., and Lichter, P. (1999). Somatic ATM mutations indicate a pathogenic role of ATM in B-cell chronic lymphocytic leukemia. Blood 94, 748-753.

Segal, N. H., Parsons, D. W., Peggs, K. S., Velculescu, V., Kinzler, K. W., Vogelstein, B., and Allison, J. P. (2008). Epitope landscape in breast and colorectal cancer. Cancer Res 68, 889-892.

Sensi, M., and Anichini, A. (2006). Unique tumor antigens: evidence for immune control of genome integrity and immunogenic targets for T cell-mediated patient-specific immunotherapy. Clin Cancer Res 12, 5023-5032.

Sjoblom, T., Jones, S., Wood, L. D., Parsons, D. W., Lin, J., Barber, T. D., Mandelker, D., Leary, R. J., Ptak, J., Silliman, N., et al. (2006). The consensus coding sequences of human breast and colorectal cancers. Science 314, 268-274.

Soiffer, R., Hodi, F. S., Haluska, F., Jung, K., Gillessen, S., Singer, S., Tanabe, K., Duda, R., Mentzer, S., Jaklitsch, M., et al. (2003). Vaccination with irradiated, autologous melanoma cells engineered to secrete granulocyte-macrophage colony-stimulating factor by adenoviral-mediated gene transfer augments antitumor immunity in patients with metastatic melanoma. J Clin Oncol 21, 3343-3350.

Soiffer, R., Lynch, T., Mihm, M., Jung, K., Rhuda, C., Schmollinger, J. C., Hodi, F. S., Liebster, L., Lam, P., Mentzer, S., et al. (1998). Vaccination with irradiated autologous melanoma cells engineered to secrete human granulocyte-macrophage colony-stimulating factor generates potent antitumor immunity in patients with metastatic melanoma. Proc Natl Acad Sci USA 95, 13141-13146.

Srivastava, P. K. (2006). Therapeutic cancer vaccines. Curr Opin Immunol 18, 201-205.

Stankovic, T., Hubank, M., Cronin, D., Stewart, G. S., Fletcher, D., Bignell, C. R., Alvi, A. J., Austen, B., Weston, V. J., Fegan, C., et al. (2004). Microarray analysis reveals that TP53- and ATM-mutant B-CLLs share a defect in activating proapoptotic responses after DNA damage but are distinguished by major differences in activating prosurvival responses. Blood 103, 291-300.

Su, Z., Dannull, J., Heiser, A., Yancey, D., Pruitt, S., Madden, J., Coleman, D., Niedzwiecki, D., Gilboa, E., and Vieweg, J. (2003). Immunological and clinical responses in metastatic renal cancer patients vaccinated with tumor RNA-transfected dendritic cells. Cancer Res 63, 2127-2133.

Thomas, R. K., Baker, A. C., Debiasi, R. M., Winckler, W., Laframboise, T., Lin, W. M., Wang, M., Feng, W., Zander, T., MacConaill, L., et al. (2007). High-throughput oncogene mutation profiling in human cancer. Nat Genet 39, 347-351.

Thompson, A. A., Talley, J. A., Do, H. N., Kagan, H. L., Kunkel, L., Berenson, J., Cooper, M. D., Saxon, A., and Wall, R. (1997). Aberrations of the B-cell receptor B29 (CD79b) gene in chronic lymphocytic leukemia. Blood 90, 1387-1394.

Thornton, P. D., Gruszka-Westwood, A. M., Hamoudi, R. A., Atkinson, S., Kaczmarek, P., Morilla, R. M., Hilditch, B. L., A'Hern, R., Matutes, E., and Catovsky, D. (2004). Characterisation of TP53 abnormalities in chronic lymphocytic leukaemia. Hematol J 5, 47-54.

Timmerman, J. M., Czerwinski, D. K., Davis, T. A., Hsu, F. J., Benike, C., Hao, Z. M., Taidi, B., Rajapaksa, R., Caspar, C. B., Okada, C. Y., et al. (2002). Idiotype-pulsed dendritic cell vaccination for B-cell lymphoma: clinical and immune responses in 35 patients. Blood 99, 1517-1526.

Toze, C. L., Galal, A., Barnett, M. J., Shepherd, J. D., Conneally, E. A., Hogge, D. E., Nantel, S. H., Nevill, T. J., Sutherland, H. J., Connors, J. M., et al. (2005). Myeloablative allografting for chronic lymphocytic leukemia: evidence for a potent graft-versus-leukemia effect associated with graft-versus-host disease. Bone Marrow Transplant 36, 825-830.

Ueda, M., Toji, E., and Noda, S. (2007). Germ line and somatic mutations of BRAF V599E in ovarian carcinoma. Int J Gynecol Cancer 17, 794-797.

van der Bruggen, P., Traversari, C., Chomez, P., Lurquin, C., De Plaen, E., Van den Eynde, B., Knuth, A., and Boon, T. (1991). A gene encoding an antigen recognized by cytolytic T lymphocytes on a human melanoma. Science 254, 1643-1647.

Van Pel, A., Georlette, M., and Boon, T. (1979). Tumor cell variants obtained by mutagenesis of a Lewis lung carcinoma cell line: immune rejection by syngeneic mice. Proc Natl Acad Sci U S A 76, 5282-5285.

Van Trappen, P. O., Cullup, T., Troke, R., Swann, D., Shepherd, J. H., Jacobs, I. J., Gayther, S. A., and Mein, C. A. (2007). Somatic mitochondrial DNA mutations in primary and metastatic ovarian cancer. Gynecol Oncol 104, 129-133.

Willmore-Payne, C., Holden, J. A., Tripp, S., and Layfield, L. J. (2005). Human malignant melanoma: detection of BRAF- and c-kit-activating mutations by high-resolution amplicon melting analysis. Hum Pathol 36, 486-493.

Wolfel, T., Hauer, M., Schneider, J., Serrano, M., Wolfel, C., Klehmann-Hieb, E., De Plaen, E., Hankeln, T., Meyer zum Buschenfelde, K. H., and Beach, D. (1995). A p16INK4a-insensitive CDK4 mutant targeted by cytolytic T lymphocytes in a human melanoma. Science 269, 1281-1284.

Wu, C. J., Biernacki, M., Kutok, J. L., Rogers, S., Chen, L., Yang, X. F., Soiffer, R. J., and Ritz, J. (2005). Graft-versus-leukemia target antigens in chronic myelogenous leukemia are expressed on myeloid progenitor cells. Clin Cancer Res 11, 4504-4511.

Wu, C. J., Chillemi, A., Alyea, E. P., Orsini, E., Neuberg, D., Soiffer, R. J., and Ritz, J. (2000a). Reconstitution of T-cell receptor repertoire diversity following T-cell depleted allogeneic bone marrow transplantation is related to hematopoietic chimerism. Blood 95, 352-359.

Wu, C. J., and Ritz, J. (2006). Induction of tumor immunity following allogeneic stem cell transplantation. Adv Immunol 90, 133-173.

Wu, C. J., Yang, X. F., McLaughlin, S., Neuberg, D., Canning, C., Stein, B., Alyea, E. P., Soiffer, R. J., Dranoff, G., and Ritz, J. (2000b). Detection of a potent humoral response associated with immune-induced remission of chronic myelogenous leukemia. J Clin Invest 106, 705-714.

Wu, R., Hendrix-Lucas, N., Kuick, R., Zhai, Y., Schwartz, D. R., Akyol, A., Hanash, S., Misek, D. E., Katabuchi, H., Williams, B. O., et al. (2007). Mouse model of human ovarian endometrioid adenocarcinoma based on somatic defects in the Wnt/beta-catenin and PI3K/Pten signaling pathways. Cancer Cell 11, 321-333.

Yang, X. F., Wu, C. J., McLaughlin, S., Chillemi, A., Wang, K. S., Canning, C., Alyea, E. P., Kantoff, P., Soiffer, R. J., Dranoff, G., and Ritz, J. (2001). CML66, a broadly immunogenic tumor antigen, elicits a humoral immune response associated with remission of chronic myelogenous leukemia. Proc Natl Acad Sci USA 98, 7492-7497.

Zhang, L., Conejo-Garcia, J. R., Katsaros, D., Gimotty, P. A., Massobrio, M., Regnani, G., Makrigiannakis, A., Gray, H., Schlienger, K., Liebman, M. N., et al. (2003). Intratumoral T cells, recurrence, and survival in epithelial ovarian cancer. N Engl J Med 348, 203-213.

Zhang W, Choi J, Zeng W, et al. (2010) Graft-versus-Leukemia Antigen CML66 Elicits Coordinated B-Cell and T-Cell Immunity after Donor Lymphocyte Infusion. Clin Cancer Res. 16, 2729-2739.

Zhou, J., Dudley, M. E., Rosenberg, S. A., and Robbins, P. F. (2005a). Persistence of multiple tumor-specific T-cell clones is associated with complete tumor regression in a melanoma patient receiving adoptive cell transfer therapy. J Immunother (1997) 28, 53-62.

Zhou, X., Jun, D. Y., Thomas, A. M., Huang, X., Huang, L. Q., Mautner, J., Mo, W., Robbins, P. F., Pardoll, D. M., and Jaffee, E. M. (2005b). Diverse CD8+ T-cell responses to renal cell carcinoma antigens in patients treated with an autologous granulocyte-macrophage colony-stimulating factor gene-transduced renal tumor cell vaccine. Cancer Res 65, 1079-1088.

What is claimed:

1. A method of treating cancer in a single subject in need thereof comprising:

(a) comparing:

(i) nucleic acid sequences obtained by whole genome sequencing or whole exome sequencing of cancer cells from the single subject to, (ii) nucleic acid sequences obtained by whole genome sequencing or whole exome sequencing of non-cancer cells from the single subject;

(b) identifying a plurality of cancer specific nucleic acid sequences that are specific to the cancer cells of the single subject based on (a), wherein the identified plurality of cancer specific nucleic acid sequences encodes two or more different peptide sequences of two or more different proteins that are expressed by the cancer cells, and wherein each of the two or more different peptide sequences of the two or more different proteins comprise a cancer specific amino acid mutation that is not present in the non-cancer cells from the single subject;

(c) calculating binding affinities of the two or more different peptide sequences encoded by the plurality of cancer specific nucleic acid sequences identified in (b) to a protein encoded by an HLA allele of the single subject by an HLA peptide binding analysis using a program implemented on a computer system;

(d) selecting at least two peptide sequences calculated in (c) to have a binding affinity to a protein encoded by an HLA allele of the single subject with an $IC_{50}$ of less than 500 nM;

(e) administering a pharmaceutical composition to the single subject, wherein the pharmaceutical composition comprises one or more polypeptides comprising the at least two peptide sequences selected in (d) or one or more polynucleotides encoding the at least two peptide sequences selected in (d).

2. The method of claim 1, wherein the method further comprises formulating the pharmaceutical composition.

3. The method of claim 2, wherein formulating comprises formulating the pharmaceutical composition with an adjuvant.

4. The method of claim 3, wherein the adjuvant comprises poly I:poly C.

5. The method of claim 1, wherein the pharmaceutical composition comprises the one or more polypeptides comprising the at least two peptide sequences selected in (d), and wherein each of the at least two peptide sequences is present in the pharmaceutical composition at an amount of from 50 μg to 1.5 mg.

6. The method of claim 1, wherein a tumor-specific T cell response is induced in the single subject.

7. The method of claim 1, wherein the method further comprises administering an immunostimulatory agent or an anti-immunosuppressive agent.

8. The method of claim 7, wherein the immunostimulatory agent or the anti-immunosuppressive agent is selected from the group consisting of an anti-CTLA-4 agent, an anti-PD1 agent, an anti-PD-L1 agent, an anti-CD25 agent or an indoleamine (2,3)-dioxygenase (IDO) inhibitor.

9. The method of claim 1, wherein (i) each peptide sequences of the one or more polypeptides that comprises a peptide sequence of the at least two peptide sequences selected in (d) has a length of from 8 to 50 naturally occurring amino acids, or (ii) each peptide sequence encoded by the one or more polynucleotides that encodes a peptide sequence of the at least two peptide sequences selected in (d) has a length of from 8 to 50 naturally occurring amino acids.

10. The method of claim 9, wherein (i) each peptide sequence of the one or more polypeptides that comprises a peptide sequence of the at least two peptide sequences selected in (d) is greater than 15 amino acids in length, or (ii) each peptide sequence encoded by the one or more polynucleotides that encodes a peptide sequence of the at least two peptide sequences selected in (d) is greater than 15 amino acids in length.

11. The method of claim 1, wherein (i) a first peptide sequence of the at least two peptide sequences selected in (d) is predicted to bind to a protein encoded by a first HLA allele of the single subject; and (ii) the first peptide sequence or a second peptide sequence of the at least two peptide sequences selected in (d) is predicted to bind to a protein encoded by a second HLA allele of the single subject that is different than the first HLA allele.

12. The method of claim 2, wherein formulating comprises (a) expressing or synthesizing the one or more polypeptides comprising the at least two peptide sequences selected in (d); or (b) producing the one or more polynucleotides encoding the at least two peptide sequences selected in (d).

13. The method of claim 1, wherein the protein encoded by an HLA allele of the single subject is an MHC class I protein, and wherein each of the at least two peptide sequences selected in (d) has a length of from 8 to 12 naturally occurring amino acids.

14. The method of claim 1, wherein the cancer specific amino acid mutation that is not present in the non-cancer cells from the single subject is encoded by a frameshift mutation.

15. The method of claim 1, wherein selecting comprises selecting at least one peptide sequences calculated in (c) to have a binding affinity to a protein encoded by an HLA allele of the single subject with an $IC_{50}$ of less than 100 nM.

16. The method of claim 1, wherein the at least two peptide sequences selected in (d) comprises at most 20 peptide sequences.

17. The method of claim 1, wherein the at least two peptide sequences selected in (d) comprises at least 4 peptide sequences for administration.

18. The method of claim 1, wherein identifying comprises identifying the two or more different proteins that are expressed by cancer cells of the single subject by measuring levels of RNA encoding the two or more different proteins in the cancer cells of the single subject.

19. The method of claim 1, wherein (i) an affinity of one or more of the at least two peptide sequences selected in (d) to the protein encoded by an HLA allele of the single subject is not calculated prior to administering, or (ii) an affinity of T cells of the single subject to a complex of a peptide sequence of the at least two peptide sequences selected in (d) and a protein encoded by an HLA allele of the single subject is not calculated prior to administering.

20. The method of claim 1, wherein the cancer cells of the subject are cancer cells of a solid cancer.

* * * * *

SEQUENCE LISTING

<160> NUMBER OF SEQ ID NOS: 21

<210> SEQ ID NO 1
<211> LENGTH: 1304
<212> TYPE: PRT
<213> ORGANISM: Homo sapiens

<400> SEQUENCE: 1

```
Met Ala Lys Ile Ala Lys Thr His Glu Asp Ile Glu Ala Gln Ile Arg
1               5                   10                  15

Glu Ile Gln Gly Lys Lys Ala Ala Leu Asp Glu Ala Gln Gly Val Gly
            20                  25                  30

Leu Asp Ser Thr Gly Tyr Tyr Asp Gln Glu Ile Tyr Gly Gly Ser Asp
        35                  40                  45

Ser Arg Phe Ala Gly Tyr Val Thr Ser Ile Ala Ala Thr Glu Leu Glu
    50                  55                  60

Asp Asp Asp Asp Asp Tyr Ser Ser Ser Thr Ser Leu Leu Gly Gln Lys
65                  70                  75                  80

Lys Pro Gly Tyr His Ala Pro Val Ala Leu Leu Asn Asp Ile Pro Gln
                85                  90                  95

Ser Thr Glu Gln Tyr Asp Pro Phe Ala Glu His Arg Pro Pro Lys Ile
            100                 105                 110

Ala Asp Arg Glu Asp Glu Tyr Lys Lys His Arg Arg Thr Met Ile Ile
        115                 120                 125

Ser Pro Glu Arg Leu Asp Pro Phe Ala Asp Gly Gly Lys Thr Pro Asp
    130                 135                 140

Pro Lys Met Asn Ala Arg Thr Tyr Met Asp Val Met Arg Glu Gln His
145                 150                 155                 160

Leu Thr Lys Glu Glu Arg Glu Ile Arg Gln Gln Leu Ala Glu Lys Ala
                165                 170                 175

Lys Ala Gly Glu Leu Lys Val Val Asn Gly Ala Ala Ala Ser Gln Pro
            180                 185                 190

Pro Ser Lys Arg Lys Arg Arg Trp Asp Gln Thr Ala Asp Gln Thr Pro
        195                 200                 205

Gly Ala Thr Pro Lys Lys Leu Ser Ser Trp Asp Gln Ala Glu Thr Pro
    210                 215                 220

Gly His Thr Pro Ser Leu Arg Trp Asp Glu Thr Pro Gly Arg Ala Lys
225                 230                 235                 240

Gly Ser Glu Thr Pro Gly Ala Thr Pro Gly Ser Lys Ile Trp Asp Pro
                245                 250                 255

Thr Pro Ser His Thr Pro Ala Gly Ala Ala Thr Pro Gly Arg Gly Asp
            260                 265                 270

Thr Pro Gly His Ala Thr Pro Gly His Gly Gly Ala Thr Ser Ser Ala
        275                 280                 285

Arg Lys Asn Arg Trp Asp Glu Thr Pro Lys Thr Glu Arg Asp Thr Pro
    290                 295                 300

Gly His Gly Ser Gly Trp Ala Glu Thr Pro Arg Thr Asp Arg Gly Gly
305                 310                 315                 320

Asp Ser Ile Gly Glu Thr Pro Thr Pro Gly Ala Ser Lys Arg Lys Ser
                325                 330                 335

Arg Trp Asp Glu Thr Pro Ala Ser Gln Met Gly Gly Ser Thr Pro Val
            340                 345                 350

Leu Thr Pro Gly Lys Thr Pro Ile Gly Thr Pro Ala Met Asn Met Ala
        355                 360                 365
```

```
Thr Pro Thr Pro Gly His Ile Met Ser Met Thr Pro Glu Gln Leu Gln
    370                 375                 380

Ala Trp Arg Trp Glu Arg Glu Ile Asp Glu Arg Asn Arg Pro Leu Ser
385                 390                 395                 400

Asp Glu Glu Leu Asp Ala Met Phe Pro Glu Gly Tyr Lys Val Leu Pro
                405                 410                 415

Pro Pro Ala Gly Tyr Val Pro Ile Arg Thr Pro Ala Arg Lys Leu Thr
            420                 425                 430

Ala Thr Pro Thr Pro Leu Gly Gly Met Thr Gly Phe His Met Gln Thr
        435                 440                 445

Glu Asp Arg Thr Met Lys Ser Val Asn Asp Gln Pro Ser Gly Asn Leu
    450                 455                 460

Pro Phe Leu Lys Pro Asp Asp Ile Gln Tyr Phe Asp Lys Leu Leu Val
465                 470                 475                 480

Asp Val Asp Glu Ser Thr Leu Ser Pro Glu Glu Gln Lys Glu Arg Lys
                485                 490                 495

Ile Met Lys Leu Leu Leu Lys Ile Lys Asn Gly Thr Pro Pro Met Arg
            500                 505                 510

Lys Ala Ala Leu Arg Gln Ile Thr Asp Lys Ala Arg Glu Phe Gly Ala
        515                 520                 525

Gly Pro Leu Phe Asn Gln Ile Leu Pro Leu Leu Met Ser Pro Thr Leu
    530                 535                 540

Glu Asp Gln Glu Arg His Leu Leu Val Lys Val Ile Asp Arg Ile Leu
545                 550                 555                 560

Tyr Lys Leu Asp Asp Leu Val Arg Pro Tyr Val His Lys Ile Leu Val
                565                 570                 575

Val Ile Glu Pro Leu Leu Ile Asp Glu Asp Tyr Tyr Ala Arg Val Glu
            580                 585                 590

Gly Arg Glu Ile Ile Ser Asn Leu Ala Lys Ala Ala Gly Leu Ala Thr
        595                 600                 605

Met Ile Ser Thr Met Arg Pro Asp Ile Asp Asn Met Asp Glu Tyr Val
    610                 615                 620

Arg Asn Thr Thr Ala Arg Ala Phe Ala Val Val Ala Ser Ala Leu Gly
625                 630                 635                 640

Ile Pro Ser Leu Leu Pro Phe Leu Lys Ala Val Cys Lys Ser Lys Lys
                645                 650                 655

Ser Trp Gln Ala Arg His Thr Gly Ile Lys Ile Val Gln Gln Ile Ala
            660                 665                 670

Ile Leu Met Gly Cys Ala Ile Leu Pro His Leu Arg Ser Leu Val Glu
        675                 680                 685

Ile Ile Glu His Gly Leu Val Asp Glu Gln Gln Lys Val Arg Thr Ile
    690                 695                 700

Ser Ala Leu Ala Ile Ala Ala Leu Ala Glu Ala Ala Thr Pro Tyr Gly
705                 710                 715                 720

Ile Glu Ser Phe Asp Ser Val Leu Lys Pro Leu Trp Lys Gly Ile Arg
                725                 730                 735

Gln His Arg Gly Lys Gly Leu Ala Ala Phe Leu Lys Ala Ile Gly Tyr
            740                 745                 750

Leu Ile Pro Leu Met Asp Ala Glu Tyr Ala Asn Tyr Tyr Thr Arg Glu
        755                 760                 765

Val Met Leu Ile Leu Ile Arg Glu Phe Gln Ser Pro Asp Glu Glu Met
    770                 775                 780

Lys Lys Ile Val Leu Lys Val Val Lys Gln Cys Cys Gly Thr Asp Gly
```

```
785                 790                 795                 800

Val Glu Ala Asn Tyr Ile Lys Thr Glu Ile Leu Pro Pro Phe Phe Lys
                805                 810                 815

His Phe Trp Gln His Arg Met Ala Leu Asp Arg Arg Asn Tyr Arg Gln
            820                 825                 830

Leu Val Asp Thr Thr Val Glu Leu Ala Asn Lys Val Gly Ala Ala Glu
        835                 840                 845

Ile Ile Ser Arg Ile Val Asp Asp Leu Lys Asp Glu Ala Glu Gln Tyr
    850                 855                 860

Arg Lys Met Val Met Glu Thr Ile Glu Lys Ile Met Gly Asn Leu Gly
865                 870                 875                 880

Ala Ala Asp Ile Asp His Lys Leu Glu Glu Gln Leu Ile Asp Gly Ile
                885                 890                 895

Leu Tyr Ala Phe Gln Glu Gln Thr Thr Glu Asp Ser Val Met Leu Asn
            900                 905                 910

Gly Phe Gly Thr Val Val Asn Ala Leu Gly Lys Arg Val Lys Pro Tyr
        915                 920                 925

Leu Pro Gln Ile Cys Gly Thr Val Leu Trp Arg Leu Asn Asn Lys Ser
    930                 935                 940

Ala Lys Val Arg Gln Gln Ala Ala Asp Leu Ile Ser Arg Thr Ala Val
945                 950                 955                 960

Val Met Lys Thr Cys Gln Glu Glu Lys Leu Met Gly His Leu Gly Val
                965                 970                 975

Val Leu Tyr Glu Tyr Leu Gly Glu Glu Tyr Pro Glu Val Leu Gly Ser
            980                 985                 990

Ile Leu Gly Ala Leu Lys Ala Ile  Val Asn Val Ile Gly  Met His Lys
        995                 1000                1005

Met Thr  Pro Pro Ile Lys Asp  Leu Leu Pro Arg Leu  Thr Pro Ile
    1010                1015                1020

Leu Lys  Asn Arg His Glu Lys  Val Gln Glu Asn Cys  Ile Asp Leu
    1025                1030                1035

Val Gly  Arg Ile Ala Asp Arg  Gly Ala Glu Tyr Val  Ser Ala Arg
    1040                1045                1050

Glu Trp  Met Arg Ile Cys Phe  Glu Leu Leu Glu Leu  Leu Lys Ala
    1055                1060                1065

His Lys  Lys Ala Ile Arg Arg  Ala Thr Val Asn Thr  Phe Gly Tyr
    1070                1075                1080

Ile Ala  Lys Ala Ile Gly Pro  His Asp Val Leu Ala  Thr Leu Leu
    1085                1090                1095

Asn Asn  Leu Lys Val Gln Glu  Arg Gln Asn Arg Val  Cys Thr Thr
    1100                1105                1110

Val Ala  Ile Ala Ile Val Ala  Glu Thr Cys Ser Pro  Phe Thr Val
    1115                1120                1125

Leu Pro  Ala Leu Met Asn Glu  Tyr Arg Val Pro Glu  Leu Asn Val
    1130                1135                1140

Gln Asn  Gly Val Leu Lys Ser  Leu Ser Phe Leu Phe  Glu Tyr Ile
    1145                1150                1155

Gly Glu  Met Gly Lys Asp Tyr  Ile Tyr Ala Val Thr  Pro Leu Leu
    1160                1165                1170

Glu Asp  Ala Leu Met Asp Arg  Asp Leu Val His Arg  Gln Thr Ala
    1175                1180                1185

Ser Ala  Val Val Gln His Met  Ser Leu Gly Val Tyr  Gly Phe Gly
    1190                1195                1200
```

```
Cys Glu  Asp Ser Leu Asn His  Leu Leu Asn Tyr Val  Trp Pro Asn
    1205                 1210                 1215

Val Phe  Glu Thr Ser Pro His  Val Ile Gln Ala Val  Met Gly Ala
    1220                 1225                 1230

Leu Glu  Gly Leu Arg Val Ala  Ile Gly Pro Cys Arg  Met Leu Gln
    1235                 1240                 1245

Tyr Cys  Leu Gln Gly Leu Phe  His Pro Ala Arg Lys  Val Arg Asp
    1250                 1255                 1260

Val Tyr  Trp Lys Ile Tyr Asn  Ser Ile Tyr Ile Gly  Ser Gln Asp
    1265                 1270                 1275

Ala Leu  Ile Ala His Tyr Pro  Arg Ile Tyr Asn Asp  Asp Lys Asn
    1280                 1285                 1290

Thr Tyr  Ile Arg Tyr Glu Leu  Asp Tyr Ile Leu
    1295                 1300


<210> SEQ ID NO 2
<211> LENGTH: 309
<212> TYPE: PRT
<213> ORGANISM: Homo sapiens

<400> SEQUENCE: 2

Met Arg Pro Asp Arg Ala Glu Ala Pro Gly Pro Pro Ala Met Ala Ala
1               5                   10                  15

Gly Gly Pro Gly Ala Gly Ser Ala Ala Pro Val Ser Ser Thr Ser Ser
            20                  25                  30

Leu Pro Leu Ala Ala Leu Asn Met Arg Val Arg Arg Arg Leu Ser Leu
        35                  40                  45

Phe Leu Asn Val Arg Thr Gln Val Ala Ala Asp Trp Thr Ala Leu Ala
    50                  55                  60

Glu Glu Met Asp Phe Glu Tyr Leu Glu Ile Arg Gln Leu Glu Thr Gln
65                  70                  75                  80

Ala Asp Pro Thr Gly Arg Leu Leu Asp Ala Trp Gln Gly Arg Pro Gly
                85                  90                  95

Ala Ser Val Gly Arg Leu Leu Glu Leu Leu Thr Lys Leu Gly Arg Asp
            100                 105                 110

Asp Val Leu Leu Glu Leu Gly Pro Ser Ile Glu Glu Asp Cys Gln Lys
        115                 120                 125

Tyr Ile Leu Lys Gln Gln Gln Glu Glu Ala Glu Lys Pro Leu Gln Val
    130                 135                 140

Ala Ala Val Asp Ser Ser Val Pro Arg Thr Ala Glu Leu Ala Gly Ile
145                 150                 155                 160

Thr Thr Leu Asp Asp Pro Leu Gly His Met Pro Glu Arg Phe Asp Ala
                165                 170                 175

Phe Ile Cys Tyr Cys Pro Ser Asp Ile Gln Phe Val Gln Glu Met Ile
            180                 185                 190

Arg Gln Leu Glu Gln Thr Asn Tyr Arg Leu Lys Leu Cys Val Ser Asp
        195                 200                 205

Arg Asp Val Leu Pro Gly Thr Cys Val Trp Ser Ile Ala Ser Glu Leu
    210                 215                 220

Ile Glu Lys Arg Cys Arg Arg Met Val Val Val Val Ser Asp Asp Tyr
225                 230                 235                 240

Leu Gln Ser Lys Glu Cys Asp Phe Gln Thr Lys Phe Ala Leu Ser Leu
                245                 250                 255

Ser Pro Gly Ala His Gln Lys Arg Leu Ile Pro Ile Lys Tyr Lys Ala
```

```
            260                 265                 270

Met Lys Lys Glu Phe Pro Ser Ile Leu Arg Phe Ile Thr Val Cys Asp
        275                 280                 285

Tyr Thr Asn Pro Cys Thr Lys Ser Trp Phe Trp Thr Arg Leu Ala Lys
    290                 295                 300

Ala Leu Ser Leu Pro
305


<210> SEQ ID NO 3
<211> LENGTH: 393
<212> TYPE: PRT
<213> ORGANISM: Homo sapiens

<400> SEQUENCE: 3

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320
```

```
Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390


<210> SEQ ID NO 4
<211> LENGTH: 3056
<212> TYPE: PRT
<213> ORGANISM: Homo sapiens

<400> SEQUENCE: 4

Met Ser Leu Val Leu Asn Asp Leu Leu Ile Cys Cys Arg Gln Leu Glu
1               5                   10                  15

His Asp Arg Ala Thr Glu Arg Lys Lys Glu Val Glu Lys Phe Lys Arg
            20                  25                  30

Leu Ile Arg Asp Pro Glu Thr Ile Lys His Leu Asp Arg His Ser Asp
        35                  40                  45

Ser Lys Gln Gly Lys Tyr Leu Asn Trp Asp Ala Val Phe Arg Phe Leu
    50                  55                  60

Gln Lys Tyr Ile Gln Lys Glu Thr Glu Cys Leu Arg Ile Ala Lys Pro
65                  70                  75                  80

Asn Val Ser Ala Ser Thr Gln Ala Ser Arg Gln Lys Lys Met Gln Glu
                85                  90                  95

Ile Ser Ser Leu Val Lys Tyr Phe Ile Lys Cys Ala Asn Arg Arg Ala
            100                 105                 110

Pro Arg Leu Lys Cys Gln Glu Leu Leu Asn Tyr Ile Met Asp Thr Val
        115                 120                 125

Lys Asp Ser Ser Asn Gly Ala Ile Tyr Gly Ala Asp Cys Ser Asn Ile
    130                 135                 140

Leu Leu Lys Asp Ile Leu Ser Val Arg Lys Tyr Trp Cys Glu Ile Ser
145                 150                 155                 160

Gln Gln Gln Trp Leu Glu Leu Phe Ser Val Tyr Phe Arg Leu Tyr Leu
                165                 170                 175

Lys Pro Ser Gln Asp Val His Arg Val Leu Val Ala Arg Ile Ile His
            180                 185                 190

Ala Val Thr Lys Gly Cys Cys Ser Gln Thr Asp Gly Leu Asn Ser Lys
        195                 200                 205

Phe Leu Asp Phe Phe Ser Lys Ala Ile Gln Cys Ala Arg Gln Glu Lys
    210                 215                 220

Ser Ser Ser Gly Leu Asn His Ile Leu Ala Ala Leu Thr Ile Phe Leu
225                 230                 235                 240

Lys Thr Leu Ala Val Asn Phe Arg Ile Arg Val Cys Glu Leu Gly Asp
                245                 250                 255

Glu Ile Leu Pro Thr Leu Leu Tyr Ile Trp Thr Gln His Arg Leu Asn
            260                 265                 270

Asp Ser Leu Lys Glu Val Ile Ile Glu Leu Phe Gln Leu Gln Ile Tyr
        275                 280                 285

Ile His His Pro Lys Gly Ala Lys Thr Gln Glu Lys Gly Ala Tyr Glu
    290                 295                 300
```

```
Ser Thr Lys Trp Arg Ser Ile Leu Tyr Asn Leu Tyr Asp Leu Leu Val
305                 310                 315                 320

Asn Glu Ile Ser His Ile Gly Ser Arg Gly Lys Tyr Ser Ser Gly Phe
                325                 330                 335

Arg Asn Ile Ala Val Lys Glu Asn Leu Ile Glu Leu Met Ala Asp Ile
            340                 345                 350

Cys His Gln Val Phe Asn Glu Asp Thr Arg Ser Leu Glu Ile Ser Gln
        355                 360                 365

Ser Tyr Thr Thr Thr Gln Arg Glu Ser Ser Asp Tyr Ser Val Pro Cys
    370                 375                 380

Lys Arg Lys Lys Ile Glu Leu Gly Trp Glu Val Ile Lys Asp His Leu
385                 390                 395                 400

Gln Lys Ser Gln Asn Asp Phe Asp Leu Val Pro Trp Leu Gln Ile Ala
                405                 410                 415

Thr Gln Leu Ile Ser Lys Tyr Pro Ala Ser Leu Pro Asn Cys Glu Leu
            420                 425                 430

Ser Pro Leu Leu Met Ile Leu Ser Gln Leu Leu Pro Gln Gln Arg His
        435                 440                 445

Gly Glu Arg Thr Pro Tyr Val Leu Arg Cys Leu Thr Glu Val Ala Leu
    450                 455                 460

Cys Gln Asp Lys Arg Ser Asn Leu Glu Ser Ser Gln Lys Ser Asp Leu
465                 470                 475                 480

Leu Lys Leu Trp Asn Lys Ile Trp Cys Ile Thr Phe Arg Gly Ile Ser
                485                 490                 495

Ser Glu Gln Ile Gln Ala Glu Asn Phe Gly Leu Leu Gly Ala Ile Ile
            500                 505                 510

Gln Gly Ser Leu Val Glu Val Asp Arg Glu Phe Trp Lys Leu Phe Thr
        515                 520                 525

Gly Ser Ala Cys Arg Pro Ser Cys Pro Ala Val Cys Cys Leu Thr Leu
    530                 535                 540

Ala Leu Thr Thr Ser Ile Val Pro Gly Thr Val Lys Met Gly Ile Glu
545                 550                 555                 560

Gln Asn Met Cys Glu Val Asn Arg Ser Phe Ser Leu Lys Glu Ser Ile
                565                 570                 575

Met Lys Trp Leu Leu Phe Tyr Gln Leu Glu Gly Asp Leu Glu Asn Ser
            580                 585                 590

Thr Glu Val Pro Pro Ile Leu His Ser Asn Phe Pro His Leu Val Leu
        595                 600                 605

Glu Lys Ile Leu Val Ser Leu Thr Met Lys Asn Cys Lys Ala Ala Met
    610                 615                 620

Asn Phe Phe Gln Ser Val Pro Glu Cys Glu His His Gln Lys Asp Lys
625                 630                 635                 640

Glu Glu Leu Ser Phe Ser Glu Val Glu Glu Leu Phe Leu Gln Thr Thr
                645                 650                 655

Phe Asp Lys Met Asp Phe Leu Thr Ile Val Arg Glu Cys Gly Ile Glu
            660                 665                 670

Lys His Gln Ser Ser Ile Gly Phe Ser Val His Gln Asn Leu Lys Glu
        675                 680                 685

Ser Leu Asp Arg Cys Leu Leu Gly Leu Ser Glu Gln Leu Leu Asn Asn
    690                 695                 700

Tyr Ser Ser Glu Ile Thr Asn Ser Glu Thr Leu Val Arg Cys Ser Arg
705                 710                 715                 720
```

```
Leu Leu Val Gly Val Leu Gly Cys Tyr Cys Tyr Met Gly Val Ile Ala
                725                 730                 735

Glu Glu Glu Ala Tyr Lys Ser Glu Leu Phe Gln Lys Ala Lys Ser Leu
            740                 745                 750

Met Gln Cys Ala Gly Glu Ser Ile Thr Leu Phe Lys Asn Lys Thr Asn
        755                 760                 765

Glu Glu Phe Arg Ile Gly Ser Leu Arg Asn Met Met Gln Leu Cys Thr
    770                 775                 780

Arg Cys Leu Ser Asn Cys Thr Lys Lys Ser Pro Asn Lys Ile Ala Ser
785                 790                 795                 800

Gly Phe Phe Leu Arg Leu Leu Thr Ser Lys Leu Met Asn Asp Ile Ala
                805                 810                 815

Asp Ile Cys Lys Ser Leu Ala Ser Phe Ile Lys Lys Pro Phe Asp Arg
            820                 825                 830

Gly Glu Val Glu Ser Met Glu Asp Asp Thr Asn Gly Asn Leu Met Glu
        835                 840                 845

Val Glu Asp Gln Ser Ser Met Asn Leu Phe Asn Asp Tyr Pro Asp Ser
    850                 855                 860

Ser Val Ser Asp Ala Asn Glu Pro Gly Glu Ser Gln Ser Thr Ile Gly
865                 870                 875                 880

Ala Ile Asn Pro Leu Ala Glu Glu Tyr Leu Ser Lys Gln Asp Leu Leu
                885                 890                 895

Phe Leu Asp Met Leu Lys Phe Leu Cys Leu Cys Val Thr Thr Ala Gln
            900                 905                 910

Thr Asn Thr Val Ser Phe Arg Ala Ala Asp Ile Arg Arg Lys Leu Leu
        915                 920                 925

Met Leu Ile Asp Ser Ser Thr Leu Glu Pro Thr Lys Ser Leu His Leu
    930                 935                 940

His Met Tyr Leu Met Leu Leu Lys Glu Leu Pro Gly Glu Glu Tyr Pro
945                 950                 955                 960

Leu Pro Met Glu Asp Val Leu Glu Leu Leu Lys Pro Leu Ser Asn Val
                965                 970                 975

Cys Ser Leu Tyr Arg Arg Asp Gln Asp Val Cys Lys Thr Ile Leu Asn
            980                 985                 990

His Val Leu His Val Val Lys Asn  Leu Gly Gln Ser Asn  Met Asp Ser
        995                 1000                1005

Glu Asn  Thr Arg Asp Ala Gln  Gly Gln Phe Leu Thr  Val Ile Gly
    1010                1015                1020

Ala Phe  Trp His Leu Thr Lys  Glu Arg Lys Tyr Ile  Phe Ser Val
    1025                1030                1035

Arg Met  Ala Leu Val Asn Cys  Leu Lys Thr Leu Leu  Glu Ala Asp
    1040                1045                1050

Pro Tyr  Ser Lys Trp Ala Ile  Leu Asn Val Met Gly  Lys Asp Phe
    1055                1060                1065

Pro Val  Asn Glu Val Phe Thr  Gln Phe Leu Ala Asp  Asn His His
    1070                1075                1080

Gln Val  Arg Met Leu Ala Ala  Glu Ser Ile Asn Arg  Leu Phe Gln
    1085                1090                1095

Asp Thr  Lys Gly Asp Ser Ser  Arg Leu Leu Lys Ala  Leu Pro Leu
    1100                1105                1110

Lys Leu  Gln Gln Thr Ala Phe  Glu Asn Ala Tyr Leu  Lys Ala Gln
    1115                1120                1125

Glu Gly  Met Arg Glu Met Ser  His Ser Ala Glu Asn  Pro Glu Thr
```

```
    1130                1135                1140

Leu Asp  Glu Ile Tyr Asn Arg  Lys Ser Val Leu Leu  Thr Leu Ile
    1145                1150                1155

Ala Val  Val Leu Ser Cys Ser  Pro Ile Cys Glu Lys  Gln Ala Leu
    1160                1165                1170

Phe Ala  Leu Cys Lys Ser Val  Lys Glu Asn Gly Leu  Glu Pro His
    1175                1180                1185

Leu Val  Lys Lys Val Leu Glu  Lys Val Ser Glu Thr  Phe Gly Tyr
    1190                1195                1200

Arg Arg  Leu Glu Asp Phe Met  Ala Ser His Leu Asp  Tyr Leu Val
    1205                1210                1215

Leu Glu  Trp Leu Asn Leu Gln  Asp Thr Glu Tyr Asn  Leu Ser Ser
    1220                1225                1230

Phe Pro  Phe Ile Leu Leu Asn  Tyr Thr Asn Ile Glu  Asp Phe Tyr
    1235                1240                1245

Arg Ser  Cys Tyr Lys Val Leu  Ile Pro His Leu Val  Ile Arg Ser
    1250                1255                1260

His Phe  Asp Glu Val Lys Ser  Ile Ala Asn Gln Ile  Gln Glu Asp
    1265                1270                1275

Trp Lys  Ser Leu Leu Thr Asp  Cys Phe Pro Lys Ile  Leu Val Asn
    1280                1285                1290

Ile Leu  Pro Tyr Phe Ala Tyr  Glu Gly Thr Arg Asp  Ser Gly Met
    1295                1300                1305

Ala Gln  Gln Arg Glu Thr Ala  Thr Lys Val Tyr Asp  Met Leu Lys
    1310                1315                1320

Ser Glu  Asn Leu Leu Gly Lys  Gln Ile Asp His Leu  Phe Ile Ser
    1325                1330                1335

Asn Leu  Pro Glu Ile Val Val  Glu Leu Leu Met Thr  Leu His Glu
    1340                1345                1350

Pro Ala  Asn Ser Ser Ala Ser  Gln Ser Thr Asp Leu  Cys Asp Phe
    1355                1360                1365

Ser Gly  Asp Leu Asp Pro Ala  Pro Asn Pro Pro His  Phe Pro Ser
    1370                1375                1380

His Val  Ile Lys Ala Thr Phe  Ala Tyr Ile Ser Asn  Cys His Lys
    1385                1390                1395

Thr Lys  Leu Lys Ser Ile Leu  Glu Ile Leu Ser Lys  Ser Pro Asp
    1400                1405                1410

Ser Tyr  Gln Lys Ile Leu Leu  Ala Ile Cys Glu Gln  Ala Ala Glu
    1415                1420                1425

Thr Asn  Asn Val Tyr Lys Lys  His Arg Ile Leu Lys  Ile Tyr His
    1430                1435                1440

Leu Phe  Val Ser Leu Leu Leu  Lys Asp Ile Lys Ser  Gly Leu Gly
    1445                1450                1455

Gly Ala  Trp Ala Phe Val Leu  Arg Asp Val Ile Tyr  Thr Leu Ile
    1460                1465                1470

His Tyr  Ile Asn Gln Arg Pro  Ser Cys Ile Met Asp  Val Ser Leu
    1475                1480                1485

Arg Ser  Phe Ser Leu Cys Cys  Asp Leu Leu Ser Gln  Val Cys Gln
    1490                1495                1500

Thr Ala  Val Thr Tyr Cys Lys  Asp Ala Leu Glu Asn  His Leu His
    1505                1510                1515

Val Ile  Val Gly Thr Leu Ile  Pro Leu Val Tyr Glu  Gln Val Glu
    1520                1525                1530
```

```
Val Gln  Lys Gln Val Leu Asp  Leu Leu Lys Tyr Leu  Val Ile Asp
    1535                 1540                 1545

Asn Lys  Asp Asn Glu Asn Leu  Tyr Ile Thr Ile Lys  Leu Leu Asp
    1550                 1555                 1560

Pro Phe  Pro Asp His Val Val  Phe Lys Asp Leu Arg  Ile Thr Gln
    1565                 1570                 1575

Gln Lys  Ile Lys Tyr Ser Arg  Gly Pro Phe Ser Leu  Leu Glu Glu
    1580                 1585                 1590

Ile Asn  His Phe Leu Ser Val  Ser Val Tyr Asp Ala  Leu Pro Leu
    1595                 1600                 1605

Thr Arg  Leu Glu Gly Leu Lys  Asp Leu Arg Arg Gln  Leu Glu Leu
    1610                 1615                 1620

His Lys  Asp Gln Met Val Asp  Ile Met Arg Ala Ser  Gln Asp Asn
    1625                 1630                 1635

Pro Gln  Asp Gly Ile Met Val  Lys Leu Val Val Asn  Leu Leu Gln
    1640                 1645                 1650

Leu Ser  Lys Met Ala Ile Asn  His Thr Gly Glu Lys  Glu Val Leu
    1655                 1660                 1665

Glu Ala  Val Gly Ser Cys Leu  Gly Glu Val Gly Pro  Ile Asp Phe
    1670                 1675                 1680

Ser Thr  Ile Ala Ile Gln His  Ser Lys Asp Ala Ser  Tyr Thr Lys
    1685                 1690                 1695

Ala Leu  Lys Leu Phe Glu Asp  Lys Glu Leu Gln Trp  Thr Phe Ile
    1700                 1705                 1710

Met Leu  Thr Tyr Leu Asn Asn  Thr Leu Val Glu Asp  Cys Val Lys
    1715                 1720                 1725

Val Arg  Ser Ala Ala Val Thr  Cys Leu Lys Asn Ile  Leu Ala Thr
    1730                 1735                 1740

Lys Thr  Gly His Ser Phe Trp  Glu Ile Tyr Lys Met  Thr Thr Asp
    1745                 1750                 1755

Pro Met  Leu Ala Tyr Leu Gln  Pro Phe Arg Thr Ser  Arg Lys Lys
    1760                 1765                 1770

Phe Leu  Glu Val Pro Arg Phe  Asp Lys Glu Asn Pro  Phe Glu Gly
    1775                 1780                 1785

Leu Asp  Asp Ile Asn Leu Trp  Ile Pro Leu Ser Glu  Asn His Asp
    1790                 1795                 1800

Ile Trp  Ile Lys Thr Leu Thr  Cys Ala Phe Leu Asp  Ser Gly Gly
    1805                 1810                 1815

Thr Lys  Cys Glu Ile Leu Gln  Leu Leu Lys Pro Met  Cys Glu Val
    1820                 1825                 1830

Lys Thr  Asp Phe Cys Gln Thr  Val Leu Pro Tyr Leu  Ile His Asp
    1835                 1840                 1845

Ile Leu  Leu Gln Asp Thr Asn  Glu Ser Trp Arg Asn  Leu Leu Ser
    1850                 1855                 1860

Thr His  Val Gln Gly Phe Phe  Thr Ser Cys Leu Arg  His Phe Ser
    1865                 1870                 1875

Gln Thr  Ser Arg Ser Thr Thr  Pro Ala Asn Leu Asp  Ser Glu Ser
    1880                 1885                 1890

Glu His  Phe Phe Arg Cys Cys  Leu Asp Lys Lys Ser  Gln Arg Thr
    1895                 1900                 1905

Met Leu  Ala Val Val Asp Tyr  Met Arg Arg Gln Lys  Arg Pro Ser
    1910                 1915                 1920
```

-continued

```
Ser Gly  Thr Ile Phe Asn Asp  Ala Phe Trp Leu Asp  Leu Asn Tyr
    1925                 1930                 1935

Leu Glu  Val Ala Lys Val Ala  Gln Ser Cys Ala Ala  His Phe Thr
    1940                 1945                 1950

Ala Leu  Leu Tyr Ala Glu Ile  Tyr Ala Asp Lys Lys  Ser Met Asp
    1955                 1960                 1965

Asp Gln  Glu Lys Arg Ser Leu  Ala Phe Glu Glu Gly  Ser Gln Ser
    1970                 1975                 1980

Thr Thr  Ile Ser Ser Leu Ser  Glu Lys Ser Lys Glu  Glu Thr Gly
    1985                 1990                 1995

Ile Ser  Leu Gln Asp Leu Leu  Leu Glu Ile Tyr Arg  Ser Ile Gly
    2000                 2005                 2010

Glu Pro  Asp Ser Leu Tyr Gly  Cys Gly Gly Gly Lys  Met Leu Gln
    2015                 2020                 2025

Pro Ile  Thr Arg Leu Arg Thr  Tyr Glu His Glu Ala  Met Trp Gly
    2030                 2035                 2040

Lys Ala  Leu Val Thr Tyr Asp  Leu Glu Thr Ala Ile  Pro Ser Ser
    2045                 2050                 2055

Thr Arg  Gln Ala Gly Ile Ile  Gln Ala Leu Gln Asn  Leu Gly Leu
    2060                 2065                 2070

Cys His  Ile Leu Ser Val Tyr  Leu Lys Gly Leu Asp  Tyr Glu Asn
    2075                 2080                 2085

Lys Asp  Trp Cys Pro Glu Leu  Glu Glu Leu His Tyr  Gln Ala Ala
    2090                 2095                 2100

Trp Arg  Asn Met Gln Trp Asp  His Cys Thr Ser Val  Ser Lys Glu
    2105                 2110                 2115

Val Glu  Gly Thr Ser Tyr His  Glu Ser Leu Tyr Asn  Ala Leu Gln
    2120                 2125                 2130

Ser Leu  Arg Asp Arg Glu Phe  Ser Thr Phe Tyr Glu  Ser Leu Lys
    2135                 2140                 2145

Tyr Ala  Arg Val Lys Glu Val  Glu Glu Met Cys Lys  Arg Ser Leu
    2150                 2155                 2160

Glu Ser  Val Tyr Ser Leu Tyr  Pro Thr Leu Ser Arg  Leu Gln Ala
    2165                 2170                 2175

Ile Gly  Glu Leu Glu Ser Ile  Gly Glu Leu Phe Ser  Arg Ser Val
    2180                 2185                 2190

Thr His  Arg Gln Leu Ser Glu  Val Tyr Ile Lys Trp  Gln Lys His
    2195                 2200                 2205

Ser Gln  Leu Leu Lys Asp Ser  Asp Phe Ser Phe Gln  Glu Pro Ile
    2210                 2215                 2220

Met Ala  Leu Arg Thr Val Ile  Leu Glu Ile Leu Met  Glu Lys Glu
    2225                 2230                 2235

Met Asp  Asn Ser Gln Arg Glu  Cys Ile Lys Asp Ile  Leu Thr Lys
    2240                 2245                 2250

His Leu  Val Glu Leu Ser Ile  Leu Ala Arg Thr Phe  Lys Asn Thr
    2255                 2260                 2265

Gln Leu  Pro Glu Arg Ala Ile  Phe Gln Ile Lys Gln  Tyr Asn Ser
    2270                 2275                 2280

Val Ser  Cys Gly Val Ser Glu  Trp Gln Leu Glu Glu  Ala Gln Val
    2285                 2290                 2295

Phe Trp  Ala Lys Lys Glu Gln  Ser Leu Ala Leu Ser  Ile Leu Lys
    2300                 2305                 2310

Gln Met  Ile Lys Lys Leu Asp  Ala Ser Cys Ala Ala  Asn Asn Pro
```

```
    2315                2320                2325

Ser Leu  Lys Leu Thr Tyr Thr  Glu Cys Leu Arg Val  Cys Gly Asn
    2330                2335                2340

Trp Leu  Ala Glu Thr Cys Leu  Glu Asn Pro Ala Val  Ile Met Gln
    2345                2350                2355

Thr Tyr  Leu Glu Lys Ala Val  Glu Val Ala Gly Asn  Tyr Asp Gly
    2360                2365                2370

Glu Ser  Ser Asp Glu Leu Arg  Asn Gly Lys Met Lys  Ala Phe Leu
    2375                2380                2385

Ser Leu  Ala Arg Phe Ser Asp  Thr Gln Tyr Gln Arg  Ile Glu Asn
    2390                2395                2400

Tyr Met  Lys Ser Ser Glu Phe  Glu Asn Lys Gln Ala  Leu Leu Lys
    2405                2410                2415

Arg Ala  Lys Glu Glu Val Gly  Leu Leu Arg Glu His  Lys Ile Gln
    2420                2425                2430

Thr Asn  Arg Tyr Thr Val Lys  Val Gln Arg Glu Leu  Glu Leu Asp
    2435                2440                2445

Glu Leu  Ala Leu Arg Ala Leu  Lys Glu Asp Arg Lys  Arg Phe Leu
    2450                2455                2460

Cys Lys  Ala Val Glu Asn Tyr  Ile Asn Cys Leu Leu  Ser Gly Glu
    2465                2470                2475

Glu His  Asp Met Trp Val Phe  Arg Leu Cys Ser Leu  Trp Leu Glu
    2480                2485                2490

Asn Ser  Gly Val Ser Glu Val  Asn Gly Met Met Lys  Arg Asp Gly
    2495                2500                2505

Met Lys  Ile Pro Thr Tyr Lys  Phe Leu Pro Leu Met  Tyr Gln Leu
    2510                2515                2520

Ala Ala  Arg Met Gly Thr Lys  Met Met Gly Gly Leu  Gly Phe His
    2525                2530                2535

Glu Val  Leu Asn Asn Leu Ile  Ser Arg Ile Ser Met  Asp His Pro
    2540                2545                2550

His His  Thr Leu Phe Ile Ile  Leu Ala Leu Ala Asn  Ala Asn Arg
    2555                2560                2565

Asp Glu  Phe Leu Thr Lys Pro  Glu Val Ala Arg Arg  Ser Arg Ile
    2570                2575                2580

Thr Lys  Asn Val Pro Lys Gln  Ser Ser Gln Leu Asp  Glu Asp Arg
    2585                2590                2595

Thr Glu  Ala Ala Asn Arg Ile  Ile Cys Thr Ile Arg  Ser Arg Arg
    2600                2605                2610

Pro Gln  Met Val Arg Ser Val  Glu Ala Leu Cys Asp  Ala Tyr Ile
    2615                2620                2625

Ile Leu  Ala Asn Leu Asp Ala  Thr Gln Trp Lys Thr  Gln Arg Lys
    2630                2635                2640

Gly Ile  Asn Ile Pro Ala Asp  Gln Pro Ile Thr Lys  Leu Lys Asn
    2645                2650                2655

Leu Glu  Asp Val Val Val Pro  Thr Met Glu Ile Lys  Val Asp His
    2660                2665                2670

Thr Gly  Glu Tyr Gly Asn Leu  Val Thr Ile Gln Ser  Phe Lys Ala
    2675                2680                2685

Glu Phe  Arg Leu Ala Gly Gly  Val Asn Leu Pro Lys  Ile Ile Asp
    2690                2695                2700

Cys Val  Gly Ser Asp Gly Lys  Glu Arg Arg Gln Leu  Val Lys Gly
    2705                2710                2715
```

```
Arg Asp  Asp Leu Arg Gln Asp  Ala Val Met Gln Gln  Val Phe Gln
    2720                 2725                 2730

Met Cys  Asn Thr Leu Leu Gln  Arg Asn Thr Glu Thr  Arg Lys Arg
    2735                 2740                 2745

Lys Leu  Thr Ile Cys Thr Tyr  Lys Val Val Pro Leu  Ser Gln Arg
    2750                 2755                 2760

Ser Gly  Val Leu Glu Trp Cys  Thr Gly Thr Val Pro  Ile Gly Glu
    2765                 2770                 2775

Phe Leu  Val Asn Asn Glu Asp  Gly Ala His Lys Arg  Tyr Arg Pro
    2780                 2785                 2790

Asn Asp  Phe Ser Ala Phe Gln  Cys Gln Lys Lys Met  Met Glu Val
    2795                 2800                 2805

Gln Lys  Lys Ser Phe Glu Glu  Lys Tyr Glu Val Phe  Met Asp Val
    2810                 2815                 2820

Cys Gln  Asn Phe Gln Pro Val  Phe Arg Tyr Phe Cys  Met Glu Lys
    2825                 2830                 2835

Phe Leu  Asp Pro Ala Ile Trp  Phe Glu Lys Arg Leu  Ala Tyr Thr
    2840                 2845                 2850

Arg Ser  Val Ala Thr Ser Ser  Ile Val Gly Tyr Ile  Leu Gly Leu
    2855                 2860                 2865

Gly Asp  Arg His Val Gln Asn  Ile Leu Ile Asn Glu  Gln Ser Ala
    2870                 2875                 2880

Glu Leu  Val His Ile Asp Leu  Gly Val Ala Phe Glu  Gln Gly Lys
    2885                 2890                 2895

Ile Leu  Pro Thr Pro Glu Thr  Val Pro Phe Arg Leu  Thr Arg Asp
    2900                 2905                 2910

Ile Val  Asp Gly Met Gly Ile  Thr Gly Val Glu Gly  Val Phe Arg
    2915                 2920                 2925

Arg Cys  Cys Glu Lys Thr Met  Glu Val Met Arg Asn  Ser Gln Glu
    2930                 2935                 2940

Thr Leu  Leu Thr Ile Val Glu  Val Leu Leu Tyr Asp  Pro Leu Phe
    2945                 2950                 2955

Asp Trp  Thr Met Asn Pro Leu  Lys Ala Leu Tyr Leu  Gln Gln Arg
    2960                 2965                 2970

Pro Glu  Asp Glu Thr Glu Leu  His Pro Thr Leu Asn  Ala Asp Asp
    2975                 2980                 2985

Gln Glu  Cys Lys Arg Asn Leu  Ser Asp Ile Asp Gln  Ser Phe Asn
    2990                 2995                 3000

Lys Val  Ala Glu Arg Val Leu  Met Arg Leu Gln Glu  Lys Leu Lys
    3005                 3010                 3015

Gly Val  Glu Glu Gly Thr Val  Leu Ser Val Gly Gly  Gln Val Asn
    3020                 3025                 3030

Leu Leu  Ile Gln Gln Ala Ile  Asp Pro Lys Asn Leu  Ser Arg Leu
    3035                 3040                 3045

Phe Pro  Gly Trp Lys Ala Trp  Val
    3050                 3055
```

<210> SEQ ID NO 5
<211> LENGTH: 1130
<212> TYPE: PRT
<213> ORGANISM: Homo sapiens

<400> SEQUENCE: 5

Met Leu Glu Ile Cys Leu Lys Leu Val Gly Cys Lys Ser Lys Lys Gly

-continued

```
1               5                   10                  15

Leu Ser Ser Ser Ser Ser Cys Tyr Leu Glu Glu Ala Leu Gln Arg Pro
            20                  25                  30

Val Ala Ser Asp Phe Glu Pro Gln Gly Leu Ser Glu Ala Ala Arg Trp
        35                  40                  45

Asn Ser Lys Glu Asn Leu Leu Ala Gly Pro Ser Glu Asn Asp Pro Asn
    50                  55                  60

Leu Phe Val Ala Leu Tyr Asp Phe Val Ala Ser Gly Asp Asn Thr Leu
65                  70                  75                  80

Ser Ile Thr Lys Gly Glu Lys Leu Arg Val Leu Gly Tyr Asn His Asn
                85                  90                  95

Gly Glu Trp Cys Glu Ala Gln Thr Lys Asn Gly Gln Gly Trp Val Pro
            100                 105                 110

Ser Asn Tyr Ile Thr Pro Val Asn Ser Leu Glu Lys His Ser Trp Tyr
        115                 120                 125

His Gly Pro Val Ser Arg Asn Ala Ala Glu Tyr Leu Leu Ser Ser Gly
    130                 135                 140

Ile Asn Gly Ser Phe Leu Val Arg Glu Ser Glu Ser Ser Pro Gly Gln
145                 150                 155                 160

Arg Ser Ile Ser Leu Arg Tyr Glu Gly Arg Val Tyr His Tyr Arg Ile
                165                 170                 175

Asn Thr Ala Ser Asp Gly Lys Leu Tyr Val Ser Ser Glu Ser Arg Phe
            180                 185                 190

Asn Thr Leu Ala Glu Leu Val His His His Ser Thr Val Ala Asp Gly
        195                 200                 205

Leu Ile Thr Thr Leu His Tyr Pro Ala Pro Lys Arg Asn Lys Pro Thr
    210                 215                 220

Val Tyr Gly Val Ser Pro Asn Tyr Asp Lys Trp Glu Met Glu Arg Thr
225                 230                 235                 240

Asp Ile Thr Met Lys His Lys Leu Gly Gly Gly Gln Tyr Gly Glu Val
                245                 250                 255

Tyr Glu Gly Val Trp Lys Lys Tyr Ser Leu Thr Val Ala Val Lys Thr
            260                 265                 270

Leu Lys Glu Asp Thr Met Glu Val Glu Glu Phe Leu Lys Glu Ala Ala
        275                 280                 285

Val Met Lys Glu Ile Lys His Pro Asn Leu Val Gln Leu Leu Gly Val
    290                 295                 300

Cys Thr Arg Glu Pro Pro Phe Tyr Ile Ile Thr Glu Phe Met Thr Tyr
305                 310                 315                 320

Gly Asn Leu Leu Asp Tyr Leu Arg Glu Cys Asn Arg Gln Glu Val Asn
                325                 330                 335

Ala Val Val Leu Leu Tyr Met Ala Thr Gln Ile Ser Ser Ala Met Glu
            340                 345                 350

Tyr Leu Glu Lys Lys Asn Phe Ile His Arg Asp Leu Ala Ala Arg Asn
        355                 360                 365

Cys Leu Val Gly Glu Asn His Leu Val Lys Val Ala Asp Phe Gly Leu
    370                 375                 380

Ser Arg Leu Met Thr Gly Asp Thr Tyr Thr Ala His Ala Gly Ala Lys
385                 390                 395                 400

Phe Pro Ile Lys Trp Thr Ala Pro Glu Ser Leu Ala Tyr Asn Lys Phe
                405                 410                 415

Ser Ile Lys Ser Asp Val Trp Ala Phe Gly Val Leu Leu Trp Glu Ile
            420                 425                 430
```

```
Ala Thr Tyr Gly Met Ser Pro Tyr Pro Gly Ile Asp Leu Ser Gln Val
        435                 440                 445

Tyr Glu Leu Leu Glu Lys Asp Tyr Arg Met Glu Arg Pro Glu Gly Cys
    450                 455                 460

Pro Glu Lys Val Tyr Glu Leu Met Arg Ala Cys Trp Gln Trp Asn Pro
465                 470                 475                 480

Ser Asp Arg Pro Ser Phe Ala Glu Ile His Gln Ala Phe Glu Thr Met
                485                 490                 495

Phe Gln Glu Ser Ser Ile Ser Asp Glu Val Glu Lys Glu Leu Gly Lys
            500                 505                 510

Gln Gly Val Arg Gly Ala Val Ser Thr Leu Leu Gln Ala Pro Glu Leu
        515                 520                 525

Pro Thr Lys Thr Arg Thr Ser Arg Arg Ala Ala Glu His Arg Asp Thr
    530                 535                 540

Thr Asp Val Pro Glu Met Pro His Ser Lys Gly Gln Gly Glu Ser Asp
545                 550                 555                 560

Pro Leu Asp His Glu Pro Ala Val Ser Pro Leu Leu Pro Arg Lys Glu
                565                 570                 575

Arg Gly Pro Pro Glu Gly Gly Leu Asn Glu Asp Glu Arg Leu Leu Pro
            580                 585                 590

Lys Asp Lys Lys Thr Asn Leu Phe Ser Ala Leu Ile Lys Lys Lys Lys
        595                 600                 605

Lys Thr Ala Pro Thr Pro Pro Lys Arg Ser Ser Ser Phe Arg Glu Met
    610                 615                 620

Asp Gly Gln Pro Glu Arg Arg Gly Ala Gly Glu Glu Glu Gly Arg Asp
625                 630                 635                 640

Ile Ser Asn Gly Ala Leu Ala Phe Thr Pro Leu Asp Thr Ala Asp Pro
                645                 650                 655

Ala Lys Ser Pro Lys Pro Ser Asn Gly Ala Gly Val Pro Asn Gly Ala
            660                 665                 670

Leu Arg Glu Ser Gly Gly Ser Gly Phe Arg Ser Pro His Leu Trp Lys
        675                 680                 685

Lys Ser Ser Thr Leu Thr Ser Ser Arg Leu Ala Thr Gly Glu Glu Glu
    690                 695                 700

Gly Gly Gly Ser Ser Ser Lys Arg Phe Leu Arg Ser Cys Ser Ala Ser
705                 710                 715                 720

Cys Val Pro His Gly Ala Lys Asp Thr Glu Trp Arg Ser Val Thr Leu
                725                 730                 735

Pro Arg Asp Leu Gln Ser Thr Gly Arg Gln Phe Asp Ser Ser Thr Phe
            740                 745                 750

Gly Gly His Lys Ser Glu Lys Pro Ala Leu Pro Arg Lys Arg Ala Gly
        755                 760                 765

Glu Asn Arg Ser Asp Gln Val Thr Arg Gly Thr Val Thr Pro Pro Pro
    770                 775                 780

Arg Leu Val Lys Lys Asn Glu Glu Ala Ala Asp Glu Val Phe Lys Asp
785                 790                 795                 800

Ile Met Glu Ser Ser Pro Gly Ser Ser Pro Pro Asn Leu Thr Pro Lys
                805                 810                 815

Pro Leu Arg Arg Gln Val Thr Val Ala Pro Ala Ser Gly Leu Pro His
            820                 825                 830

Lys Glu Glu Ala Gly Lys Gly Ser Ala Leu Gly Thr Pro Ala Ala Ala
        835                 840                 845
```

```
Glu Pro Val Thr Pro Thr Ser Lys Ala Gly Ser Gly Ala Pro Gly Gly
    850                 855                 860

Thr Ser Lys Gly Pro Ala Glu Glu Ser Arg Val Arg Arg His Lys His
865                 870                 875                 880

Ser Ser Glu Ser Pro Gly Arg Asp Lys Gly Lys Leu Ser Arg Leu Lys
                885                 890                 895

Pro Ala Pro Pro Pro Pro Pro Ala Ala Ser Ala Gly Lys Ala Gly Gly
            900                 905                 910

Lys Pro Ser Gln Ser Pro Ser Gln Glu Ala Ala Gly Glu Ala Val Leu
        915                 920                 925

Gly Ala Lys Thr Lys Ala Thr Ser Leu Val Asp Ala Val Asn Ser Asp
    930                 935                 940

Ala Ala Lys Pro Ser Gln Pro Gly Glu Gly Leu Lys Lys Pro Val Leu
945                 950                 955                 960

Pro Ala Thr Pro Lys Pro Gln Ser Ala Lys Pro Ser Gly Thr Pro Ile
                965                 970                 975

Ser Pro Ala Pro Val Pro Ser Thr Leu Pro Ser Ala Ser Ser Ala Leu
            980                 985                 990

Ala Gly Asp Gln Pro Ser Ser Thr  Ala Phe Ile Pro Leu  Ile Ser Thr
        995                 1000                1005

Arg Val  Ser Leu Arg Lys Thr  Arg Gln Pro Pro Glu  Arg Ile Ala
    1010                1015                1020

Ser Gly  Ala Ile Thr Lys Gly  Val Val Leu Asp Ser  Thr Glu Ala
    1025                1030                1035

Leu Cys  Leu Ala Ile Ser Arg  Asn Ser Glu Gln Met  Ala Ser His
    1040                1045                1050

Ser Ala  Val Leu Glu Ala Gly  Lys Asn Leu Tyr Thr  Phe Cys Val
    1055                1060                1065

Ser Tyr  Val Asp Ser Ile Gln  Gln Met Arg Asn Lys  Phe Ala Phe
    1070                1075                1080

Arg Glu  Ala Ile Asn Lys Leu  Glu Asn Asn Leu Arg  Glu Leu Gln
    1085                1090                1095

Ile Cys  Pro Ala Thr Ala Gly  Ser Gly Pro Ala Ala  Thr Gln Asp
    1100                1105                1110

Phe Ser  Lys Leu Leu Ser Ser  Val Lys Glu Ile Ser  Asp Ile Val
    1115                1120                1125

Gln Arg
    1130


<210> SEQ ID NO 6
<211> LENGTH: 707
<212> TYPE: PRT
<213> ORGANISM: Homo sapiens

<400> SEQUENCE: 6

Met Asn Gln Glu Leu Leu Ser Val Gly Ser Lys Arg Arg Arg Thr Gly
1               5                   10                  15

Gly Ser Leu Arg Gly Asn Pro Ser Ser Ser Gln Val Asp Glu Glu Gln
            20                  25                  30

Met Asn Arg Val Val Glu Glu Glu Gln Gln Gln Gln Leu Arg Gln Gln
        35                  40                  45

Glu Glu Glu His Thr Ala Arg Asn Gly Glu Val Val Gly Val Glu Pro
    50                  55                  60

Arg Pro Gly Gly Gln Asn Asp Ser Gln Gln Gly Gln Leu Glu Glu Asn
65                  70                  75                  80
```

```
Asn Asn Arg Phe Ile Ser Val Asp Glu Asp Ser Ser Gly Asn Gln Glu
                85                  90                  95

Glu Gln Glu Glu Asp Glu Glu His Ala Gly Glu Gln Asp Glu Glu Asp
            100                 105                 110

Glu Glu Glu Glu Glu Met Asp Gln Glu Ser Asp Asp Phe Asp Gln Ser
        115                 120                 125

Asp Asp Ser Ser Arg Glu Asp Glu His Thr His Thr Asn Ser Val Thr
    130                 135                 140

Asn Ser Ser Ser Ile Val Asp Leu Pro Val His Gln Leu Ser Ser Pro
145                 150                 155                 160

Phe Tyr Thr Lys Thr Thr Lys Met Lys Arg Lys Leu Asp His Gly Ser
                165                 170                 175

Glu Val Arg Ser Phe Ser Leu Gly Lys Lys Pro Cys Lys Val Ser Glu
            180                 185                 190

Tyr Thr Ser Thr Thr Gly Leu Val Pro Cys Ser Ala Thr Pro Thr Thr
        195                 200                 205

Phe Gly Asp Leu Arg Ala Ala Asn Gly Gln Gly Gln Gln Arg Arg Arg
    210                 215                 220

Ile Thr Ser Val Gln Pro Pro Thr Gly Leu Gln Glu Trp Leu Lys Met
225                 230                 235                 240

Phe Gln Ser Trp Ser Gly Pro Glu Lys Leu Leu Ala Leu Asp Glu Leu
                245                 250                 255

Ile Asp Ser Cys Glu Pro Thr Gln Val Lys His Met Met Gln Val Ile
            260                 265                 270

Glu Pro Gln Phe Gln Arg Asp Phe Ile Ser Leu Leu Pro Lys Glu Leu
        275                 280                 285

Ala Leu Tyr Val Leu Ser Phe Leu Glu Pro Lys Asp Leu Leu Gln Ala
    290                 295                 300

Ala Gln Thr Cys Arg Tyr Trp Arg Ile Leu Ala Glu Asp Asn Leu Leu
305                 310                 315                 320

Trp Arg Glu Lys Cys Lys Glu Glu Gly Ile Asp Glu Pro Leu His Ile
                325                 330                 335

Lys Arg Arg Lys Val Ile Lys Pro Gly Phe Ile His Ser Pro Trp Lys
            340                 345                 350

Ser Ala Tyr Ile Arg Gln His Arg Ile Asp Thr Asn Trp Arg Arg Gly
        355                 360                 365

Glu Leu Lys Ser Pro Lys Val Leu Lys Gly His Asp Asp His Val Ile
    370                 375                 380

Thr Cys Leu Gln Phe Cys Gly Asn Arg Ile Val Ser Gly Ser Asp Asp
385                 390                 395                 400

Asn Thr Leu Lys Val Trp Ser Ala Val Thr Gly Lys Cys Leu Arg Thr
                405                 410                 415

Leu Val Gly His Thr Gly Gly Val Trp Ser Ser Gln Met Arg Asp Asn
            420                 425                 430

Ile Ile Ile Ser Gly Ser Thr Asp Arg Thr Leu Lys Val Trp Asn Ala
        435                 440                 445

Glu Thr Gly Glu Cys Ile His Thr Leu Tyr Gly His Thr Ser Thr Val
    450                 455                 460

Arg Cys Met His Leu His Glu Lys Arg Val Val Ser Gly Ser Arg Asp
465                 470                 475                 480

Ala Thr Leu Arg Val Trp Asp Ile Glu Thr Gly Gln Cys Leu His Val
                485                 490                 495
```

```
Leu Met Gly His Val Ala Ala Val Arg Cys Val Gln Tyr Asp Gly Arg
            500                 505                 510

Arg Val Val Ser Gly Ala Tyr Asp Phe Met Val Lys Val Trp Asp Pro
        515                 520                 525

Glu Thr Glu Thr Cys Leu His Thr Leu Gln Gly His Thr Asn Arg Val
    530                 535                 540

Tyr Ser Leu Gln Phe Asp Gly Ile His Val Val Ser Gly Ser Leu Asp
545                 550                 555                 560

Thr Ser Ile Arg Val Trp Asp Val Glu Thr Gly Asn Cys Ile His Thr
                565                 570                 575

Leu Thr Gly His Gln Ser Leu Thr Ser Gly Met Glu Leu Lys Asp Asn
            580                 585                 590

Ile Leu Val Ser Gly Asn Ala Asp Ser Thr Val Lys Ile Trp Asp Ile
        595                 600                 605

Lys Thr Gly Gln Cys Leu Gln Thr Leu Gln Gly Pro Asn Lys His Gln
    610                 615                 620

Ser Ala Val Thr Cys Leu Gln Phe Asn Lys Asn Phe Val Ile Thr Ser
625                 630                 635                 640

Ser Asp Asp Gly Thr Val Lys Leu Trp Asp Leu Lys Thr Gly Glu Phe
                645                 650                 655

Ile Arg Asn Leu Val Thr Leu Glu Ser Gly Gly Ser Gly Gly Val Val
            660                 665                 670

Trp Arg Ile Arg Ala Ser Asn Thr Lys Leu Val Cys Ala Val Gly Ser
        675                 680                 685

Arg Asn Gly Thr Glu Glu Thr Lys Leu Leu Val Leu Asp Phe Asp Val
    690                 695                 700

Asp Met Lys
705


<210> SEQ ID NO 7
<211> LENGTH: 662
<212> TYPE: PRT
<213> ORGANISM: Homo sapiens

<400> SEQUENCE: 7

Met Ser His Val Ala Val Glu Asn Ala Leu Gly Leu Asp Gln Gln Phe
1               5                   10                  15

Ala Gly Leu Asp Leu Asn Ser Ser Asp Asn Gln Ser Gly Gly Ser Thr
            20                  25                  30

Ala Ser Lys Gly Arg Tyr Ile Pro Pro His Leu Arg Asn Arg Glu Ala
        35                  40                  45

Thr Lys Gly Phe Tyr Asp Lys Asp Ser Ser Gly Trp Ser Ser Ser Lys
    50                  55                  60

Asp Lys Asp Ala Tyr Ser Ser Phe Gly Ser Arg Ser Asp Ser Arg Gly
65                  70                  75                  80

Lys Ser Ser Phe Phe Ser Asp Arg Gly Ser Gly Ser Arg Gly Arg Phe
                85                  90                  95

Asp Asp Arg Gly Arg Ser Asp Tyr Asp Gly Ile Gly Ser Arg Gly Asp
            100                 105                 110

Arg Ser Gly Phe Gly Lys Phe Glu Arg Gly Gly Asn Ser Arg Trp Cys
        115                 120                 125

Asp Lys Ser Asp Glu Asp Asp Trp Ser Lys Pro Leu Pro Pro Ser Glu
    130                 135                 140

Arg Leu Glu Gln Glu Leu Phe Ser Gly Gly Asn Thr Gly Ile Asn Phe
145                 150                 155                 160
```

```
Glu Lys Tyr Asp Asp Ile Pro Val Glu Ala Thr Gly Asn Asn Cys Pro
                165                 170                 175

Pro His Ile Glu Ser Phe Ser Asp Val Glu Met Gly Glu Ile Ile Met
            180                 185                 190

Gly Asn Ile Glu Leu Thr Arg Tyr Thr Arg Pro Thr Pro Val Gln Lys
        195                 200                 205

His Ala Ile Pro Ile Ile Lys Glu Lys Arg Asp Leu Met Ala Cys Ala
    210                 215                 220

Gln Thr Gly Ser Gly Lys Thr Ala Ala Phe Leu Leu Pro Ile Leu Ser
225                 230                 235                 240

Gln Ile Tyr Ser Asp Gly Pro Gly Glu Ala Leu Arg Ala Met Lys Glu
                245                 250                 255

Asn Gly Arg Tyr Gly Arg Arg Lys Gln Tyr Pro Ile Ser Leu Val Leu
            260                 265                 270

Ala Pro Thr Arg Glu Leu Ala Val Gln Ile Tyr Glu Glu Ala Arg Lys
        275                 280                 285

Phe Ser Tyr Arg Ser Arg Val Arg Pro Cys Val Val Tyr Gly Gly Ala
    290                 295                 300

Asp Ile Gly Gln Gln Ile Arg Asp Leu Glu Arg Gly Cys His Leu Leu
305                 310                 315                 320

Val Ala Thr Pro Gly Arg Leu Val Asp Met Met Glu Arg Gly Lys Ile
                325                 330                 335

Gly Leu Asp Phe Cys Lys Tyr Leu Val Leu Asp Glu Ala Asp Arg Met
            340                 345                 350

Leu Asp Met Gly Phe Glu Pro Gln Ile Arg Arg Ile Val Glu Gln Asp
        355                 360                 365

Thr Met Pro Pro Lys Gly Val Arg His Thr Met Met Phe Ser Ala Thr
    370                 375                 380

Phe Pro Lys Glu Ile Gln Met Leu Ala Arg Asp Phe Leu Asp Glu Tyr
385                 390                 395                 400

Ile Phe Leu Ala Val Gly Arg Val Gly Ser Thr Ser Glu Asn Ile Thr
                405                 410                 415

Gln Lys Val Val Trp Val Glu Glu Ser Asp Lys Arg Ser Phe Leu Leu
            420                 425                 430

Asp Leu Leu Asn Ala Thr Gly Lys Asp Ser Leu Thr Leu Val Phe Val
        435                 440                 445

Glu Thr Lys Lys Gly Ala Asp Ser Leu Glu Asp Phe Leu Tyr His Glu
    450                 455                 460

Gly Tyr Ala Cys Thr Ser Ile His Gly Asp Arg Ser Gln Arg Asp Arg
465                 470                 475                 480

Glu Glu Ala Leu His Gln Phe Arg Ser Gly Lys Ser Pro Ile Leu Val
                485                 490                 495

Ala Thr Ala Val Ala Ala Arg Gly Leu Asp Ile Ser Asn Val Lys His
            500                 505                 510

Val Ile Asn Phe Asp Leu Pro Ser Asp Ile Glu Glu Tyr Val His Arg
        515                 520                 525

Ile Gly Arg Thr Gly Arg Val Gly Asn Leu Gly Leu Ala Thr Ser Phe
    530                 535                 540

Phe Asn Glu Arg Asn Ile Asn Ile Thr Lys Asp Leu Leu Asp Leu Leu
545                 550                 555                 560

Val Glu Ala Lys Gln Glu Val Pro Ser Trp Leu Glu Asn Met Ala Tyr
                565                 570                 575
```

```
Glu His His Tyr Lys Gly Ser Ser Arg Gly Arg Ser Lys Ser Ser Arg
            580                 585                 590

Phe Ser Gly Gly Phe Gly Ala Arg Asp Tyr Arg Gln Ser Ser Gly Ala
        595                 600                 605

Ser Ser Ser Ser Phe Ser Ser Ser Arg Ala Ser Ser Ser Arg Ser Gly
    610                 615                 620

Gly Gly Gly His Gly Ser Ser Arg Gly Phe Gly Gly Gly Gly Tyr Gly
625                 630                 635                 640

Gly Phe Tyr Asn Ser Asp Gly Tyr Gly Gly Asn Tyr Asn Ser Gln Gly
                645                 650                 655

Val Asp Trp Trp Gly Asn
            660


<210> SEQ ID NO 8
<211> LENGTH: 360
<212> TYPE: PRT
<213> ORGANISM: Homo sapiens

<400> SEQUENCE: 8

Met Ala Ala Ala Ala Ala Ala Gly Ala Gly Pro Glu Met Val Arg Gly
1               5                   10                  15

Gln Val Phe Asp Val Gly Pro Arg Tyr Thr Asn Leu Ser Tyr Ile Gly
            20                  25                  30

Glu Gly Ala Tyr Gly Met Val Cys Ser Ala Tyr Asp Asn Val Asn Lys
        35                  40                  45

Val Arg Val Ala Ile Lys Lys Ile Ser Pro Phe Glu His Gln Thr Tyr
    50                  55                  60

Cys Gln Arg Thr Leu Arg Glu Ile Lys Ile Leu Leu Arg Phe Arg His
65                  70                  75                  80

Glu Asn Ile Ile Gly Ile Asn Asp Ile Ile Arg Ala Pro Thr Ile Glu
                85                  90                  95

Gln Met Lys Asp Val Tyr Ile Val Gln Asp Leu Met Glu Thr Asp Leu
            100                 105                 110

Tyr Lys Leu Leu Lys Thr Gln His Leu Ser Asn Asp His Ile Cys Tyr
        115                 120                 125

Phe Leu Tyr Gln Ile Leu Arg Gly Leu Lys Tyr Ile His Ser Ala Asn
    130                 135                 140

Val Leu His Arg Asp Leu Lys Pro Ser Asn Leu Leu Leu Asn Thr Thr
145                 150                 155                 160

Cys Asp Leu Lys Ile Cys Asp Phe Gly Leu Ala Arg Val Ala Asp Pro
                165                 170                 175

Asp His Asp His Thr Gly Phe Leu Thr Glu Tyr Val Ala Thr Arg Trp
            180                 185                 190

Tyr Arg Ala Pro Glu Ile Met Leu Asn Ser Lys Gly Tyr Thr Lys Ser
        195                 200                 205

Ile Asp Ile Trp Ser Val Gly Cys Ile Leu Ala Glu Met Leu Ser Asn
    210                 215                 220

Arg Pro Ile Phe Pro Gly Lys His Tyr Leu Asp Gln Leu Asn His Ile
225                 230                 235                 240

Leu Gly Ile Leu Gly Ser Pro Ser Gln Glu Asp Leu Asn Cys Ile Ile
                245                 250                 255

Asn Leu Lys Ala Arg Asn Tyr Leu Leu Ser Leu Pro His Lys Asn Lys
            260                 265                 270

Val Pro Trp Asn Arg Leu Phe Pro Asn Ala Asp Ser Lys Ala Leu Asp
        275                 280                 285
```

```
Leu Leu Asp Lys Met Leu Thr Phe Asn Pro His Lys Arg Ile Glu Val
    290                 295                 300

Glu Gln Ala Leu Ala His Pro Tyr Leu Glu Gln Tyr Tyr Asp Pro Ser
305                 310                 315                 320

Asp Glu Pro Ile Ala Glu Ala Pro Phe Lys Phe Asp Met Glu Leu Asp
                325                 330                 335

Asp Leu Pro Lys Glu Lys Leu Lys Glu Leu Ile Phe Glu Glu Thr Ala
            340                 345                 350

Arg Phe Gln Pro Gly Tyr Arg Ser
        355                 360


<210> SEQ ID NO 9
<211> LENGTH: 340
<212> TYPE: PRT
<213> ORGANISM: Homo sapiens

<400> SEQUENCE: 9

Met Ser Glu Leu Asp Gln Leu Arg Gln Glu Ala Glu Gln Leu Lys Asn
1               5                   10                  15

Gln Ile Arg Asp Ala Arg Lys Ala Cys Ala Asp Ala Thr Leu Ser Gln
            20                  25                  30

Ile Thr Asn Asn Ile Asp Pro Val Gly Arg Ile Gln Met Arg Thr Arg
        35                  40                  45

Arg Thr Leu Arg Gly His Leu Ala Lys Ile Tyr Ala Met His Trp Gly
    50                  55                  60

Thr Asp Ser Arg Leu Leu Val Ser Ala Ser Gln Asp Gly Lys Leu Ile
65                  70                  75                  80

Ile Trp Asp Ser Tyr Thr Thr Asn Lys Val His Ala Ile Pro Leu Arg
                85                  90                  95

Ser Ser Trp Val Met Thr Cys Ala Tyr Ala Pro Ser Gly Asn Tyr Val
            100                 105                 110

Ala Cys Gly Gly Leu Asp Asn Ile Cys Ser Ile Tyr Asn Leu Lys Thr
        115                 120                 125

Arg Glu Gly Asn Val Arg Val Ser Arg Glu Leu Ala Gly His Thr Gly
    130                 135                 140

Tyr Leu Ser Cys Cys Arg Phe Leu Asp Asp Asn Gln Ile Val Thr Ser
145                 150                 155                 160

Ser Gly Asp Thr Thr Cys Ala Leu Trp Asp Ile Glu Thr Gly Gln Gln
                165                 170                 175

Thr Thr Thr Phe Thr Gly His Thr Gly Asp Val Met Ser Leu Ser Leu
            180                 185                 190

Ala Pro Asp Thr Arg Leu Phe Val Ser Gly Ala Cys Asp Ala Ser Ala
        195                 200                 205

Lys Leu Trp Asp Val Arg Glu Gly Met Cys Arg Gln Thr Phe Thr Gly
    210                 215                 220

His Glu Ser Asp Ile Asn Ala Ile Cys Phe Phe Pro Asn Gly Asn Ala
225                 230                 235                 240

Phe Ala Thr Gly Ser Asp Asp Ala Thr Cys Arg Leu Phe Asp Leu Arg
                245                 250                 255

Ala Asp Gln Glu Leu Met Thr Tyr Ser His Asp Asn Ile Ile Cys Gly
            260                 265                 270

Ile Thr Ser Val Ser Phe Ser Lys Ser Gly Arg Leu Leu Leu Ala Gly
        275                 280                 285

Tyr Asp Asp Phe Asn Cys Asn Val Trp Asp Ala Leu Lys Ala Asp Arg
```

```
    290                 295                 300

Ala Gly Val Leu Ala Gly His Asp Asn Arg Val Ser Cys Leu Gly Val
305                 310                 315                 320

Thr Asp Asp Gly Met Ala Val Ala Thr Gly Ser Trp Asp Ser Phe Leu
                325                 330                 335

Lys Ile Trp Asn
            340


<210> SEQ ID NO 10
<211> LENGTH: 9
<212> TYPE: PRT
<213> ORGANISM: Artificial Sequence
<220> FEATURE:
<223> OTHER INFORMATION: Chemically synthesized peptide

<400> SEQUENCE: 10

Lys Val Tyr Glu Gly Val Trp Lys Lys
1               5


<210> SEQ ID NO 11
<211> LENGTH: 8
<212> TYPE: PRT
<213> ORGANISM: Artificial Sequence
<220> FEATURE:
<223> OTHER INFORMATION: Parental peptide

<400> SEQUENCE: 11

Leu Met Pro Lys His Phe Ile Arg
1               5


<210> SEQ ID NO 12
<211> LENGTH: 8
<212> TYPE: PRT
<213> ORGANISM: Artificial Sequence
<220> FEATURE:
<223> OTHER INFORMATION: Missense mutant peptide

<400> SEQUENCE: 12

Leu Met Pro Lys Leu Phe Ile Arg
1               5


<210> SEQ ID NO 13
<211> LENGTH: 9
<212> TYPE: PRT
<213> ORGANISM: Artificial Sequence
<220> FEATURE:
<223> OTHER INFORMATION: Chemically synthesized peptide

<400> SEQUENCE: 13

Ala Ser Ile Leu Leu Met Thr Val Thr
1               5


<210> SEQ ID NO 14
<211> LENGTH: 9
<212> TYPE: PRT
<213> ORGANISM: Artificial Sequence
<220> FEATURE:
<223> OTHER INFORMATION: Chemically synthesized peptide

<400> SEQUENCE: 14

Ser Ile Leu Leu Met Thr Val Thr Ser
1               5


<210> SEQ ID NO 15
<211> LENGTH: 9
```

<212> TYPE: PRT
<213> ORGANISM: Artificial Sequence
<220> FEATURE:
<223> OTHER INFORMATION: Chemically synthesized peptide

<400> SEQUENCE: 15

Ile Leu Leu Met Thr Val Thr Ser Ile
1 5

<210> SEQ ID NO 16
<211> LENGTH: 9
<212> TYPE: PRT
<213> ORGANISM: Artificial Sequence
<220> FEATURE:
<223> OTHER INFORMATION: Chemically synthesized peptide

<400> SEQUENCE: 16

Leu Leu Met Thr Val Thr Ser Ile Asp
1 5

<210> SEQ ID NO 17
<211> LENGTH: 9
<212> TYPE: PRT
<213> ORGANISM: Artificial Sequence
<220> FEATURE:
<223> OTHER INFORMATION: Chemically synthesized peptide

<400> SEQUENCE: 17

Leu Met Thr Val Thr Ser Ile Asp Arg
1 5

<210> SEQ ID NO 18
<211> LENGTH: 9
<212> TYPE: PRT
<213> ORGANISM: Artificial Sequence
<220> FEATURE:
<223> OTHER INFORMATION: Chemically synthesized peptide

<400> SEQUENCE: 18

Met Thr Val Thr Ser Ile Asp Arg Phe
1 5

<210> SEQ ID NO 19
<211> LENGTH: 9
<212> TYPE: PRT
<213> ORGANISM: Artificial Sequence
<220> FEATURE:
<223> OTHER INFORMATION: Chemically synthesized peptide

<400> SEQUENCE: 19

Thr Val Thr Ser Ile Asp Arg Phe Leu
1 5

<210> SEQ ID NO 20
<211> LENGTH: 9
<212> TYPE: PRT
<213> ORGANISM: Artificial Sequence
<220> FEATURE:
<223> OTHER INFORMATION: Chemically synthesized peptide

<400> SEQUENCE: 20

Val Thr Ser Ile Asp Arg Phe Leu Ala
1 5

<210> SEQ ID NO 21
<211> LENGTH: 9
<212> TYPE: PRT

```
<213> ORGANISM: Artificial Sequence
<220> FEATURE:
<223> OTHER INFORMATION: Chemically synthesized peptide

<400> SEQUENCE: 21

Thr Ser Ile Asp Arg Phe Leu Ala Val
1               5
```